United States Patent
Kaplan et al.

(10) Patent No.: US 10,335,519 B2
(45) Date of Patent: Jul. 2, 2019

(54) DYNAMIC SILK COATINGS FOR IMPLANTABLE DEVICES

(75) Inventors: David L. Kaplan, Concord, MA (US);
Lee W. Tien, Brookline, MA (US);
Gary G. Leisk, Wilmington, MA (US);
Tim Jia-Ching Lo, Lungtan (TW);
Cinzia Metallo, Somerville, MA (US);
Fiorenzo Omenetto, Wakefield, MA (US)

(73) Assignee: TRUSTEES OF TUFTS COLLEGE, Medford, MA (US)

(*) Notice: Subject to any disclaimer, the term of this patent is extended or adjusted under 35 U.S.C. 154(b) by 898 days.

(21) Appl. No.: 14/112,078

(22) PCT Filed: Apr. 20, 2012

(86) PCT No.: PCT/US2012/034490
§ 371 (c)(1),
(2), (4) Date: Jan. 26, 2015

(87) PCT Pub. No.: WO2012/145652
PCT Pub. Date: Oct. 26, 2012

(65) Prior Publication Data
US 2015/0202351 A1    Jul. 23, 2015

Related U.S. Application Data

(60) Provisional application No. 61/477,484, filed on Apr. 20, 2011.

(51) Int. Cl.
*A61L 31/10* (2006.01)
*A61B 5/0478* (2006.01)
(Continued)

(52) U.S. Cl.
CPC ............ *A61L 31/10* (2013.01); *A61B 5/0478* (2013.01); *A61B 5/686* (2013.01); *A61B 5/6868* (2013.01);
(Continued)

(58) Field of Classification Search
CPC .................................................... A61B 5/0478
See application file for complete search history.

(56) References Cited

U.S. PATENT DOCUMENTS 1,989,005 A    1/1935   Fink et al.
4,233,212 A    11/1980  Otoi et al.
(Continued)

FOREIGN PATENT DOCUMENTS

CA    2405850        10/2002
EP    0361391 A2     4/1990
(Continued)

OTHER PUBLICATIONS

Lu et al., Acta Biomater. 6(4):1380-1387 (2010). "Water-Insoluble Silk Films with Silk I Structure."
(Continued)

*Primary Examiner* — Carl H Layno
*Assistant Examiner* — Jennifer L Ghand
(74) *Attorney, Agent, or Firm* — Quarles & Brady LLP

(57) ABSTRACT

Provided herein relates to implantable devices and systems with dynamic silk coatings. In some embodiments, the dynamic silk coatings can be formed in situ or in vivo.

16 Claims, 22 Drawing Sheets

(51) Int. Cl.
*A61B 5/00* (2006.01)
*A61L 27/22* (2006.01)
*A61L 27/36* (2006.01)
*A61L 31/04* (2006.01)
*A61L 31/14* (2006.01)
*A61N 1/05* (2006.01)
*A61L 31/16* (2006.01)
*A61N 1/375* (2006.01)

(52) U.S. Cl.
CPC .......... *A61B 5/6877* (2013.01); *A61L 27/227* (2013.01); *A61L 27/3604* (2013.01); *A61L 27/3675* (2013.01); *A61L 31/047* (2013.01); *A61L 31/14* (2013.01); *A61L 31/16* (2013.01); *A61N 1/05* (2013.01); *A61N 1/0529* (2013.01); *A61B 5/4088* (2013.01); *A61B 5/4094* (2013.01); *A61B 2562/125* (2013.01); *A61L 2400/18* (2013.01); *A61L 2420/06* (2013.01); *A61N 1/0541* (2013.01); *A61N 1/375* (2013.01)

(56) References Cited

U.S. PATENT DOCUMENTS

| | | |
|---|---|---|
| 4,798,722 A | 1/1989 | Edman et al. |
| 4,806,355 A | 2/1989 | Goosen et al. |
| 4,820,418 A | 4/1989 | Hirotsu et al. |
| 5,015,476 A | 5/1991 | Cochrum et al. |
| 5,047,507 A | 9/1991 | Buchegger et al. |
| 5,093,489 A | 3/1992 | Diamantoglou |
| 5,245,012 A | 9/1993 | Lombari et al. |
| 5,263,992 A | 11/1993 | Guire |
| 5,270,419 A | 12/1993 | Domb |
| 5,290,494 A | 3/1994 | Coombes et al. |
| 5,538,735 A | 7/1996 | Ahn |
| 5,576,881 A | 11/1996 | Doerr et al. |
| 5,606,019 A | 2/1997 | Cappello |
| 5,728,810 A | 3/1998 | Lewis et al. |
| 5,770,193 A | 6/1998 | Vacanti et al. |
| 5,902,800 A | 5/1999 | Green et al. |
| 5,932,462 A | 8/1999 | Harris et al. |
| 5,994,099 A | 11/1999 | Lewis et al. |
| 6,106,816 A | 8/2000 | Hitchen |
| 6,110,590 A | 8/2000 | Zarkoob et al. |
| 6,123,819 A | 9/2000 | Peeters |
| 6,127,143 A | 10/2000 | Gunasekaran |
| 6,175,053 B1 | 1/2001 | Tsubouchi |
| 6,245,537 B1 | 6/2001 | Williams et al. |
| 6,267,776 B1 | 7/2001 | O'Connell |
| 6,302,848 B1 | 10/2001 | Larson et al. |
| 6,310,188 B1 | 10/2001 | Mukherjee |
| 6,325,810 B1 | 12/2001 | Hamilton et al. |
| 6,337,198 B1 | 1/2002 | Levene et al. |
| 6,372,244 B1 | 4/2002 | Antanavich et al. |
| 6,379,690 B2 | 4/2002 | Blanchard et al. |
| 6,387,413 B1 | 5/2002 | Miyata et al. |
| 6,395,734 B1 | 5/2002 | Tang et al. |
| 6,592,623 B1 | 7/2003 | Bowlin et al. |
| 6,815,427 B2 | 11/2004 | Tsubouchi et al. |
| 6,902,932 B2 | 6/2005 | Altman et al. |
| 7,041,797 B2 | 5/2006 | Vollrath |
| 7,057,023 B2 | 6/2006 | Islam et al. |
| 7,285,637 B2 | 10/2007 | Armato et al. |
| 7,635,755 B2 | 12/2009 | Kaplan et al. |
| 7,662,409 B2 | 2/2010 | Masters |
| 7,674,882 B2 | 3/2010 | Kaplan et al. |
| 7,727,575 B2 | 6/2010 | Kaplan et al. |
| 7,842,780 B2 | 11/2010 | Kaplan et al. |
| 7,960,509 B2 | 6/2011 | Kaplan et al. |
| 8,071,722 B2 | 12/2011 | Kaplan et al. |
| 2002/0028243 A1 | 3/2002 | Masters |
| 2003/0007991 A1 | 1/2003 | Masters |
| 2003/0183978 A1 | 10/2003 | Asakura |
| 2004/0005363 A1 | 1/2004 | Tsukada et al. |
| 2004/0266992 A1 | 12/2004 | Migliaresi et al. |
| 2005/0147681 A1 | 7/2005 | Zhao |
| 2005/0260706 A1 | 11/2005 | Kaplan et al. |
| 2007/0187862 A1 | 8/2007 | Kaplan et al. |
| 2007/0212730 A1 | 9/2007 | Vepari et al. |
| 2008/0058400 A1 | 3/2008 | Yang et al. |
| 2008/0085272 A1 | 4/2008 | Kaplan et al. |
| 2008/0293919 A1 | 11/2008 | Kaplan et al. |
| 2009/0171467 A1 | 7/2009 | Mann et al. |
| 2009/0202614 A1 | 8/2009 | Kaplan et al. |
| 2009/0232963 A1 | 9/2009 | Kaplan et al. |
| 2009/0234026 A1 | 9/2009 | Kaplan et al. |
| 2009/0297588 A1 | 12/2009 | Rheinnecker et al. |
| 2010/0028451 A1 | 2/2010 | Kaplan et al. |
| 2010/0046902 A1 | 2/2010 | Kaplan et al. |
| 2010/0055438 A1 | 3/2010 | Kaplan et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0095827 A1 | 4/2010 | Rheinnecker et al. |
| 2010/0096763 A1 | 4/2010 | Kaplan et al. |
| 2010/0120116 A1 | 5/2010 | Kaplan et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0292338 A1 | 11/2010 | Rheinnecker et al. |
| 2011/0008406 A1* | 1/2011 | Altman ............ A61K 38/1767 424/423 |
| 2011/0046686 A1 | 2/2011 | Kaplan et al. |
| 2011/0076384 A1 | 3/2011 | Cannizzaro et al. |
| 2011/0105402 A1 | 5/2011 | Kim et al. |
| 2011/0121485 A1 | 5/2011 | Rheinnecker et al. |
| 2011/0135697 A1 | 6/2011 | Omenetto et al. |
| 2011/0152214 A1 | 6/2011 | Boison et al. |
| 2011/0171239 A1 | 7/2011 | Kaplan et al. |
| 2011/0230747 A1* | 9/2011 | Rogers .................... A61B 5/05 600/377 |
| 2012/0076771 A1* | 3/2012 | Vepari ................ A61L 31/005 424/130.1 |
| 2012/0121820 A1 | 5/2012 | Kaplan et al. |
| 2012/0123519 A1 | 5/2012 | Lovett et al. |
| 2012/0231499 A1 | 9/2012 | Lee et al. |
| 2014/0145365 A1 | 5/2014 | Omenetto et al. |
| 2014/0378661 A1 | 12/2014 | Lo et al. |
| 2015/0045764 A1* | 2/2015 | Kaplan ................ A61K 9/0019 604/500 |

FOREIGN PATENT DOCUMENTS

| | | |
|---|---|---|
| EP | 0404097 A2 | 12/1990 |
| EP | 1440088 | 5/2008 |
| GB | 1182153 | 2/1970 |
| JP | 55-139427 | 10/1980 |
| JP | 56166235 | 12/1981 |
| JP | 58-38449 | 8/1983 |
| JP | 60-142259 | 7/1985 |
| JP | 60-259677 | 12/1985 |
| JP | 01118544 | 11/1989 |
| JP | 04-263611 | 9/1992 |
| JP | 05163132 | 6/1993 |
| JP | 06-346314 | 12/1994 |
| JP | 08-295697 | 11/1996 |
| JP | 10-36676 | 2/1998 |
| JP | 2000-273264 | 10/2000 |
| JP | 2003192807 | 7/2003 |
| JP | 2004068161 | 3/2004 |
| WO | WO-1993/011161 A1 | 6/1993 |
| WO | WO-1997/008315 A1 | 3/1997 |
| WO | 1999/001089 | 1/1999 |
| WO | 99/45964 A1 | 9/1999 |
| WO | 2001/036531 | 5/2001 |
| WO | 2001/056626 | 8/2001 |
| WO | 2002/072931 | 9/2002 |
| WO | 2003/022909 | 3/2003 |
| WO | 2003/038033 | 5/2003 |
| WO | 2004/000915 | 12/2003 |

(56) References Cited

FOREIGN PATENT DOCUMENTS

| | | |
|---|---|---|
| WO | 2004/041845 | 5/2004 |
| WO | 2005/012606 | 2/2005 |
| WO | 2005/123114 | 12/2005 |
| WO | WO-2006/076711 A2 | 7/2006 |
| WO | WO-2007/098951 A2 | 9/2007 |
| WO | 2008/052755 A2 | 5/2008 |
| WO | 2008/052775 A2 | 5/2008 |
| WO | 2008/127405 | 10/2008 |
| WO | 2009/126689 | 10/2009 |
| WO | 2009/153140 A2 | 12/2009 |
| WO | 2009/156226 | 12/2009 |
| WO | 2010/036992 | 4/2010 |
| WO | WO-2010/042798 A2 | 4/2010 |
| WO | WO-2010/057142 A2 | 5/2010 |
| WO | 2010/060600 A1 | 6/2010 |
| WO | 2011/006133 | 1/2011 |
| WO | WO-2011/006133 A2 | 1/2011 |
| WO | WO-2011/011347 A2 | 1/2011 |
| WO | WO-2012/047682 A2 | 4/2012 |

OTHER PUBLICATIONS

Marcovich et al., Urology, 57:806-810 (2001). "Comparison of 2-Octyl Cyanoacrylate Adhesive, Fibrin Glue, and Suturing for Wound Closure in the Porcine Urinary Tract."
Megeed et al., Pharmaceutical Research, 19(7):954-959 (2002). "Controlled release of plasmid DNA from a genetically engineered silk-elastinlike hydrogel."
Nazarov et al., Biomacromolecules, 5:718-726 (2004). "Porous 3-D Scaffolds from Regenerated Silk Fibroin."
Pandit et al., Archives of Biochemistry and Biophysics, 149:259-268 (1972). "Studies on Silk Fibroin. I. Molecular Weight, Sedimentation Coefficient, Viscosity and Optical Rotation of Silk Fibroin from Carbonate-Extracted Silk Fiber."
Petrini et al., Journal of Materials Science: Materials in Medicine, 12:849-853 (2001). "Silk fibroin-polyurethane scaffolds for tissue engineering."
Preul et al., J Neurosurg, 107:642-650 (2007). "Application of a hydrogel sealant improves watertight closures of duraplasty onlay grafts in a canine craniotomy model."
Pritchard et al., Journal of Controlled Release, 144:159-167 (2010). "Silk fibroin encapsulated powder reservoirs for sustained release of adenosine."
Pritchard et al., Expert Opinion on Drug Delivery, 8(6):797-811 (2011). "Silk fibroin biomaterials for controlled release drug delivery."
Pritchard et al., Macromol. Biosci., 13:311-320 (2013). "Effect of Silk Protein Processing on Drug Delivery from Silk Films."
Rajkhowa et al., Journal of Applied Polymer Science, 119:1339-1347 (2011). "Molecular Weight and Secondary Structure Change in Eri Silk During Alkali Degumming and Powdering."
Reneker et al., Nanotechnology, 7:216-223 (1996). "Nanometre diameter fibres of polymer, produced by electrospinning."
Samal et al., Macromol. Mater. Eng., DOI: 10.1002/mame.201200377 (2013). "Ultrasound Sonication Effects on Silk Fibroin Protein."
Sawyer et al., JAMA, 191(9):740-742 (1965). "Dextran therapy in thrombophlebitis." Abstract.
Silva et al., Macromol. Biosci., 8:000-000 (2008). "Genipin-Modified Silk Fibroin Nanometric Nets."
Soffer et al., J Biomater Sci Polym Ed., 19(5):653-664 Author Manuscript (2008). "Silk-Based Electrospun Tubular Scaffolds for Tissue Engineered Vascular Grafts."
Sofia et al., Journal of Biomedical Materials Research, 54(1):139-148 (2001). "Functionalized silk-based biomaterials for bone formation."
Spotnitz et al., Transfusion, 48:1502-1516 (2008). "Hemostats, sealants, and adhesives: components of the surgical toolbox."
Torchiana, J Card Surg, 18:504-506 (2003). "Polyethylene Glycol Based Synthetic Sealants: Potential Uses in Cardiac Surgery."
Tsukada et al., J. of Applied Polymer Science, 54(4):507-514 (1994). "Preparation and Application of Porous Silk Fibroin Materials."
U.S. Appl. No. 60/906,509, filed Mar. 13, 2007 by Omenetto et al.
U.S. Appl. No. 61/224,618, filed Jul. 10, 2009 by Numata et al.
Vanderhooft et al., Biomacromolecules, 8:2883-2889 (2007). "Synthesis and Characterization of Novel Thiol-Reactive Poly(ethylene glycol) Cross-Linkers for Extracellular-Matrix-Mimetic Biomaterials."
Wallace et al., J Biomed Mater Res (Appl Biomater), 58:545-555 (2001). "A Tissue Sealant Based on Reactive Multifunctional Polyethylene Glycol."
Wang et al., Langmuir, 21:11335-11341 (2005). "Biomaterial coatings by stepwise deposition of silk fibroin."
Wang et al., J Control Release, 134(2):81-90 (2009). "Growth Factor Gradients via Microsphere Delivery in Biopolymer Scaffolds for Osteochondral Tissue Engineering."
Wenk et al., Diss. Eth No. 18659 (2009). "Silk Fibroin As a Vehicle for Drug Delivery in Tissue Regeneration."
Wheat et al., Urol Clin North Am., 36(2):265-275 (2009). "Advances in Bioadhesives, Tissue Sealants, and Hemostatic Agents."
Wilson et al., PNAS, 98(24):13660-13664 (2001). "Surface organization and nanopatterning of collagen by dip-pen nanolithography."
Wray et al., J Biomed Mater Res Part B, 99B:89-101 (2011). "Effect of Processing on silk based biomaterials: Reproducibility and biocompatibility."
Yamada et al., Materials Science and Engineering C, 14:41-46 (2001). "Preparation of undegraded native molecular fibroin solution from silkworm cocoons."
Yamada et al., Thin Solid Films, 440:208-216 (2003). "AFM observation of silk fibroin on mica substrates: morphologies reflecting the secondary structures."
Yucel et al., J. Struct Biol., 170(2):406-412 (2010). "Non-equilibrium Silk Fibroin Adhesives."
Zhou et al., Proteins: Structure, Function, and Genetics, 44:119-122 (2001). "Silk Fibroin: Structural Implications of a Remarkable Amino Acid Sequence."
Zhou et al., Chem Commun, 2518-2519 (2001). "Preparation of a novel core-shell nanostructured gold colloid-silk fibroin bioconjugate by the protein in situ redox technique at room temperature."
Agarwal et al., Journal of Applied Polymer Science, 63(3):401-410 (1997). "Effect of Moisture Absorption on the Thermal Properties of Bombyx mori Silk Fibroin Films."
Altman et al., Biomaterials, 23:4131-4141 (2002). "Silk matrix for tissue engineered anterior cruciate ligaments."
Altman et al., Biomaterials, 24:401-416 (2003). "Silk-based biomaterials."
Ando et al, Reports on Progress in Polymer Physics in Japan, XXIII:775-778 (1980). "Piezoelectric and Related properties of Hydrated Silk Fibroin."
Asakura et al., Macromolecules, 17:1075-1081 (1984). NMR of silk fibroin 2. 13C NMR study of the chain dynamics and solution structure of Bombyx mori silk fibroin.
Asakura et al., Macromolecules, 18:1841-1845 (1985). "Conformation Characterization of Bombyx Mod Silk Fibroin in the Solid State by High-Frequency 13C Cross Polarization-Magic Angle Spinning NMR, X-ray Diffraction, and Infrared Spectroscopy."
Bini et al., J. Mol. Biol., 335:27-40 (2004). "Mapping Domain Structures in Silks from Insects and Spiders Related to Protein Assembly."
Cai et al., Int. J. Mol. Sci., 11:3529-3539 (2010). "Fabrication of Chitosan/Silk Fibroin Composite Nanofibers for Wound-dressing Applications."
Chao et al., J Biomed Mater Res B Appl Biomater., 95(1):84-90 Author Manuscript (2010). "Silk hydrogel for cartilage tissue engineering."
Chen et al., J Appl Polymer Sci, 65:2257-2262 (1997). "pH sensitivity and ion sensitivity of hydrogels based on complex-forming chitosan/silk fibroin interpenetrating polymer network."
Chen et al., J Appl Polymer Sci, 73:975-980 (1999). "Separation of alcohol-water mixture by pervaporation through a novel natural polymer blend membrane-chitosan/silk fibroin blend membrane-chitosan / silk fibroin blend membrane."

(56) References Cited

OTHER PUBLICATIONS

Chen et al., Biomacromolecules, 3:644-648 (2002). "Rheological Characterization of Nephila Spidroin Solution."
Chen et al., J Biomed Mater Res, 67A:559-570 (2003). "Human bone marrow stromal cell and ligament fibroblast responses on RGD-modified silk fibers."
Chen et al., Proteins: Structure, Function, and Bioinformatics, 68:223-231 (2007). "Conformation transition kinetics of Bombyx mori silk protein."
Chen et al., Food Research International, 44:1468-1475 (2011). "Improvement of physicochemical stabilities of emulsions containing oil droplets coated by non-globular protein-beet pectin complex membranes."
Demura et al., Biosensors, 4:361-372 (1989). "Immobilization of biocatalysts with Bombyx mori silk fibroin by several kinds of physical treatment and its application to glucose sensors."
Demura et al., J Membrane Science, 59:39-52 (1991). "Porous membrane of Bombyx mori silk fibroin: structure characterization, physical properties and application to glucose oxidase immobilization."
Derwent Record, Abstract of JP 08295697 A2 "Production of aqueous solution of silk fibroin at high concentration." Nov. 12, 1996.
Doshi et al. J Electrostatics, 35:151-160 (1995). "Electrospinning process and applications of electrospun fibers."
Dyakonov et al., Journal of Drug Delivery, Article 490514 (2012). "Design and Characterization of a Silk-Fibroin-Based Drug Delivery Platform Using Naproxen as a Model Drug."
Freddi et al., J Appl Polymer Sci, 56:1537-1545 (1995). "Silk fibroin/cellulose blend films: preparation, structure, and physical properties."
Furst et al., Ann Thorac Surg, 79:1522-1529 (2005). "Release of Glutaraldehyde From an Albumin-Glutaraldehyde Tissue Adhesive Causes Significant In Vitro and In Vivo Toxicity."
Gill et al., Urology, 65:463-466 (2005). "Improved Hemostasis During Laparoscopic Partial Nephrectomy Using Gelatin Matrix Thrombin Sealant."
Hijirida et al., Biophysical Journal, 71:3442-3447 (1996). "13C NMR of Nephila clavipes major ampullate silk gland."
Hinman et al., TIBTECH, 18:374-379 (2000). "Synthetic spider silk: a modular fiber."
Hofmann et al., Journal of Controlled Release, 111:219-227 (2006). "Silk fibroin as an organic polymer for controlled drug delivery."
Horan et al., Biomaterials, 26:3385-3393 (2005). "In vitro degradation of silk fibroin."
Hu et al., Biomacromolecules, 12:1686-1696 (2011). "Regulation of Silk Material Structure by Temperature-Controlled Water Vapor Annealing."
Huang et al., J Biomater Sci Polymer Edn, 12(9):979-993 (2001). "Engineered collagen-PEO nanofibers and fabrics."
Huang et al., Macromolecules, 33:2989-2997 (2000). "Generation of synthetic elastin-mimetic small diameter fibers and fiber networks."
Jang et al., Oral Surg Oral Med Oral Pathol Oral Radiol Endod, 109:831-836 (2010). "Restoration of peri-implant defects in immediate implant installations by Choukroun platelet-rich fibrin and silk fibroin powder combination graft."
Jenkins et al., Surgery, 20:124-132 (1946). "Clinical and Experimental Observations on the Use of Gelatin Sponge or Foam."
Jiang et al., Materials Letters, 60:919-925 (2006). "Tensile behavior and morphology of differently degummed silkworm (*Bombyx mori*) cocoon silk fibres."
Jin et al., Biomacromolecules, 3:1233-1239 (2002). "Electrospinning Bombyx mori silk with poly(ethylene oxide)."
Jin et al., Adv. Funct. Mater., 15:1241-1247 (2005). "Water-Stable Silk Films with Reduced β-Sheet Content."
Jin et al., Nature, 424:1057-1061 (2003). "Mechanism of silk processing in insects and spiders."
Kim et al., Biomacromolecules, 5:786-792 (2004). "Structure and Properties of Silk Hydrogels."
Kweon et al., J Appl Polymer Sci, 80:1848-1853 (2001). "Preparation of semi-interpenetrating polymer networks composed of silk fibroin and poly(ethylene glycol) macromer."
Lawrence et al., Biomaterials, 30(7):1299-1308 Author Manuscript (2009). "Silk film biomaterials for cornea tissue engineering."
Lazaris, Science, 295:472-476 (2002). "Spider silk fibers spun from soluble recombinant silk produced in mammalian cells."
Lee et al., Oral Surg Oral Med Oral Pathol Oral Radiol Endod, 109:e33-e38 (2010). "A combination graft of low-molecular-weight silk fibroin with Choukroun platelet-rich fibrin for rabbit calvarial defect."
Leisk et al., Adv. Mater., 22:711-715 (2010). "Electrogelation for Protein Adhesives."
Li et al., Biomaterials, 27:3115-3124 (2006). "Electrospun Silk-BMP-2 scaffolds for bone tissue engineering."
Li et al., J Mater Sci: Mater Med, 19:577-582 (2008). "Effect of silicon on the formation of silk fibroin/calcium phosphate composite."
Liang et al., J Appl Polymer Sci, 45:1937-1943 (1992). "Improvements of the physical properties of fibroin membranes with sodium alginate."
Lin et al., Pharmaceutical Research, 26(3):631-643 (2008). "PEG Hydrogels for the Controlled Release of Biomolecules in Regenerative Medicine."
Lowe et al., J Cardiovasc Surg, 48(3):323-331 (2007). "Evaluation of the topical hemostatic efficacy and safety of TISSEEL VH S/D fibrin sealant compared with currently licensed TISSEEL VH in patients undergoing cardiac surgery: a phase 3, randomized double-blind clinical study."
Lu et al., Biomacromolecules, 10:1032-1042 (2009). "Stabilization of Enzymes in Silk Films."
Kim et al., Nat Mater, 9(6):511-517 (2010). "Dissolvable films of silk fibroin for ultrathin, conformal bio-integrated electronics."
Polikov et al., Journal of Neuroscience Methods, 148(1):1-18 (2005). "Response of brain tissue to chronically implanted neural electrodes."
Abidian, M. R. et al., Multifunctional Nanobiomaterials for Neural Interfaces, Advanced Functional Materials, 19: 573-585 (2009).
Achyuta, A. K. H. et al, Biocompatibility assessment of insulating silicone polymer coatings using an in vitro glial scar assay, Macromolecular Bioscience, 10(8): 872-880 (2010).
Biran, R. et al., The brain tissue response to implanted silicon microelectrode arrays is increased when the device is tethered to the skull, J. Biomed Mater Res A., 82(1):169-78 (2007).
Bjornsson, C.S. et al. Effects of insertion conditions on tissue strain and vascular damage during neuroprosthetic device insertion, J. Neural Eng., 3(3)196-207 (2006).
Chorover, S.L and Deluca, A-M., A sweet new multiple electrode for chronic single unit recording in moving animals, Physiology & Behavior, 9(4):671-4 (1972).
David, S. and Lacroix, S., Molecular Approaches to Spinal Cord Repair, Annual Review of Neuroscience, 26(1):411-40 (2003).
Fayad, G and Elmiyeh, B., Cochlear Implant, Artificial Organs, Hakim NS, editor. London: Springer London; 133-6 (2009).
Hess, A.E. et al, Development of a stimuli-responsive polymer nanocomposite toward biologically optimized, MEMS-based neural probes, J. Micromech. Microeng., 21(5):054009 (2011).
Hosseini, N.H. et al., Comparative Study on the Insertion Behavior of Cerebral Microprobes, Engineering in Medicine and Biology Society, 29th Annual International Conference of the IEEE, pp. 4711-4714 (2007).
Huang, W. et al, Regenerative potential of silk conduits in repair of peripheral nerve injury in adult rats. Biomaterials, 33(1):59-71 (2012).
Kato, Y. et al., Preliminary Study of Multichannel Flexible Neural Probes Coated with Hybrid Biodegradable Polymer, Engineering in Medicine and Biology Society, 8th Annual International Conference of the IEEE., pp. 660-663 (2006).
Kim, D-H. and Martin, D.C., Sustained release of dexamethasone from hydrophilic matrices using PLGA nanoparticles for neural drug delivery, Biomaterials, 27(15):3031-7 (2006).

(56) References Cited

OTHER PUBLICATIONS

Lee, H. et al., Biomechanical analysis of silicon microelectrode-induced strain in the brain, Journal of Neural Engineering, 2(4):81-9 (2005).
Lewitus D, et al, Ultrafast resorbing polymers for use as carriers for cortical neural probes, Acta. Biomaterialia, 7(6):2483-91 (2011).
Lin, Y-C et al, Spatially Controlled Delivery of Neurotrophic Factors in Silk Fibroin-Based Nerve Conduits for Peripheral Nerve Repair, Annals of Plastic Surgery, 67(2):147-55 (2011).
Lind, G. et al, Gelatine-embedded electrodes—a novel biocompatible vehicle allowing implantation of highly flexible microelectrodes, Journal of Neural Engineering, 7(4): 046005 (2010).
Madduri, S. et al, Trophically and topographically functionalized silk fibroin nerve conduits for guided peripheral nerve regeneration, Biomaterials, 31 (8):2323-34 (2010).
Mercanzini, A. et al, Demonstration of cortical recording using novel flexible polymer neural probes, Sensors and Actuators A: Physical., 143(1):90-6 (2008).
Mercanzini, A. et al., Controlled Release Drug Coatings on Flexible Neural Probes, 29th Annual International Conference of the IEEE Engineering in Medicine and Biology Society, pp. 6612-6615 (2007).
Metallo, C. et al., Flexible parylene-based microelectrode arrays for high resolution EMG recordings in freely-moving small animals, J Neurosci Methods, 195(2): 176-84 (2011).
O'Brien, D. et al., Flexible microelectrode arrays with integrated insertion devices, 14th IEEE International Conference on Micro Electro Mechanical Systems, pp. 216-219 (2001).
Polikov, V.S. et al, In vitro model of glial scarring around neuroelectrodes chronically implanted in the CNS, Biomaterials, 27(31):5368-76 (2006).
Purcell, E.K. et al, Flavopiridol reduces the impedance of neural prostheses in vivo without affecting recording quality, Journal of Neuroscience Methods, 183(2):149-57 (2009).
Rousche, P.J. et al., Flexible polyimide-based intracortical electrode arrays with bioactive capability, Biomedical Engineering, IEEE Transactions on, 48(3):361-71 (2001).
Seymour, J.P. and Kipke, DR., Neural probe design for reduced tissue encapsulation in CNS, Biomaterials, 28(25):3594-607 (2007).
Skousen, J.L. et al, Reducing surface area while maintaining implant penetrating profile lowers the brain foreign body response to chronically implanted planar silicon microelectrode arrays, Prog. Brain Res., 194:167-80 (2011).
Stice, P. et al, Thin microelectrodes reduce GFAP expression in the implant site in rodent somatosensory cortex, Journal of Neural Engineering, 4(2):42-53 (2007).
Suzuki, T. et al., A 3D flexible parylene probe array for multichannel neural recording, Neural Engineering Conference Proceedings, First International IEEE EMBS Conference, pp. 154-156 (2003).
Takeuchi, S. et al. Parylene flexible neural probes integrated with microfluidic channels, Lab Chip., 5(5):519-23 (2005).
Venkatraman, S, et al., A System for Neural Recording and Closed-Loop Intracortical Microstimulation in Awake Rodents, IEEE Transactions on Biomedical Engineering, 56(1):15-2 (2009).
Wester, B.A. et al., Development and characterization of in vivo flexible electrodes compatible with large tissue displacements, J. Neural Eng., 6(2):024002 (2009).
Yang, Y, et al. Repair of Rat Sciatic Nerve Gap by a Silk Fibroin-Based Scaffold Added with Bone Marrow Mesenchymal Stem Cells, Tissue Engineering Part A, 17(17-18):2231-44 (2011).
Zhang, F. et al., Electrospun Silk Fibroin Nanofiber Tubes for Peripheral Nerve Regeneration, 4th International Conference on Bioinformatics and Biomedical Engineering (iCBBE), pp. 1-4 (2010).
Zhong, Y, et al., A Novel Dexamethasone-releasing, Anti-inflammatory Coating for Neural Implants, Conferences Proceedings 2nd International IEEE EMBS Conference on Neural Engineering, pp. 522-525 (2005).
Zhong, Y. and Bellamkonda, R.V., Controlled release of anti-inflammatory agent a-MSH from neural implants, Journal of Controlled Release, 106(3):309-18 (2005).

Andersen, R.A., et al, Cognitive Neural Prosthetics, Annu Rev Psychol., 61:169-C3 (2010).
Azemi, E. et al, The surface immobilization of the neural adhesion molecule LI on neural probes and its effect on neuronal density and gliosis at the probe/tissue interface, Biomaterials, 32(3):681-92 (2011).
Batzer, M.A. et al., Enhanced evolutionary PCR using oligonucleotides with inosine at the 3'-terminus, Nucleic Acid Res., 19:5081 (1991).
Benfenati, V. et al, A silk platform that enables electrophysiology and targeted drug delivery in brain astroglial cells, Biomaterials, 31(31):7883-91 (2010).
Chothia, C. and Lesk, A.M., Canonical structures for the hypervariable regions of immunoglobulins, J. Mol. Biol., 196:901-917 (1987).
Cullen, D.K. et al., Strain rate-dependent induction of reactive astrogliosis and cell death in three-dimensional neuronal-astrocytic cocultures, Brain Research, 1158(0):103-15 (2007).
Ghaznavi, A.M. et al, Silk Fibroin Conduits, Annals of Plastic Surgery, 66(3):273-9 (2011).
Guziewicz, N., et al., Lyophilized silk fibroin hydrogels for the sustained local delivery of therapeutic monoclonal antibodies, Biomaterials, 32(10):2642-50 (2011).
Harris JP, et al. In vivo deployment of mechanically adaptive nanocomposites for intracortical microelectrodes, J. Neural Eng., 8(4):046010 (2011).
Harris, J.P. et al, Mechanically adaptive intracortical implants improve the proximity of neuronal cell bodies, Journal of Neural Engineering, 8:066011 (2011).
Heath, C. A., Cells for tissue engineering, Trends in Biotechnology, 18: 17-19 (2000).
Hollinger, P. et al, "Diabodies": small bivalent and bispecific antibody fragments, Proc. Natl. Acad. Sd. USA, P0:6444-6448 (1993).
Jiang, C, et al. Mechanical Properties of Robust Ultrathin Silk Fibroin Films, Advanced Functional Materials, 17(13):2229-37 (2007).
Kim, D. H., et al Silicon electronics on silk as a path to resorbable implantable devices, Applied Physics Letters, 95(13)133701 (2009).
Lawrence, B.D. et al, Effect of Hydration on Silk Film Material Properties, Macromolecular Bioscience, 10(4):393-403 (2010).
Leach, J.B. et al., Bridging the Divide between Neuroprosthetic Design, Tissue Engineering and Neurobiology, Frontiers in Neuroengineering, 2: 18 (2010).
Li, M., et al, Study on porous silk fibroin materials. II. Preparation and characteristics of spongy porous silk fibroin materials, J. Appl. Poly Sci., 79, 2192-2199 (2001).
Lovett, M. et al. Gel spinning of silk tubes for tissue engineering, Biomaterials, 29(35):4650-4657 (2008).
Lu, Q., et al, Stabilization and release of enzymes from silk films, Macromolecular Bioscience, 10(4):359-368 (2010).
Lucas, F. et al., The silk fibroins, Advanced Protein Chemistry, 13:107-242 (1958).
Meinel, L. et al. The inflammatory responses to silk films in vitro and in vivo. Biomaterials, 26(2): 14 7-55 (2005).
Min, S., et al. Preparation and Characterization of Porous Silk Fibroin Gel, Sen'l Gakkaishi 54(2): 85-92 (1997).
Murphy, AR. et al., Modification of silk using diazonium coupling chemistry and the effects on hMSC proliferation and differentiation, Biomaterials, 29:2829-2838 (2008).
Ohtsuka, E. et al., An alternative approach to deoxyoligonucleotides as hybridization probes by insertion of deoxyinosine at ambiguous codon positions, J. Biol. Chem., 260:2605-2608 (1985).
Polikov, V.S. et al, Control protocol for robust in vitro glial scar formation around microwires: Essential roles of bFGF and serum in gliosis, Journal of Neuroscience Methods, 181(2)170-7 (2009).
Pritchard, E. M., Incorporation of proteinase inhibitors into silk-based delivery devices for enhanced control of degradation and drug release, Biomaterials 32(3): 909-918 (2011).
Rajkhowa, R., et al, Reinforcing silk scaffolds with silk particles, Macromolecular, Bioscience, 10(6): 599-611 (2010).
Rockwood, D. N. et al, Materials fabrication from Bombyx mori silk fibroin, Nat. Protocols, 6(10):1612-31 (2011).

(56) References Cited

OTHER PUBLICATIONS

Rossolini, G.M. et al., Use of deoxyinosine-containing primers vs degenerate primers for polymerase chain reaction based on ambiguous sequence information, Mol. Cell. Probes, 8:91-98 (1994).

Subbaroyan J. et al., A finite-element model of the mechanical effects of implantable microelectrodes in the cerebral cortex, Journal of Neural Engineering, 2(4)103-13 (2005).

Szarowski, D.H. et al, Brain responses to micro-machined silicon devices, Brain Research, 5;983(1-2):23-35 (2003).

Szybala, C. et al, Antiepileptic effects of silk-polymer based adenosine release in kindled rats, Experimental Neurology, 219(1):126-35 (2009).

Takahashi, K. et. al., Induction of pluripotent stem cells from adult human fibroblasts by defined factors, Cell, 131, 861-872 (2007).

Tao, H. et al. Gold nanoparticle-doped biocompatible silk films as a path to implantable thermo-electrically wireless powering devices, Appl. Phys. Lett., 97:123702 (2010).

Thelin, J, et al. Implant Size and Fixation Mode Strongly Influence Tissue Reactions in the CNS, PLoS ONE, 6(1):e16267 (2011).

Wang, X. et al, Nanolayer biomaterial coatings of silk fibroin for controlled release, J. Controlled Release, 121(3)190-199 (2007).

Wang, X. et al, Silk microspheres for encapsulation and controlled release, J. Controlled Release, 117:360-370 (2007).

Wang, X. et al. Controlled release from multilayer silk biomaterial coatings to modulate vascular cell responses, Biomaterials 29(7):894-903 (2008).

Wilz, A. et al., Silk polymer-based adenosine release: therapeutic potential for epilepsy, Biomaterials, 29:3609-3616 (2008).

Wittmer, C.R. et al , Multifunctionalized Electrospun Silk Fibers Promote Axon Regeneration in the Central Nervous System, Advanced Functional Materials, 21(22):4232-42 (2011).

Xia, Y. and Whitesides, G.M, Soft Lithography, Angewandte Chemie International Edition, 37(5):550-75 (1998).

Yu, J. et al, Induced pluripotent stem cell lines derived from human somatic cells, Science, 318( 5858): 1917-1920 (2007).

Zapata, G. et al., Engineering linear F(ab')2 fragments for efficient production in *Escherichia coli* and enhanced antiproliferative activity, Protein Eng., 8(10):1057-1062 (1995).

Zhong, Y. and Bellamkonda, R.V., Dexamethasone-coated neural probes elicit attenuated inflammatory response and neuronal loss compared to uncoated neural probes, Brain Research, 1148:15-27 (2007).

\* cited by examiner

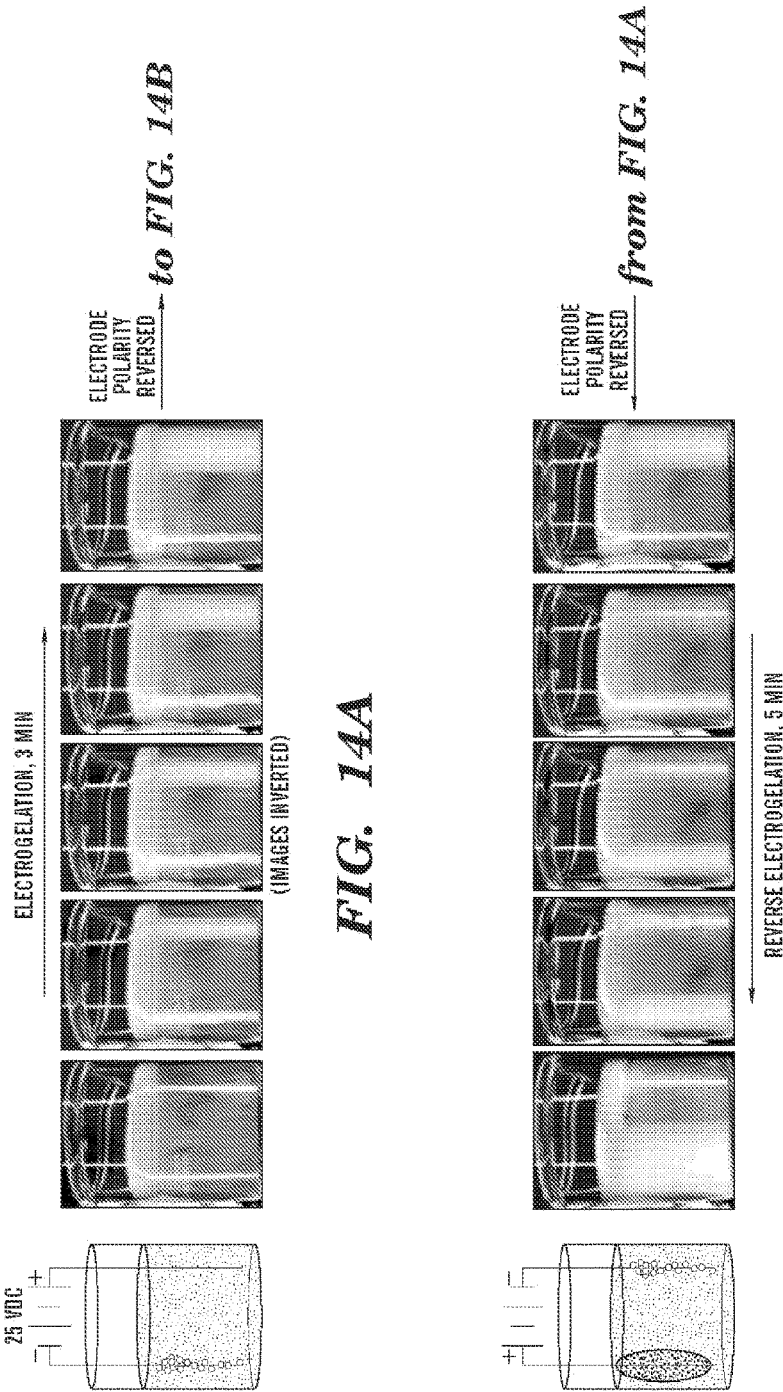

DYNAMIC SILK COATINGS FOR IMPLANTABLE DEVICES

CROSS-REFERENCE TO RELATED APPLICATIONS

This application is a 35 U.S.C. § 371 National Phase Entry Application of International Application No. PCT/US2012/034490 filed Apr. 20, 2012, which designates the U.S., and which claims benefit under 35 U.S.C. § 119(e) of the U.S. Provisional Application No. 61/477,484, filed Apr. 20, 2011, the contents of each of which are incorporated herein by reference in their entireties.

GOVERNMENT SUPPORT

This invention was made with government support under grant No. EB002520 awarded by the National Institutes of Health. The government has certain rights in the invention.

FIELD OF THE DISCLOSURE

Provided herein relates to silk-based implantable systems and devices and methods of preparing the same. In some embodiments, the silk-based implantable systems and devices can be adapted for use as neuroprosthetic devices such as brain electrodes, shunts and/or spinal cord nerve guide wires.

BACKGROUND OF THE DISCLOSURE

Neuroprosthetic devices hold promise for future biomedical human-machine interactions. Various applications of this technology are actively being explored, ranging from direct neural control of prosthetic limbs to augmentation of sensory inputs. See, e.g., Andersen R A., et al. "Cognitive Neural Prosthetics." Annu Rev Psychol. 2010; 61:169-C3; Venkatraman S, et al. "A System for Neural Recording and Closed-Loop Intracortical Microstimulation in Awake Rodents." IEEE Transactions on Biomedical Engineering. 2009 January; 56(1):15-22. Indeed, first generation neuroprosthetics, such as cochlear implants, have already been used in the clinic (Fayad G and Elmiyeh B. "Cochlear Implant." In: Hakim N S, editor. Artificial Organs. London: Springer London; 2009; p. 133-6). Despite this success, the long-term reliability of chronic cortical electrode implants remains a major obstacle to the widespread adaptation of neuroprosthetic technologies to the clinic, with many penetrating arrays losing the ability to record neurons after just weeks or months.

This lack of chronic reliability is often attributed to gliosis, the inflammatory response in the central nervous system. Gliosis is characterized by the formation of a glial scar around the implanted electrode in an attempt by the body to wall off the injury site from healthy tissue. A dense accumulation of microglia, macrophages, and reactive astrocytes produce extracellular matrix molecules that inhibit axonal growth within the scar. This encapsulation effectively increases the electrical impedance at the recording site, while also acting as a physical barrier between the electrode and the targeted neuronal populations. As the glial scar grows, the electrode becomes incapable of recording extracellular action potentials.

Bioelectrodes for neural recording and neurostimulation are an integral component of a number of neuroprosthetic devices, including commercially available cochlear implants and developmental devices, such as bionic eyes and brain-machine interfaces. Deep brain stimulation (DBS) is an established therapy for the treatment of Parkinson's disease (PD) and shows promise for the treatment of several other disorders, where it is essential to have a spatially precise contact between the electrode and tissue. Current rigid metal-based electrodes can acquire signals over a few days to weeks. However, continuing to extract signals with a high fidelity over long periods of time remains a major challenge. Presently, issues regarding electrode fracture and signal drop-out plague metal-based micro-electrodes for long-term use. Rigid metal needles do not comply mechanically with brain tissue, shifting during normal head movement, resulting in electrode misplacement from the target neural tissue area and electrode breaks.

The large mismatch between the elastic modulus of brain tissue and conventional silicon-based electrode shanks has been implicated as a significant factor contributing to chronic gliosis. Finite element analysis techniques have been used to model the large stress concentrations and "micromotion" effect that occur at the brain-electrode interface in response to indwelling, inelastic materials (Subbaroyan J. et al., "A finite-element model of the mechanical effects of implantable microelectrodes in the cerebral cortex." Journal of Neural Engineering. 2005 Dec. 1; 2(4):103-13; Lee H, Bellamkonda R V. et al., "Biomechanical analysis of silicon microelectrode-induced strain in the brain." Journal of Neural Engineering. 2005 Dec. 1; 2(4):81-9). Electrode micromotion resulting from a mismatch in stiffness between the electrode and the brain tissue leading to chronic inflammation and associated increased glial activation, and movement of the electrode from the target, resulting in inconsistent readings. Mechanical stress has been shown to stimulate astrocyte reactivity and neuronal death in vitro (Cullen D K et al., "Strain rate-dependent induction of reactive astrogliosis and cell death in three-dimensional neuronal-astrocytic co-cultures." Brain Research. 2007 Jul. 16; 1158(0):103-15), and in vivo studies have reported increased scarring around electrodes tethered to the skull, which are mechanically less compliant than free-floating probes (Thelin J, et al. "Implant Size and Fixation Mode Strongly Influence Tissue Reactions in the CNS." PLoS ONE. 2011 Jan. 26; 6(1):e16267; Biran R. et al., "The brain tissue response to implanted silicon microelectrode arrays is increased when the device is tethered to the skull." J Biomed Mater Res A. 2007 July; 82(1):169-78). A recent in vivo report compared the tissue response to stiff and compliant probes with the same surface chemistry, finding the compliant probes reduced glial scar intensity, with a greater density of nearby neurons compared to the stiff shanks at 4 weeks (Harris J P, et al. "Mechanically adaptive intracortical implants improve the proximity of neuronal cell bodies. Journal of Neural Engineering." 2011 Oct. 1; 8:066011).

One approach to minimize electrode micromotion and associated glial scarring, and/or to provide strain relief at the electrode-issue interface is to use flexible, thin-film probes fabricated from polymers such as polyimide or parylene. See, e.g., Rousche P J, et al., "Flexible polyimide-based intracortical electrode arrays with bioactive capability." Biomedical Engineering, IEEE Transactions on. 2001; 48(3): 361-71; Mercanzini A, et al. "Demonstration of cortical recording using novel flexible polymer neural probes." Sensors and Actuators A: Physical. 2008 May 2; 143(1):90-6; Hess A E, et al. "Development of a stimuli-responsive polymer nanocomposite toward biologically optimized, MEMS-based neural probes." J. Micromech. Microeng. 2011 May; 21(5):054009; Kato Y. et al., "Preliminary Study of Multichannel Flexible Neural Probes Coated with Hybrid Biodegradable Polymer." In: Engineering in Medicine and Biology Society, 2006. EMBS '06. 28th Annual International Conference of the IEEE. 2006. p. 660-3; Takeuchi S. et al. "Parylene flexible neural probes integrated with microfluidic channels." Lab Chip. 2005 May; 5(5):519-23; Suzuki T, et al., "A 3D flexible parylene probe array for multichannel neural recording." In: Neural Engineering, 2003. Conference Proceedings. First International IEEE EMBS Conference. 2003. p. 154-6; Wester B A, et al., "Development and characterization of in vivo flexible electrodes compatible with large tissue displacements." J. Neural Eng. 2009 April; 6(2):024002; and Seymour J P and Kipke D R. "Neural probe design for reduced tissue encapsulation in CNS." Biomaterials. 2007 September; 28(25):3594-607. Such flexible probes introduce an additional challenge, however, as these devices can be incapable of penetrating the pia to achieve precise insertion into the brain without buckling.

Further, the neural recording interface remains another major challenge. Erosion of connections between the abiotic and biotic niches results in loss of function of electrodes and implants. This is an endemic problem in biology and one that has resisted traditional approaches for resolution. As a result, implants for recording electronics have relatively short lifetimes, requiring constant replacement, leading to associated failure modes due to the device itself or repeated surgical intervention that damages surrounding tissue.

Since most electrode implants remain relatively rigid and damaging upon insertion, the interface between current systems and the dynamic nature of biological systems tend to be a major source of problems. The dynamic issues include the biochemistry at the site (cell signaling factors, ECM deposition), cell dynamics at the site (e.g., astroglial and other nerve cells that respond to and with the implants), and stress shielding (e.g., mechanical mismatch between electrodes and soft brain tissue, leading to failure modes, fibrous encapsulation and related complications and failures to maintain a stable interface). Further, a related underlying problem includes the limited ability to establish a conformal and tight interface, due to the mechanical mismatch, between the existing materials and the soft and convoluted brain and neurological tissues. Therefore, there is a need to develop technologies and/or devices that can overcome one or more of the above limitations.

SUMMARY

The neural recoding interface remains a major challenge. While flexible electrodes are desired to be used for their better compliance with a brain tissue, these flexible electrodes are not stiff enough to penetrate into a brain tissue. Further, erosion of connections between the abiotic and biotic niches results in a loss of function of electrodes and implants. As a result, implants (e.g., for recoding electronics) have relatively short lifetimes, thus requiring constant replacement and leading to associated failure modes due to the device itself or repeated surgical intervention that damages surrounding tissue. Thus, there is a need for developing implantable devices and/or systems with sufficient mechanical stiffness for insertion into a brain tissue without compromising the mechanical compliance with a brain tissue after insertion. Provided herein generally relates to dynamic silk coatings for implantable devices, wherein the silk coating can be applied onto an implantable flexible device before implantation, as a means to provide the flexible device with mechanical strength, which will soften upon implantation, and/or the silk coating can be renewably formed in situ on a surface (e.g., a conducting surface) of the implantable device post-implantation, e.g., to minimize bio-fouling.

Accordingly, one aspect provided herein relates to a silk-based implantable system comprising an electrical component, wherein at least a portion of the electrical component is in contact with a silk matrix, the silk matrix providing the electrical component with sufficient stiffness to penetrate a target tissue and becoming compliant upon the penetration.

In some embodiments, the electrical component can be at least part of a pre-formed or a conventional implantable device that would generally deform during the penetration in the absence of the silk matrix. Accordingly, in such embodiments, coating the preformed or conventional implantable device can provide it with mechanical stiffness sufficient to penetrate into a target tissue (e.g., without deformation such as buckling or bending). Upon penetration, the silk coating can become softer, thus allowing the implantable device to be mechanically compliant with the target tissue.

A preformed or conventional implantable device can be an implantable device for any part of the body in a subject including, but are not limited to, subcutaneous, intramuscular, intraperitoneal, cardiac, pulmonary, and neural tissue. In some embodiments. The pre-formed or conventional implantable device can be a neuroprosthetic device. Exemplary neuroprosthetic device can include, but are not limited to, a brain penetrating electrode, a shunt, a nerve guide, a cochlear implant, and a microelectrode array.

While the electrical component can be an integral part of a pre-formed or conventional implantable device, the electrical component can also be directly or indirectly patterned on the silk matrix to form the silk-based implantable device.

The electrical component can be formed from any conventional materials commonly used for electronics in an implantable device, e.g., without limitations, silicon, gold, platinum, titanium, and any combinations thereof. Alternatively, the electrical component can include biodegradable electronics, e.g., made from biodegradable or erodible organic semiconductors such as melanins and carotenoids. In one embodiment, the electrical component can include a silk-based electrode as described herein.

In accordance with various aspects described herein, the silk matrix is dynamic with respect to its changes in the mechanical property before or during and after penetration (or between a dry state and a hydrated state). Before penetration and during at least part of the penetration process, the silk matrix is stiff enough to enable the implantable device to penetrate into a target tissue (e.g., without deformation such as buckling or bending). In some embodiments, the silk matrix can increase a buckling force of the electrical component or the implantable device by at least about 2-fold, at least about 5-fold, at least about 10-fold or more, as compared to the absence of the silk matrix. In some embodiments, the silk matrix can increase a buckling force of the electrical component or the implantable device by at least about 1 order of magnitude (e.g., about 10-fold or more), about 2 orders of magnitude (e.g., about 100-fold or more), about 3 orders of magnitude (e.g., about 1000-fold or more) or more, as compared to the absence of the silk matrix.

Upon penetration into the target tissue, the silk matrix in contact with the electrical component can become compliant upon the penetration, e.g., by hydration of the silk matrix. Such mechanical compliance of the silk matrix with surrounding tissue upon penetration can provide conformal contact between the electrical component and a surface of the target tissue.

In some embodiments, at least one side of the electrical component can be coated with the silk matrix. Thus, at least part of the electoral component can still be exposed to surrounding tissue, e.g., for detecting a signal. Without wishing to be bound, the electrical component can also be encapsulated in the silk matrix. In such embodiments, the silk matrix can be modified or doped to become a conductive material.

In some embodiments, the silk matrix can reduce scar formation (e.g., gliosis) around the electrical component or the implantable device by at least about 10%, as compared to the absence of the silk matrix.

Silk matrix can stabilize an active agent including a therapeutic agent for an extended release in vivo. Accordingly, in some embodiments, the silk matrix can comprise an active agent including, but not limited to, a therapeutic agent. The active agent (including a therapeutic agent) can include, e.g., but are not limited to, an agent that promotes tissue growth, controls inflammation, and/or reduces scar formation around the implanted system or device. In one embodiment, the active agent can include a gliosis-modulating agent.

Depending on applications of the implantable device and/or mechanical property of implantation sites, the silk matrix can have a thickness of about 1 µm to about 1000 µm. The total thickness of the silk matrix can be resulted from a single layer or a plurality of silk layers, each of which can have the same or different thickness and optionally the same or different active agent.

Applications of the silk-based implantable systems are also provided herein. For example, a method of inserting a flexible or soft implantable device into a target tissue comprises providing a silk-based implantable system described herein, wherein the silk-based implantable system comprises the flexible or soft implantable device at least partially coated with a silk matrix in its dry-state. In some embodiments, the silk-based implantable systems can be used to reduce scar formation (e.g., gliosis) around the implantable device (e.g., neuroprosthetic device) implanted in a tissue (e.g., a brain tissue). In some embodiments, the silk-based implantable systems can be used to improve long-term functionality of an implantable device (e.g., a neuroprosthetic device) implanted in a tissue (e.g., a brain tissue).

Another aspect described herein relates to a silk-based implantable device comprising a silk body with at least one electrically-conducting component. In some embodiments, the silk-based implantable device can be constructed to be capable of renewably forming a silk coating on a surface of the implantable device. Such silk-based implantable device can minimize biofouling, thus increasing the reliability and lifetime of the implantable device in vivo.

For example, in some embodiments, the silk body can include a silk reservoir of any shape with at least one electrically-conducting component formed on a least a portion of a surface of the silk reservoir (e.g., the surface that is in contact with a fluid upon implantation). In some embodiments where the silk-based implantable device are adapted for use as an electrode, the silk reservoir can be a silk tube with at least one electrically-conducting component formed on at least a portion of a lateral surface of the silk tube. The silk reservoir or silk tube can be filled with a silk solution.

In alternative embodiments, the silk body can comprise a first silk layer and a second silk layer, wherein at least one of the first and the second silk layer can comprise at least one electrically-conducting component formed on at least a portion of a surface of the silk layer. In some embodiments, between the first and the second silk layers can include solid-state silk that can be solubilized to form a silk solution upon contact with a fluid, e.g., silk particles (including lyophilized silk particles), silk powder (including lyophilized silk powder), or a silk film.

To allow the silk solution to form a coating on a surface of the electrically-conducting component, in some embodiments, the electrically-conducting component can include one or more through holes such that the silk solution present in the silk reservoir (e.g., silk tube) between the silk layers can be discharged onto the surface of the electrically-conducting component to be coated. The solution can be discharged onto the surface of the electrically-conducting component to be coated by any methods known in the art, including, but not limited to, diffusion, an implantable pump, and/or an external pump. The silk solution discharged onto the surface of the electrically-conducting component can form a gel-like coating upon application of a first voltage through the electrically-conducting component. In some embodiments, the gel-like coating can be removed, e.g., by transforming the gel-like coating to a solution upon application of a second voltage with a polarity opposite to the first voltage.

The electrical conducting component can include any material that is commonly used as electronics for implantable devices, and/or an electrically-conductive material. In some embodiments, the electrical conducting component can include a metal such as a transition metal (e.g., silicon), a noble metal (e.g., gold), or a combination thereof. I In some embodiments, the electrical conducting component can include a biodegradable component that can conduct electricity such as biodegradable organic semiconductors (e.g., melanins and/or carotenoids).

In some embodiments, the electrical conducting component can include silk modified to conduct electricity. For example, the silk can be functionalized by modifying a tyrosine of the silk protein to a sulfate group followed by polymerization of the modified tyrosine with a conducting polymer. Alternatively, the silk can be doped with a conductive material including, but not limited to, gold nanoparticles, carbon nanotubes, graphene, and a conducting polymer. Non-limiting examples of a conducting polymer can include polyethylenedioxythiophene (PEDOT), polypyrrole-based conductive polymer, copolymers of thiophenes and polypyrroles, copolymers of poly-lactide and polyaniline, or any combinations thereof.

In some embodiments, the silk-based implantable device can be adapted for use as an implantable brain penetrating electrode. For example, the silk body can be in a form of a silk tube with a diameter of less than 2 mm. In some embodiments, the silk-based electrode can have a tensile strength of at least about 2 MPa when the silk body is in a dry state. In some embodiments, the silk-based electrode can have a shear modulus of less than about 200 kPa upon contact of the silk body with a fluid (e.g., interstitial fluid and/or body fluid such as cerebrospinal fluid).

In some embodiments, the silk body can comprise an active agent including a therapeutic agent.

Methods for regenerating a silk coating on a surface of a device are also provided herein. In some embodiments, the method comprises providing the silk-based device described herein, wherein the silk solution discharged onto the surface of the electrically-conducting component can form a gel coating upon application of a first voltage through the electrically-conducting component, and can optionally turn to a solution upon application of a second voltage with a polarity opposite to the first voltage.

The capability of renewing or regenerating the silk coating on a surface of a device can reduce biofouling. Accordingly, a method of reducing biofouling of a device is provided herein. The method comprises providing the silk-based device described herein, wherein the silk solution discharged onto the surface of the electrically-conducting component forms a gel coating upon application of a first voltage through the electrically-conducting component, and can optionally turn to a solution upon application of a second voltage with a polarity opposite to the first voltage. The first voltage and/or the second voltage can be applied to the electrically-conducting component at any potential, provided that the voltage potential is high enough for silk gelation. In some embodiments, the first voltage and the second voltage can be at least about 1.2V. In other embodiments, the first voltage and the second voltage can be about 5 V to about 50 V.

In some embodiments, the device is placed in vivo or in situ. Thus, methods described herein can be carried out in vivo or in situ.

BRIEF DESCRIPTION OF THE DRAWINGS

FIGS. 1A and 1B are representative images of GFAP staining around uncoated and silk-coated steel microwires, respectively. FIGS. 1C and 1D are representative images of CS staining around uncoated and silk-coated steel microwires, respectively. FIGS. 1E and 1F are representative images of GFAP staining around a steel microwire dipped in 25 mg/mL cytarabine (Ara-C) in $H_2O$ and a silk solution containing 25 mg/mL Ara-C, respectively. FIGS. 1G and 1H are representative images of CS staining around a steel microwire dipped in 25 mg/mL cytarabine (Ara-C) in $H_2O$ and a silk solution containing 25 mg/mL Ara-C, respectively. Microwire diameter=50 μm.

FIG. 5A shows that uncoated wire cannot penetrate Parafilm membrane. FIG. 5B shows that silk-coated wire penetrates Parafilm without buckling. FIG. 5C shows that after 30 seconds hydration, the silk-coated wire becomes compliant, and cannot penetrate Parafilm.

FIG. 6A shows a dip-coating method. FIG. 6B shows a single-step casting. FIG. 6C shows a two-step casting.

FIG. 12A is a schematic diagram of a silk electrode with a reservoir for silk solution. FIG. 12B is a schematic diagram of a silk electrode designed for regenerating a silk coating using lyophilized silk powder.

FIG. 13A is an image showing diameter measurement of a needle-like silk matrix. FIG. 13B is an image of a needle-like silk matrix with a sharpened tip. FIG. 13C is an image showing diameter measurement of silk implantable electrodes with different diameters. FIG. 13D is an image showing a silk implantable electrode as a foam-like silk construct with embedded motor wire conductor (top) and sharpened for enhanced puncturing ability (bottom).

FIGS. 14A-14B show a silk electrogelation (e-gel) process applied to an 8 wt % silk aqueous solution with 25 VDC using mechanical pencil lead electrodes. FIG. 14A shows that over 3 minutes the gel forms around the positive electrode with gas evolution at both electrodes. FIG. 14B shows that gelation is reversed with the application of reversed polarity DC voltage.

FIGS. 15A and 15B show dynamic shear frequency and strain sweeps, respectively, collected from silk solutions prior and post processing. In both FIGS. 15A and 15B, 25 VDC voltage was applied to 2 mL of 8.4 wt % silk solution for 10 min using platinum wires for e-gel formation. For the pH-gel, 8.4 wt % silk solution (pH 6.5) was treated by a strong acid (1 M HCl) to adjust the final proton concentration due to the acid to 0.01 M (pH~4.4). Solid symbols in FIG. 15B show the strain response of e-gels and silk solutions after application of high amplitude shear. FIG. 15C show engineering stress-strain curves obtained from the silk solution and e-gel by transient tensile testing of adhesion on the stainless steel surfaces of the DMA. Inset shows the initial linear region of the engineering stress-strain curves. FIG. 15D is a photograph of the e-gel at intermediate strains during transient testing displaying adhesive properties.

FIG. 17A is a schematic diagram of silk microspheres imbedded in silk sponge rods (0.8 mm diameter, 4 mm length) coated with additional drug-loaded films and implanted at site of epileptic focus in a kindling rodent model. FIG. 17B shows a histological section of silk implant after one month in the brain. FIG. 17C is a plot showing in vitro release kinetics of adenosine from the silk implants. FIG. 17D is a plot showing seizure suppression (indicated by an arrow) through 13 stimulations/6 days in vivo.

FIG. 18A shows casting and drying of silk fibroin solution on a temporary substrate of PDMS; 5-15 μm thick silk film after drying for 12 hours at room temperature. FIG. 18B shows steps for fabricating the electrode arrays, transfer printing them onto silk, and connecting to anisotropic conductive film (ACF) cable. FIG. 18C shows schematic illustration of clinical usage of a representative device in an ultrathin mesh geometry with dissolvable silk support.

FIG. 19A shows schematic illustration of trends in thickness and structure that improve conformal contact. FIG. 19B shows a series of pictures illustrating how the thickness of the electrode array contributes to conformal contact on a brain model. FIG. 19C show magnified view of the pictures from FIG. 19B. FIG. 19D is an image of an electrode array with a mesh design on dissolvable silk substrate. Arrows indicate struts in the mesh that help to stabilize the Au interconnects after dissolution of the silk. The inset illustrates the high degree of conformal contact that can be achieved on the brain model once the silk substrate has been dissolved.

FIG. 21A indicates stabilization data for lipase in silk films. FIG. 21B indicates stabilization data for peroxidase in silk films.

DETAILED DESCRIPTION

Figure 1A:
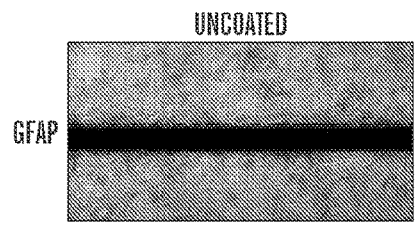
FIGS. 1A-1H are representative images of glial fibrillary acid protein (GFAP) or chondroitin sulfate (CS) staining around different treated steel microwires in an in vitro glial scarring model.

While flexible electrodes are desirable for implantation due to their better compliance with a brain tissue, these flexible electrodes are generally not stiff enough to penetrate into a brain tissue. Further, implants (e.g., for recoding electronics) have relatively short lifetimes, partly due to erosion of connections between the abiotic and biotic niches. Thus, the reliability of chronic flexible electrodes (e.g., chronic brain penetrating electrodes for neural recording) needs to be improved in order for the technology to be viable in clinical applications. One approach is to improve implantable devices and/or systems with sufficient mechanical stiffness for insertion into a brain tissue without compromising the mechanical compliance of a flexible implant with a brain tissue after insertion, and to reduce the inflammatory response at the probe-tissue interface. Provided herein generally relates to dynamic silk coatings for implantable devices, wherein the silk coating can be applied onto an implantable flexible device before implantation, as a means to provide the flexible device with mechanical strength, which will soften upon implantation, and/or the silk coating can be renewably formed in situ on a surface (e.g., a conducting surface) of the implantable device post-implantation, e.g., to minimize bio-fouling.

Silk-Based Implantable Systems and Methods of Making the Same

The next generation of neuroprosthetic devices can rely on chronically implanted arrays of small electrodes targeting specific neuronal clusters within the brain. The existing cortical electrodes generally consist of stiff spikes of metal or silicon, and have been shown inadequate for chronic neural sensing due to both a slow degradation of signal over time as well as inconsistent targeting of neurons. Two major factors that can contribute to the lack of chronic electrode reliability include (1) glial scar formation around the electrode leading to signal degradation, e.g., from increased impedance and/or neuronal re-arrangement and death; and (2) electrode micromotion resulting from the mismatch in stiffness between the electrode and the brain leading to, e.g., chronic inflammation and thus increased glial activation, and/or movement of the electrode from the target, thus giving consistent readings. See, e.g., Polikov V. S. et al., "Response of brain tissue to chronically implanted neural electrodes," Journal of Neuroscience Methods, vol. 148, no. 1, pp. 1-18, October 2005; and Leach J. B. et al., "Bridging the Divide between Neuroprosthetic Design, Tissue Engineering and Neurobiology," Frontiers in Neuroengineering, vol. 2, p. 18, 2010.

To address the issue of electrode micromotion, flexible electrodes have been suggested as an alternative to stiff designs. However, one challenge with such flexible electrodes is achieving insertion into the brain without buckling. Various insertion techniques have been reported, including placement with a removable needle (D. O'Brien, T. Nichols, and M. Allen, "Flexible microelectrode arrays with integrated insertion devices," in Micro Electro Mechanical Systems, 2001. MEMS 2001. The 14th IEEE International Conference on, pp. 216-219, 2001), or encapsulation with a stiff, biodegradable substrate such as PEG (T. Suzuki, K. Mabuchi, and S. Takeuchi, "A 3D flexible parylene probe array for multichannel neural recording," in Neural Engineering, 2003. Conference Proceedings. First International IEEE EMBS Conference on, pp. 154-156, 2003; and S. Takeuchi, D. Ziegler, Y. Yoshida, K. Mabuchi, and T. Suzuki, "Parylene flexible neural probes integrated with microfluidic channels," Lab on a Chip, vol. 5, no. 5, pp. 519-523, May 2005) or gelatin (G. Lind, C. E. Linsmeier, J. Thelin, and J. Schouenborg, "Gelatine-embedded electrodes—a novel biocompatible vehicle allowing implantation of highly flexible microelectrodes," Journal of Neural Engineering, vol. 7, no. 4, p. 046005, August 2010). Using such biodegradable substrate can provide the ability to deliver bioactive compounds such as anti-inflammatory agents to reduce glial scarring, or neuronal stimulants such as NGF. See, e.g., Y. Kato, I. Saito, T. Hoshino, T. Suzuki, and K. Mabuchi, "Preliminary Study of Multichannel Flexible Neural Probes Coated with Hybrid Biodegradable Polymer," in Engineering in Medicine and Biology Society, 2006. EMBS '06. 28th Annual International Conference of the IEEE, pp. 660-663, 2006.

However, such combinatorial approach, which allows for a stiff to flexible transition in mechanics, as well as long-term drug release, for increasing the long-term reliability of penetrating electrodes (e.g., reducing local glial scarring while promoting neuron survival) requires the development of more advanced electrode substrates. Many of the materials that have been reported to provide dynamic mechanical properties are not well suited for sustained local release of therapeutics. For example, stiffening materials prepared via evaporation of chemical solvents (9, 21) can preclude the incorporation and release of sensitive molecules such as enzymes and growth factors. In addition, most of the previously-reported coating materials can dissolve within minutes after hydration (14, 15, 18-20), making it impossible to achieve sustained drug release over days or weeks. Encapsulation of biodegradable, drug-loaded micro or nano spheres within the dissolvable stiffening materials has been previously reported as a means to achieve longer release (13, 25). However, the localization of the spheres at the implant-tissue interface cannot be likely sustained after the encapsulating material dissolves.

The inventors have shown that, in particular embodiments, silk fibroin can provide an improved material platform for fabricating implantable systems (e.g., implantable electrical systems such as chronic brain penetrating electrodes) that are mechanically dynamic (e.g., for placement of the implantable system to a target tissue) and capable of extended local drug release (e.g., of one or more gliosis-modulating agents). By way of example only, the silk can initially provide mechanical stability for penetration of a brain penetrating electrode, while becoming flexible after hydrating in the aqueous environment of the brain after insertion. In some embodiments, the silk can degrade over time, leaving the flexible electrodes in place. Further, the dynamic silk coatings of an implantable device can reduce inflammatory response and thus scar formation (e.g., gliosis) around the implantable device.

Accordingly, one aspect described herein relates to a silk-based implantable system comprising an electrical component, wherein at least a portion of the electrical component is in contact with a silk matrix. The properties of the silk matrix can be tailored to provide the electrical component with sufficient stiffness to penetrate a target tissue and become compliant or flexible upon the penetration. In some embodiments, such dynamic properties can be achieved by a change in hydration (e.g., water content of the silk matrix). In other embodiments, the silk can degrade to allow flexibility. If degradation is required, delivery of an active agent over an extended period can be reconciled, e.g., encapsulating the active agent in another matrix (e.g., silk particles or other polymeric particles) which is then embedded into the silk matrix.

As used herein, the term "penetration" or "penetrate" is generally meant by a silk-based implantable system or device described herein passing through at least one barrier (e.g., one or more membranes encapsulating a tissue such as brain dura and/or pia mater) and reaching a certain depth into the tissue. For example, the silk-based implantable system or device described herein can pass through at least one barrier (e.g., meninges including dura mater, arachnoid mater, and pia mater) and reach at least about 50 µm into the tissue, including at least about 100 µm, at least about 200 µm, at least about 300 µm, at least about 400 µm, at least about 500 µm, at least about 1 mm, at least about 2 mm, at least about 3 mm, at least about 4 mm, at least about 5 mm or deeper, into the tissue. In some embodiments, the silk-based implantable system or device described herein can pass through at least one barrier (e.g., meninges including dura mater, arachnoid mater, and pia mater) and reach at least about 5 mm, at least about 1 cm, at least about 2 cm, at least about 3 cm, at least about 4 cm, at least about 5 cm, at least about 6 cm, at least about 7 cm, at least about 8 cm, at least about 9 cm, at least about 10 cm or deeper, into the tissue. The terms "insert" and "penetrate" are used interchangeably herein.

As used interchangeably herein, the phrases "sufficient stiffness to penetrate a target tissue" and "stiff enough for insertion" refer to a silk-based implantable system and/or device described herein, in its dry state, having a Young's modulus at least comparable to or greater than that of a target tissue (e.g., a brain tissue) to be penetrated and/or a barrier (e.g., a protective tissue layer such as meninges) surrounding the target tissue. In some embodiments, the phrases can refer to the silk-based implantable system and/or device described herein, in its dry state, having a Young's modulus, which is at least about 5% greater (including at least about 10% greater, at least about 20% greater, at least about 30% greater, at least about 40% greater, at least about 50% greater, at least about 60% greater, at least about 70% greater, at least about 80% greater, at least about 90% or higher) than that of a target tissue (e.g., a brain tissue) to be penetrated and/or a barrier (e.g., a protective tissue layer such as meninges) surrounding thereof. For example, for penetration into a brain tissue, the silk-based implantable system and/or device can have a Young's modulus of more than 1 MPa, including, e.g., 2 MPa, 3 MPa, 4 MPa, 5 MPa, 6 MPa, 7 MPa, 8 MPa, 9 MPa, 10 MPa, 15 MPa, 20 MPa, 30 MPa, 40 MPa, 50 MPa, 60 MPa, 70 MPa, 80 MPa, 90 MPa, 100 MPa, or higher, when it is in a dry-state. In some embodiments, the silk-based implantable system and/or device can have a Young's modulus of more than 100 MPa, 250 MPa, 250 MPa, 500 MPa, 1000 MPa, 2500 MPa, 5000 MPa, 7500 MPa, 10,000 MPa, or higher, when it is in a dry-state. As used herein, the term "dry-state" refers to a silk matrix being hydrated (e.g., water content) for no more than 30%, no more than 20%, no more than 10%, no more than 5%, no more than 2.5%, no more than 1%, no more than 0.5%, no more than 0.1%, no more than 0.01%, or less. In one embodiment, the dry-state refers to 0% water content (i.e., completely dry).

In some embodiments where the silk-based implantable system and/or device is in a tubular form, e.g., a silk-based implantable electrode, the phrases "sufficient stiffness to penetrate a target tissue" and "stiff enough for insertion" can refer to a silk-based implantable system and/or device described herein having a Young's modulus sufficient to yield a buckling force greater than a force typically used to insert the silk-based implantable system and/or device into a target tissue (through a protective tissue layer). Thus, the implantable system and/or device can remain substantially straight during insertion in order to precisely reach a target region of the tissue. For example, the silk-based implantable system and/or device described herein can have a Young's modulus sufficient to yield a buckling force at least about 10% (including at least about 20%, at least about 30%, at least about 40%, at least about 50%, at least about 60%, at least about 70%, at least about 80%, at least about 90% or higher) greater than a force used to insert the silk-based implantable system and/or device into a target tissue (through a protective tissue layer). As used herein, the term "buckling force" refers to the maximum force required to cause a sudden failure of a structural member (e.g., a silk-based implantable system and/or device) subject to a compressive stress. In general, the buckling force of a structural member can be readily measured by a skilled artisan. For example, the buckling force of the silk-based implantable system and/or device can be measured by the buckling force test described in the Examples. In some embodiments, the silk matrix as described herein can increase a buckling force of the electrical component or the implantable device by at least about 2-fold, at least about 5-fold, at least about 10-fold or more, as compared to the absence of the silk matrix. In some embodiments, the silk matrix can increase a buckling force of the electrical component or the implantable device by at least about 1 order of magnitude (e.g., about 10-fold or more), about 2 orders of magnitude (e.g., about 100-fold or more), about 3 orders of magnitude (e.g., about 1000-fold or more) or more, as compared to the absence of the silk matrix.

In accordance with an aspect described herein, a silk-based implantable system comprises one or more electrical component (including two or more electrical components). As used herein, the term "electrical component" can include any component that is involved in an electric circuit, e.g., for use as a sensor, a detector, a recording device, a current/voltage generator, and/or receiver. In particular embodiments, the electrical component used herein are implantable and biocompatible in vivo. Exemplary electrical components can include, but are not limited to, an electrode or electrode contact, a transistor, a resistor, a battery, conducting wires, a signal receiver, a signal transmitter, and any combinations thereof.

In some embodiments, the electrical component can be at least part of a pre-formed or a conventional implantable device that would generally deform during the penetration in the absence of the silk matrix. Accordingly, in such embodiments, coating the preformed or conventional implantable device can provide the respective device with mechanical stiffness sufficient to penetrate into a target tissue (e.g., without deformation such as changing shape, buckling or bending). Upon penetration, the silk coating can become softer or flexible, thus allowing the implantable device to be mechanically compliant with the target tissue.

A pre-formed or conventional implantable device can be an implantable device, e.g., an implantable electrical device, designed for any use in any part of the body in a subject, including, but not limited to, subcutaneous, intramuscular, intraperitoneal, cardiac, pulmonary, and neural tissue. In some embodiments, the pre-formed or conventional implantable device (e.g., an implantable electrical device) can be a neuroprosthetic device. Exemplary neuroprosthetic device can include, but are not limited to, a brain penetrating electrode, a shunt, a nerve guide, a cochlear implant, and a microelectrode array.

In some embodiments, the implantable electrical device can include a flexible electrode (e.g., an electrode that is not mechanically stiff enough to penetrate through a protective layer into a tissue). By way of example only, flexible electrodes can be fabricated by encapsulating gold traces in parylene (See, e.g., Metallo C. et al., "Flexible parylene-based microelectrode arrays for high resolution EMG recordings in freely moving small animals," Journal of Neuroscience Methods. (2011) February 15; 195(2):176-84).

Design of a flexible electrode can vary with applications and/or desired sizes. In some embodiments, the arrangement and/or shape of an electrode can be adapted to decrease surface area, e.g., due to space and/or shape constraint of a penetration site. The flexible electrode can then be at least partly coated or encapsulated in silk. Once encapsulated, the silk properties can be controlled for transition from stiff to flexible.

In some embodiments, the commercially-available flexible electrodes can also be used in the implantable system described herein.

While the electrical component can be an integral part of a pre-formed or conventional implantable device, the electrical component can also be directly or indirectly patterned or deposited on the silk matrix to form the silk-based implantable device. An exemplary patterning method is described, e.g., in Kim, D. H., et al "Silicon electronics on silk as a path to resorbable implantable devices." (2009) Applied Physics Letters 95(13):133701; and Kim, D. H. et al. "Dissolvable films of silk fibroin for ultrathin conformal biointegrated electronics." (2010) Nature Materials 9(6): 511-517. These reports indicate that silicon transistors can be fabricated on resorbable silk films for brain recordings on cats, with no inflammatory response in vivo.

The electrical component can be formed from any conventional materials commonly used for electronics in an implantable device, e.g., without limitations, silicon, gold, platinum, titanium, copper, alloys, and any combinations thereof. In some embodiments, the electrical component does not include a silicon transistor. Alternatively, the electrical component can include biodegradable electronics, e.g., made from biodegradable or erodible organic semiconductors such as melanins and carotenoids. In one embodiment, the electrical component can include a silk-based electrode as described herein.

In accordance with various aspects described herein, the silk matrix is dynamic with respect to its changes in the mechanical property before or during and after penetration (or between a dry state and a hydrated state). Before penetration and during at least part of the penetration process, the silk matrix is stiff enough to enable the implantable device to penetrate into a target tissue (e.g., without deformation such as buckling or bending). In some embodiments, the silk matrix can increase a buckling force of the electrical component and/or the implantable device by at least about 2-fold, at least about 3-fold, at least about 4-fold, at least about 5-fold, at least about 10-fold, at least about 25-fold, at least about 50-fold, at least about 100-fold, at least about 250-fold, at least about 500-fold, at least about 1000-fold, at least about 1500-fold, at least about 2000-fold, at least about 3000-fold, or higher, as compared to the absence of the silk matrix.

Upon penetration into the target tissue, the silk matrix in contact with the electrical component can become compliant upon the penetration, e.g., by hydration of the silk matrix. Such mechanical compliance of the silk matrix with surrounding tissue upon penetration can provide conformal contact between the electrical component and a surface of the target tissue. In some embodiments where the electrical component is associated with a neuroprosthetic device (e.g., an electrode pad), a tight interface can be formed between the neurons and the electrode pads. As used herein, the term "hydration" or "hydrated state" refers to at least a portion of the silk matrix having a water content of at least about 10%, at least about 20%, at least about 30%, at least about 40%, at least about 50%, at least about 60%, or more.

As used herein, the term "conformal contact" generally refers to a contact established between two surfaces. In one embodiment, conformal contact involves a macroscopic adaptation of one or more contact surfaces of an implantable system (including the electrical component and the silk matrix) or device to the overall shape of the surrounding tissue. In another embodiment, conformal contact involves a microscopic adaptation of one or more contact surfaces of an implantable system (including the electrical component and the silk matrix) or device to the surrounding tissue leading to an intimate contact without any detectable gap or a gap that would affect electrical connectivity between the device and the tissue (e.g., less than 50 µm, less than 40 µm, less than 30 µm, less than 20 µm, less than 10 µm, less than 5 µm, less than 1 µm, less than 0.5 µm, less than 0.1 µm, less than 0.01 µm or less).

In some embodiments, at least one side of the electrical component can be coated with the silk matrix. Thus, at least part of the electoral component can still be exposed to surrounding tissue, e.g., for detecting a signal. In some embodiments, the electrical component can be partially or completely coated or encapsulated in a silk matrix. Without wishing to be bound, the electrical component can also be encapsulated in the silk matrix. For example, in the case of an electrode encapsulated in a silk matrix, the silk around the electrode tip can either degrade immediately, or contain holes allowing close contact with the electrodes. Alternatively, the silk matrix over the electrode can be modified, doped, or functionalized with a conducting polymer (Abidian M. R. et al., "Multifunctional Nanobiomaterials for Neural Interfaces" Advanced Functional Materials (2009) 19: 573-585), thus making the silk matrix become conductive and thus extending the electrode through the silk.

In some embodiments, the silk matrix can reduce scar formation (e.g., gliosis) around the electrical component or the implantable device by at least about 10%, including at least about 20%, at least about 30%, at least about 40%, at least about 50%, at least about 60%, at least about 70%, at least about 80%, at least about 90%, at least about 95% or higher, as compared to the absence of the silk matrix.

Silk matrix can stabilize an active agent including a therapeutic agent for an extended release in vivo. Accordingly, in some embodiments, the silk matrix can comprise an active agent including, but not limited to, a therapeutic agent. The active agent (including a therapeutic agent) can include, e.g., but are not limited to, an agent that promotes tissue growth, controls inflammation, and/or reduces scar formation around the implanted system or device. In one embodiment, the active agent can include a gliosis-modulating agent. In some embodiments, the silk matrix can comprise two or more (e.g., 2, 3, 4, 5, 6 or more) active agents including therapeutic agents.

Depending on applications of the implantable device, and/or mechanical property of the silk matrix and/or implantation sites, the silk matrix can have a thickness of about 1 µm to about 1000 µm, about 5 µm to about 750 µm, about 10 µm to about 500 µm, about 25 µm to about 250 µm, or about 50 µm to about 200 µm. In some embodiments, the silk matrix can have a thickness more than 1 mm, including, e.g., more than 1.5 mm, more than 2 mm, or more than 3 mm, provided that the thickness can still provide mechanical compliance with the surrounding tissue upon penetration. The total thickness of the silk matrix can be resulted from a single layer or a plurality of silk layers, each of which can have the same or different thickness and optionally the same or different active agent. In some embodiments, the silk matrix can have at least about 1 layer, at least about 2 layers, at least about 3 layers, at least about 4 layers, at least about 5 layers, at least about 10 layers, at least about 15 layers, at least about 20 layers, at least about 25 layers, at least about 50 layers, at least about 100 layers or more. In one embodiment, the silk matrix can have at least about 3 layers to about 6 layers. Each layer can have a thickness of about 1 µm to about 100 µm, about 5 µm to about 75 µm or about 10 µm to about 30 µm. In some embodiments of any aspects described herein, the silk matrix in contact with an electrical component can have a thickness greater than 5 µm, greater than 10 µm, greater than 20 µm, greater than 30 µm, greater than 40 µm, greater than 50 µm or more. In some embodiments, the silk matrix in contact with an electrical component can have a thickness ranging from about 20 µm to about 1000 µm, about 30 µm to about 900 µm, about 40 µm to about 800 µm, about 50 µm to about 700 µm, about 50 µm to about 600 µm, or about 100 µm to about 500 µm.

The silk matrix coating on, depositing on, and/or encapsulating the electrical component and/or the implantable device can be performed by any methods known in the art, e.g., by dipping, casting and/or layer-by-layer deposition. In one embodiment, an electrical component and/or at least part of the implantable device can be dipped into a silk fibroin solution at a concentration of about 3% w/v to about 30% w/v, or about 5% w/v to about 25% w/v, or about 10% w/v to about 20% w/v. The coating is then allowed to dry. For example, as shown in 9A, the dip coating approaches can involve briefly immersing a pre-formed implantable device in a silk solution, followed by air-drying. The solutions utilized for dip coating can include (i) aqueous silk solution, (ii) high silk concentration HFIP solution, and (iii) heat-liquefied silk electro-gel (e-gel) solution, wherein the e-gel can have a transition between a gel and a solution upon application of a voltage. US Patent Application Publication No. US 2011/0171239 filed Dec. 21, 2010 for information about e-gel, the content of which is incorporated herein by reference.

Figure 6A:
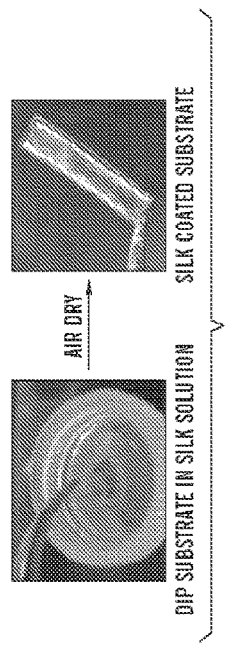
FIGS. 6A-6C show exemplary methods for coating flexible substrates in silk.
Figure 6B:
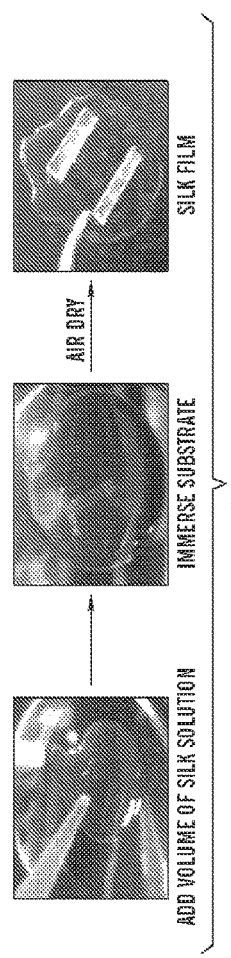
Figure 6C:
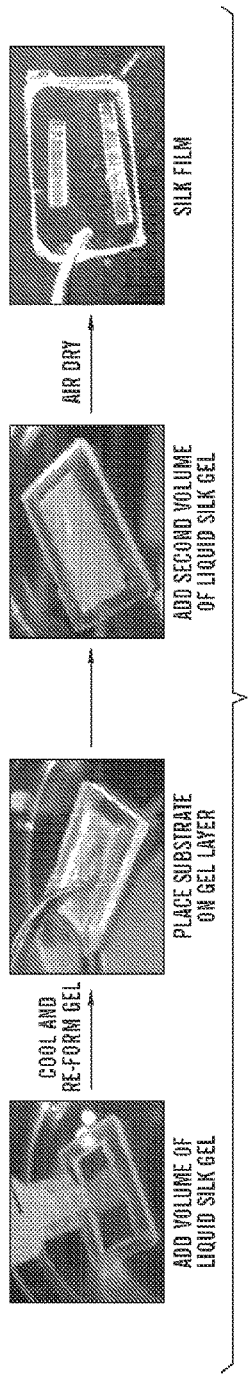

Alternatively, casting methods can involve submerging a pre-formed implantable device in a volume of aqueous or gel based silk solution and allowing the silk to air dry to form films (see FIGS. 6B-6C). The coated implantable device can then be manually cut out of the encapsulating film using a razor blade or scissors. For more precise release of the coated device from the silk film, a computer controlled laser cutter can be employed.

Figure 7A:
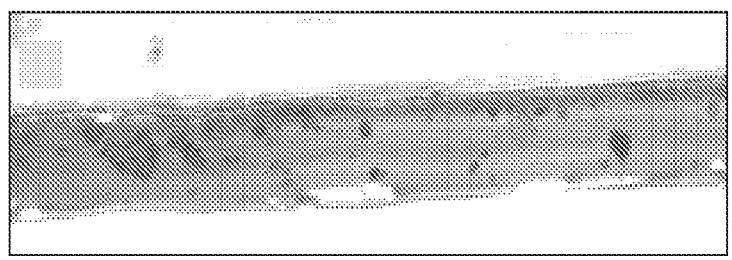
FIGS. 7A and 7B show side view of uncoated (~60 um thickness) and silk-coated (~120 um thickness) parylene strips, respectively. Coating was applied via two-step casting. Bar=200 micrometers.
Figure 7B:
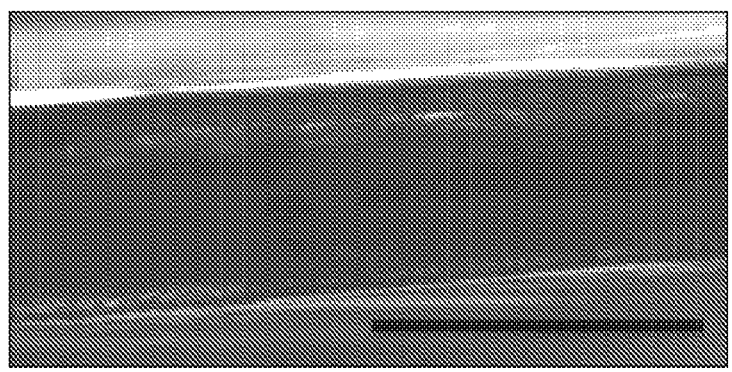
Figure 8:
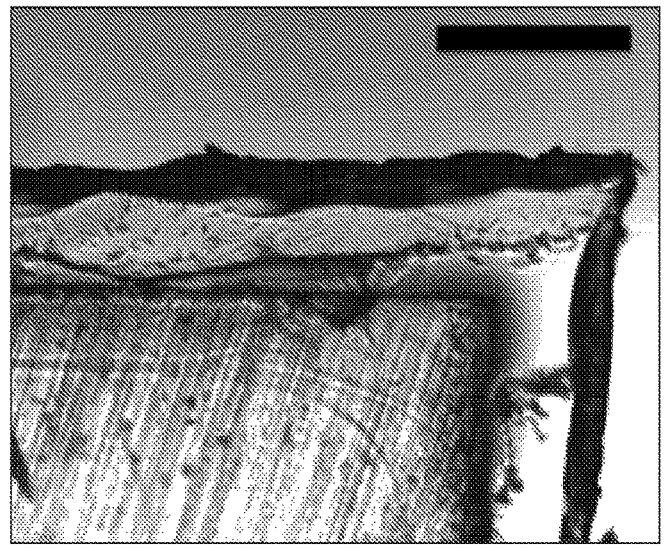
FIG. 8 shows top view of parylene coated in silk by two-step casting. Bar=500 micrometers.
Figure 9:
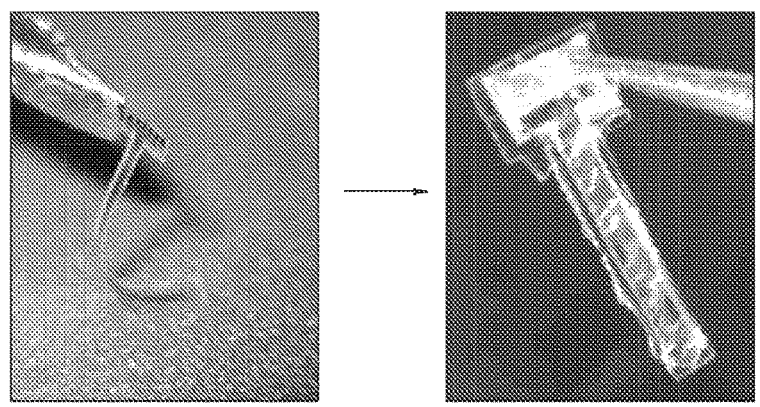
FIG. 9 shows an exemplary flexible electrode (left) coated in silk (right) using the two-step casting method. The shaft of the electrode is fully encapsulated in silk, while the top connector area has silk only on the back.

In particular embodiments, the casting method can involve a two-step layering process. First, a volume of heat-liquefied silk e-gel can be poured into a plate and allowed to re-gel by cooling (3-5 minutes). The implantable device and/or electrical component to be encapsulated can then be placed on top of the first e-gel layer and covered by another volume of heat-liquefied e-gel. The layered gel can then be left to air dry. This process can ensure even layers of silk on both sides of the electrical component and/or the implantable device, preventing delamination of the silk from the substrate upon drying. The coating formed uniform layers on the electrical component and/or the implantable device, the thickness of which can be individually controlled by adjusting the volume and/or concentration of the silk solution applied in each layer (see FIGS. 7A-7B and 8). Furthermore, the viscosity of the liquefied e-gel solution can allow for selective and localized application of the top layer. This can enable portions of the implantable device to be left uncoated as desired, e.g., electrical leads for contact with surrounding cell(s) and/or tissue upon penetration. For instance, as shown in FIG. 9, only one side of the contact pads on an electrode was coated with silk. In some embodiments, an active agent can be incorporated into a silk solution, which can be entrapped upon drying and released after implantation.

Applications of the silk-based implantable systems are also provided herein. For example, a method of inserting a flexible or soft implantable device (e.g., an implantable device that generally buckles and/or bends during insertion) into a target tissue comprises providing a silk-based implantable system described herein, wherein the silk-based implantable system comprises the flexible or soft implantable device at least partially coated with a silk matrix in its dry-state. The thickness of the silk matrix coating on the flexible or soft implantable device can vary with the penetrate site and/or mechanical property of the target tissue to be penetrated. In some embodiments, the thickness of the silk matrix coating on the flexible or soft implantable device can be adjusted such that the silk-coated implantable device is stiff enough to penetrate into the target tissue, but become compliant with the target tissue within a period of time (e.g., within minutes or hours) after penetration.

In some embodiments, the silk-based implantable systems can be used to reduce scar formation (e.g., gliosis) around the implantable device (e.g., a neuroprosthetic device) implanted in a tissue (e.g., a brain tissue), for example, by at least about 5%, at least about 10%, at least about 20%, at least about 30%, at least about 40%, at least about 50%, at least about 60%, at least about 70%, at least about 80%, at least about 90%, at least about 95%, or more, as compared to an implantable device without a silk coating. Accordingly, a method for reducing scar formation (e.g., gliosis) around an implantable device (e.g., a neuroprosthetic device) implanted in a tissue (e.g., a brain tissue) is also provided herein, e.g., by providing or obtaining a silk-based implantable system described herein or silk-based implantable device described below for implantation in a target tissue. In some embodiments where the pre-formed or conventional implantable device may not require a silk coating for additional strength during penetration, the silk matrix coating can be formed in situ, for example, the silk coating can be formed at the target site upon penetration. In such embodiments, the pre-formed or conventional implantable device can be adapted to include a silk reservoir which can supply a silk solution for forming in situ coating.

In some embodiments, the silk-based implantable systems can be used to improve or extend long-term functionality of an implantable device (e.g., a neuroprosthetic device) implanted in a tissue (e.g., a brain tissue) by at least about 3 days, at least about 1 week, at least about 2 weeks, at least about 3 weeks, at least about 1 month, at least about 2 months, at least about 3 months, at least about 4 months, at least about 5 months, at least about 6 months or more, as compared to the implantable device without a silk coating. For example, the silk-based implantable system can reduce biofouling around an implanted device, e.g., by at least about 10%, at least about 20%, at least about 30%, at least about 40%, at least about 50%, at least about 60%, at least about 70%, at least about 80%, at least about 90%, at least about 95%, or more, as compared to an implanted device without a silk coating. Without wishing to be bound by theory, biofouling can, at least partly, contribute to loss of function (e.g., recording of an electric signal at a biologically-relevant level, and/or providing an electrical stimulation) of an implantable device at the biological abiotic interface. Accordingly, reducing biofouling, e.g., by having a silk matrix coating on the implantable device can extend the life-time and/or operation time of the implantable device upon penetration in a tissue by at least about 1 week, about 2 weeks, about 3 weeks, about 1 month or longer. In some embodiments, the silk matrix coating can be pre-formed on the implantable device and/or be formed in situ as described herein.

Silk-Based Implantable Devices and Methods of Making the Same

Electronics that are capable of intimate, non-invasive integration with the soft, curvilinear surfaces of biological tissues offer opportunities for monitoring, diagnosing and treating disease or injury and for establishing brain/machine interconnects. Previous report shows a bio-interfaced system that relies on ultrathin film electronics supported by a bioresorbable substrate of silk. Placing such device on a tissue and then allowing the silk to dissolve and resorb can initiate a spontaneous, conformal wrapping process driven by capillary forces at the biotic/abiotic interface. Specialized mesh designs and ultrathin forms for the electronics can ensure minimal stresses on the tissue and highly conformal coverage, even for complex curvilinear surfaces. See, e.g., Kim et al. "Dissolvable films of silk fibroin for ultrathin conformal bio-integrated electronics" Nature Materials (2010) 9: 511-517. However, the report shows direct placement of such silk-supported ultrathin film electronics on a surface of a brain tissue, rather than inserting such device into a brain tissue. Such silk film-supported planar arrays generally use low silk concentrations, e.g., less than 5% (w/v) for thin sheets, that will conform to convoluted surfaces. Thus, unlike the silk-based implantable systems described herein, the silk film-supported planar arrays do not have the mechanical strength necessary for insertion into a tissue. Further, unlike some embodiments of the silk-based implantable systems described herein, theses thin films are designed to dissolve immediately, and thus they are not suitable for encapsulation of an active agent for an extended release.

One of the challenges with implantable devices is the effect of bio-fouling. For example, electrodes used for deep brain stimulation can generally function in the brain after implantation for a limited of time because of the bio-fouling. Another aspect described herein relates to a silk-based implantable device comprising a silk body with at least one electrically-conducting component. In some embodiments, the silk-based implantable device can be constructed to be capable of renewably forming a silk coating on a surface of the implantable device. Such silk-based implantable device can minimize biofouling, thus increasing the reliability and lifetime of the implantable device in vivo.

For example, in some embodiments, the silk body can include a silk reservoir of any shape with at least one electrically-conducting component formed on a least a portion of a surface of the silk reservoir (e.g., the surface that is in contact with a fluid upon implantation). In some embodiments where the silk-based implantable device are adapted for use as an electrode, the silk-based implantable device can comprise a silk body with more than one (e.g., 2, 3, 4, 5, 6, 7, 8, 9, 10, 25, 50, 75, 100, 250, 500, 750, 1000, 1500 or more) electrically conducting components. The term "electrically conducting component" as used herein refers to any component that is involved in an electric circuit to conduct electricity, e.g., but not limited to, electrodes, transistors, capacitors, battery leads, and/or electrical connectors such as wires or microwires.

In some embodiments, the electrically conducting component includes an electrode. As used herein, the term "electrode" means an electronic including an electric conductor through which a voltage potential can be measured. An electrode can also be a collector and/or emitter of an electric current.

In some embodiments, the term "electrode" as used herein refers to the electrode or electric contact or contacts only. In some embodiments, the term "electrode" can refers to the electrode or electric contact or contacts and one or more surrounding structures, e.g., a support substrate upon which the contacts are placed, the conductor wires and any other assemblies within or on the support substrate.

The silk body can be in any shape and/or form, depending on the application of an application device, and/or implantation site in a body. For example, the silk body can have a curved or a planar surface. In one embodiment, the silk body can be in a form of a tube, e.g., for use as an implantable electrode. Accordingly, in some embodiments, a silk-based implantable device comprising a silk-based self-cleaning or living-like electrode is also provided herein.

The silk body can have a lumen extending therethrough or one or more compartments independently distributed within a silk body for use as a silk reservoir. The lumen can have the same cross-section as that of the silk body or a cross-section that is different than that of the silk body. For example, the cross-section of the lumen can be round, substantially round, oval, substantially oval, elliptical, substantially elliptical, triangular, substantially triangular, square, substantially square, hexagonal, substantially hexagonal, or the like.

In some embodiments, the lumen has a diameter. The diameter can be, for example, approximately the same as the diameter of the rotating mandrel used in the preparation of the silk body. It is understood that the diameter can vary along the length of the lumen. Without limitations, the diameter can be from about 100 nm to about 10 mm. In some embodiments, the diameter can be from about 1 mm to about 5 mm, from about 1 mm to about 3 mm, from about 3 mm to about 5 mm, from about 2 mm to about 4 mm, about 1 mm, about 2 mm, about 3 mm, about 4 mm, or about 5 mm. In some embodiments, the diameter can be greater than about 5 mm. In some embodiments, the diameter can be less than about 1 mm. In other embodiments, the diameter of less than about 20 mm, for example, less than about 10 mm, or less than about 5 mm.

In some embodiments, the silk body can be a silk tube with at least one (including 1, 2, 3, 4, 5, 6, 7, 8, 9, 10, 15, 20, 25, 50, or more) electrically-conducting component formed on at least a portion of a lateral surface of the silk tube. For example, the electrically-conducting components can be arranged orderly or randomly on the lateral surface of the silk tube. In some embodiments, the electrically-conducting components are arranged on predefined locations on the lateral surface of the silk tube.

Figure 12A:
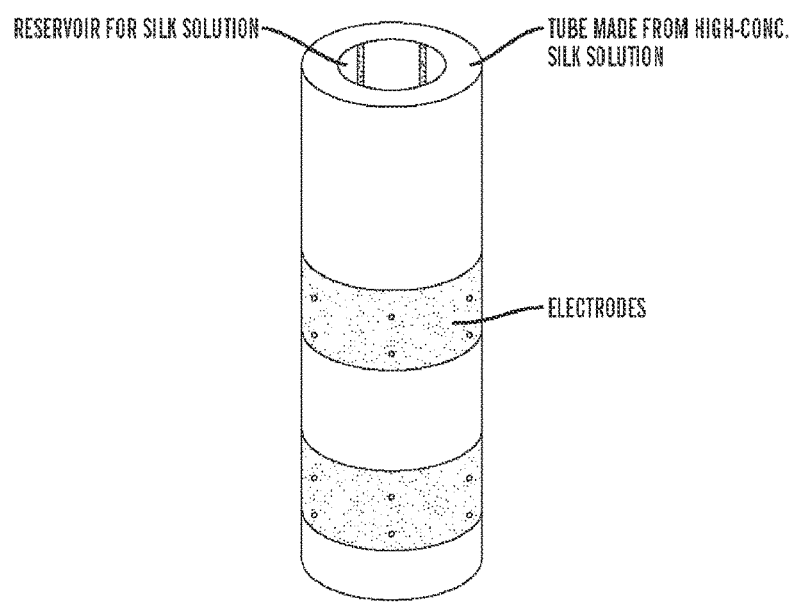
FIGS. 12A-12B are schematic diagrams of a silk-based electrode according to different embodiments described herein.

FIG. 12A shows one embodiment of a silk-based self-cleaning or living-like electrode. As shown in FIG. 12A, the silk-based electrode includes a silk tube with one or more electrically-conducting components formed on at least a portion of a lateral surface of the silk tube. In this embodiment, the silk tube is filled with a silk solution. The silk solution in such embodiments can be of any concentration that can form a coating sufficient to reduce biofouling or reduce gliosis as discussed herein. In some embodiment, the silk solution filled inside the silk tube can be at a concentration of about 10% (w/v) to about 30% (w/v), or about 15% (w/v) to about 25% (w/v). In some embodiments, the silk solution filled inside the silk tube can have a concentration of about 15% (w/v) or greater. Without wishing to be bound, in some embodiments, the silk concentration inside the silk tube can be lower than 15% (w/v) or lower than 10% (w/v), e.g., when the silk coating formed on the outside surface of the electrode is desirable to be thin and degrade over a short period of time. The silk tube can be very tough (e.g., with sufficient mechanical stiffness to penetrate a target tissue), but also with the ability to soften when placed in a wet environment.

Generally, the silk body (e.g., a silk tube) can have any length desired. For example, length of the silk body (e.g., a silk tube) can be from about 1 mm to about 10 cm. In some embodiments, length of the silk body (e.g., a silk tube) can be from about 1 mm to about 5 cm.

Without wishing to be bound by a theory, wall thickness of the silk tube and/or silk reservoir can affect the mechanical property of the implant and/or release of the silk solution encapsulated therein. Accordingly, the silk tube and/or silk reservoir can be selected to have a wall thickness that provides a desired rate of release. For example, wall thickness can range from about 50 µm to about 5 mm. In some embodiments, the wall thickness can be from about 50 µm to about 500 µm, from about 50 µm to about 1,000 µm, from about 200 µm to about 300 µm, from about 600 µm to about 800 µm, from about 200 µm to about 800 µm, from about 300 µm to about 700 µm, from about 400 µm to about 600 µm, or about 500 µm. In some embodiments, the wall thickness can be greater than about 1,000 µm. In some embodiments, the wall thickness can be less than about 100 µm. In some embodiments, the wall thickness can be about 0.25 mm, about 0.5 mm, about 0.75 mm, about 0.9 mm, about 1.0 mm, or about 1.7 mm.

As shown in FIG. 12A, in some embodiments, molding and shaping can provide the silk tube with a sharp tip and the material is stiff enough to be placed into a human brain without bending or fracturing. Circumferential electrodes can be formed on the outer tube surface by depositing a thin layer (tens of micrometers) of noble metal (e.g., gold) at predefined positions. Electrical leads can be connected through the inner diameter of the silk reservoir. Solubilized silk can be supplied through the inner tube diameter and discharged from the perforations in the electrodes. Electrogelation of the silk solution on the electrode surface through the application of a low DC voltage can provide a thin gel barrier to prevent bio-fouling, without degrading electrode function. Incorporation of the silk electrogelation (sol→gel) process is an exemplary feature of the silk-based implantable device described herein, because a polarity change in voltage application can causes the silk gel coating to dissipate (gel→sol). In this way, the electrode surface can be refreshed with the removal of bio-foul buildup and replacement of a fresh silk gel coating to restore good electrical connections. Electrogelation of silk is described in US Patent Application Publication No. US 2011/0171239 filed Dec. 21, 2010, the content of which is incorporated herein by reference. While FIG. 12A shows an entirely silk based implant with electrical contacts, methods of regenerating a silk coating can be applied to any implant of any material with electrical contacts. For example, an implant can be adapted to include a reservoir for silk solution, which can be in transient connection with an electric lead formed a surface of the implant to be coated.

The silk body can be formed from any concentration of silk, depending on the desired mechanical property of the implantable device, e.g., ranging from 5% w/v to about 40% w/v. Generally, the higher the concentration of silk is used, the stiffer the dry-state silk body will be. In some embodiments, the silk body can be formed from a high-concentration silk solution, e.g., ranging from about 10% w/v to about 40% w/v, or from 15% w/v to about 30% w/v. In some embodiments, the silk body can be formed from a silk solution with a concentration higher than about 20% w/v.

Generally, silk tubes can be made using any method known in the art. For example, tubes can be made using molding, dipping, spinning, and any combinations thereof. In one embodiment, the silk tube can be formed from a silk solution using a cylindrical mold (e.g., slightly oversized than the final desired outcome to accommodate shrinkage) and removable wire core. The solid material can then be removed from the mold and maintained at room temperature for 3 days (depending on the humidity) until the material is nearly dry. The center core is then removed and the silk tube is fully dried.

Alternatively, the silk tube can be produced from a silk solution by spinning a silk solution around a rotating and optionally axially reciprocating support structure (e.g., a mandrel). The term "spinning" as used herein can encompass any methods for creating a fiber, including, but not limited to, wet-spinning, dry-spinning, melt-spinning, e.g., extrusion spinning and direct spinning, gel spinning, electrospinning.

Figure 16:
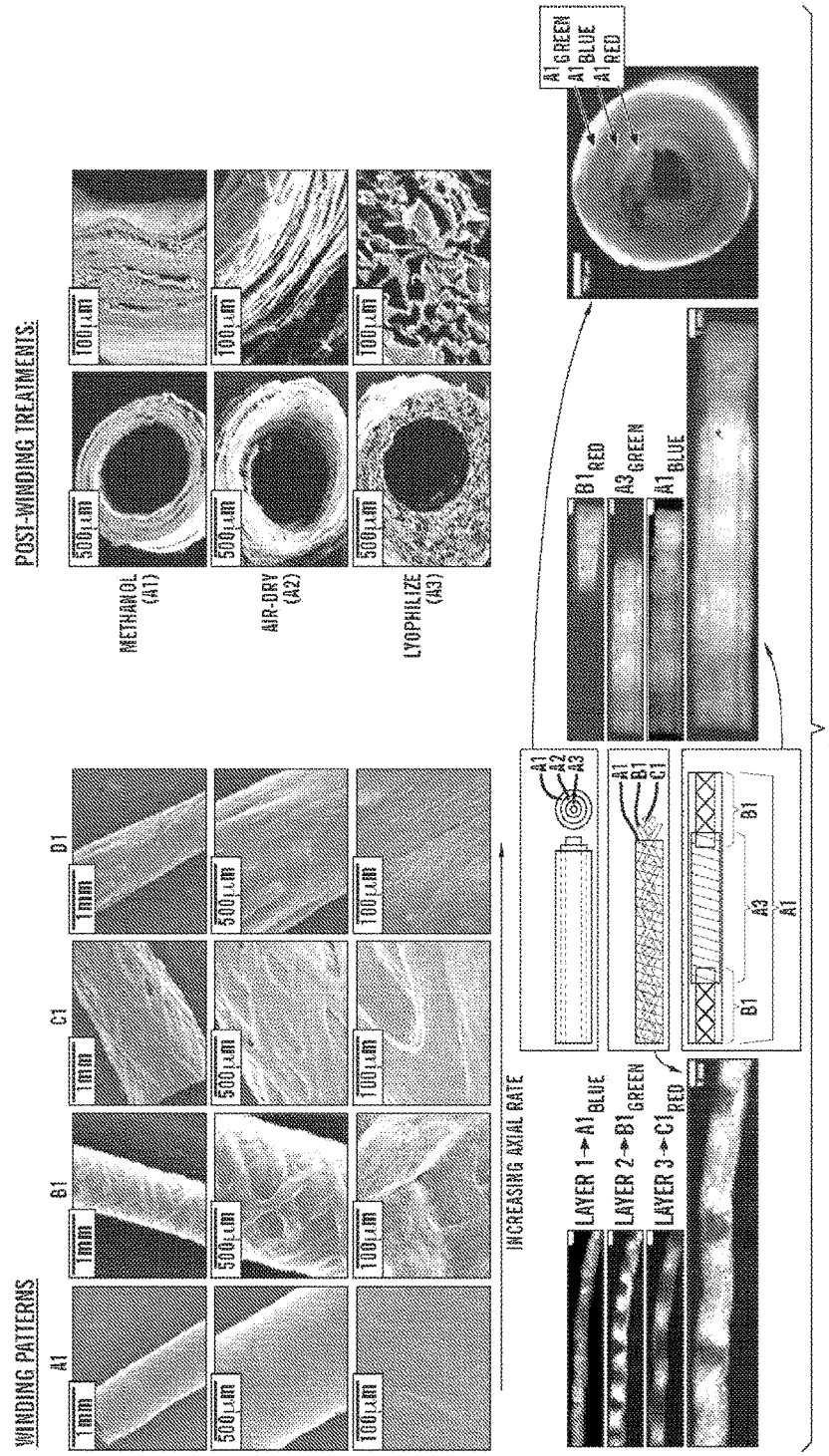
FIG. 16 is a set of images showing exemplary gel spun silk tubes indicating the versatility in engineering control of winding patterns (top left), tube wall porosity (top right), and loading of therapeutics or growth factors (bottom panel) in gradient and layered locations (shown with dyes for easy tracking).
Figure 17B:
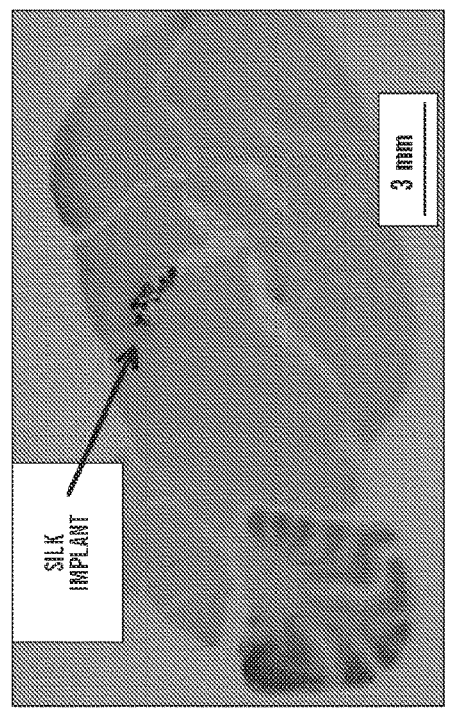
FIGS. 17A-17D show adenosine releasing silk implants for local epileptic seizure control.
Figure 17A:
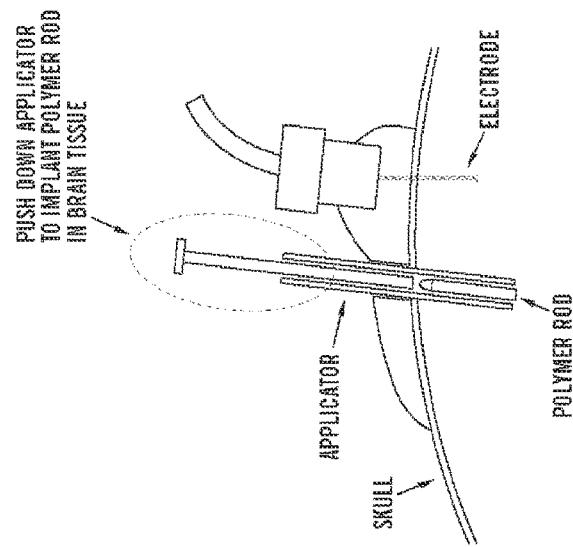
Figure 17D:
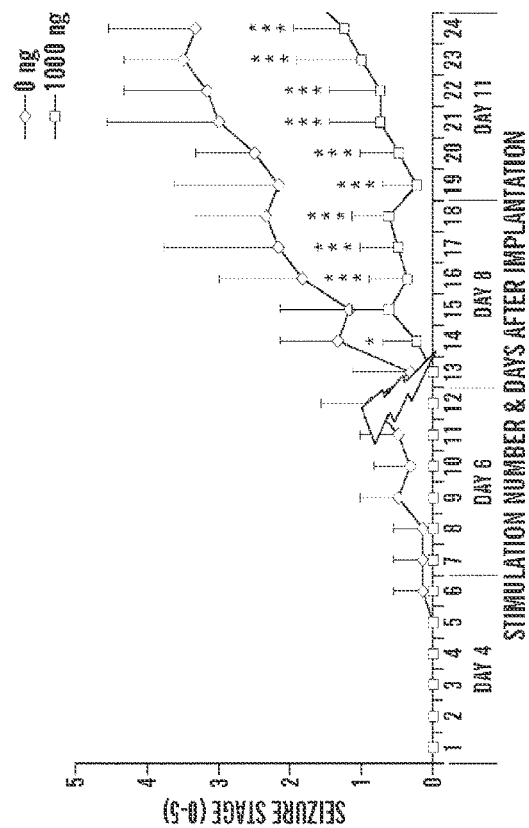
Figure 17C:
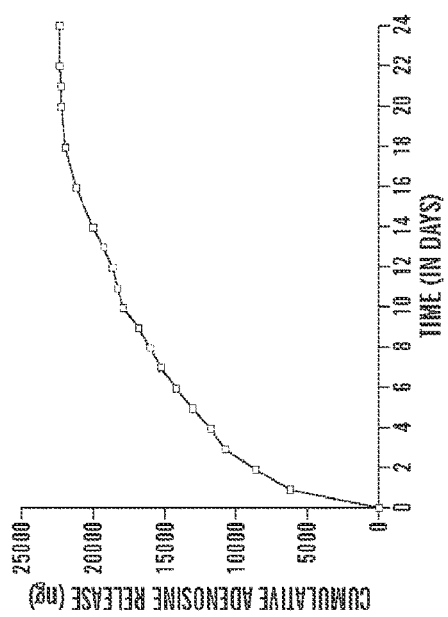
Figure 18A:
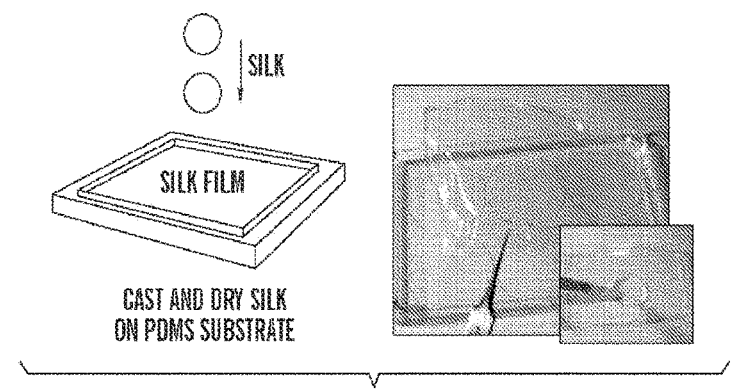
FIGS. 18A-18C are schematic illustration and images corresponding to steps for fabricating conformal silk-supported PI electrode arrays.
Figure 18B:
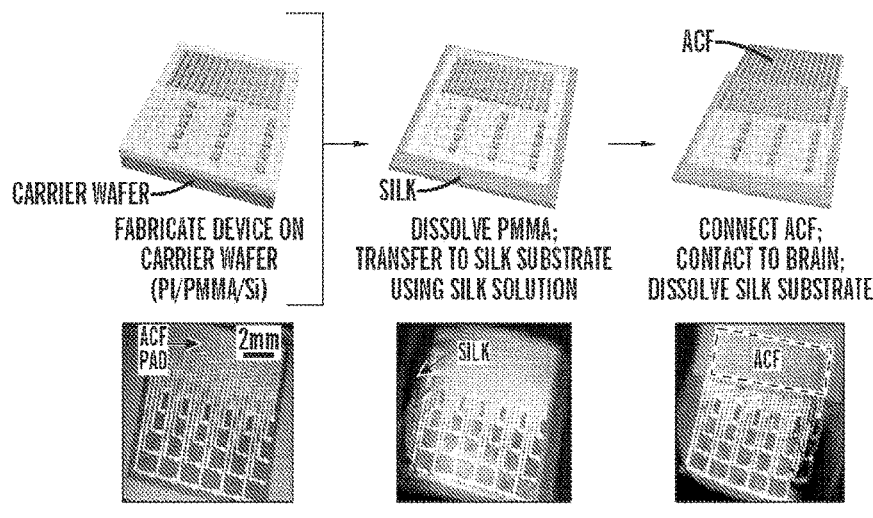
Figure 18C:
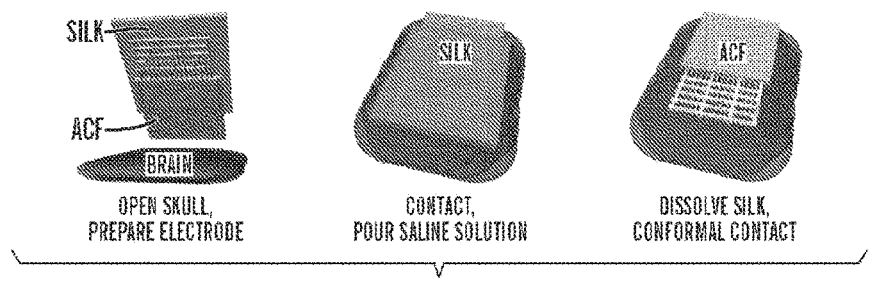
Figure 19A:
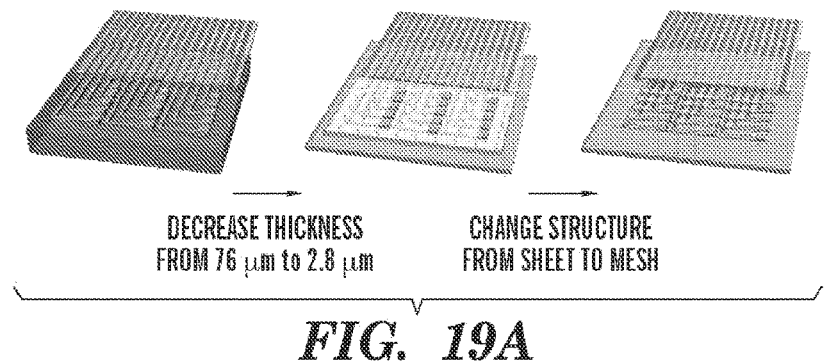
FIGS. 19A-19D show neural electrode arrays of varying thickness on simulated brain models to illustrate flexibility.
Figure 19B:
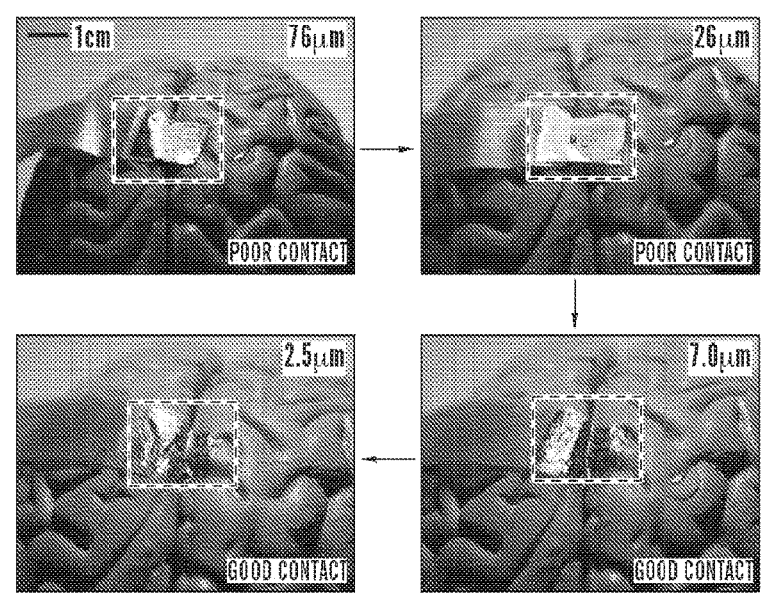
Figure 19C:
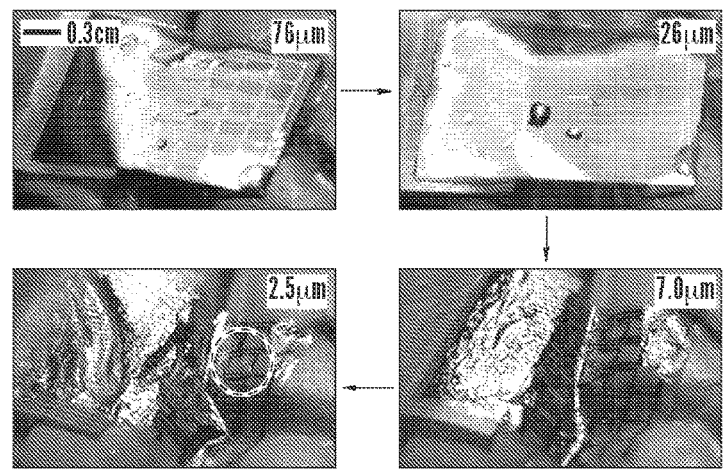
Figure 19D:
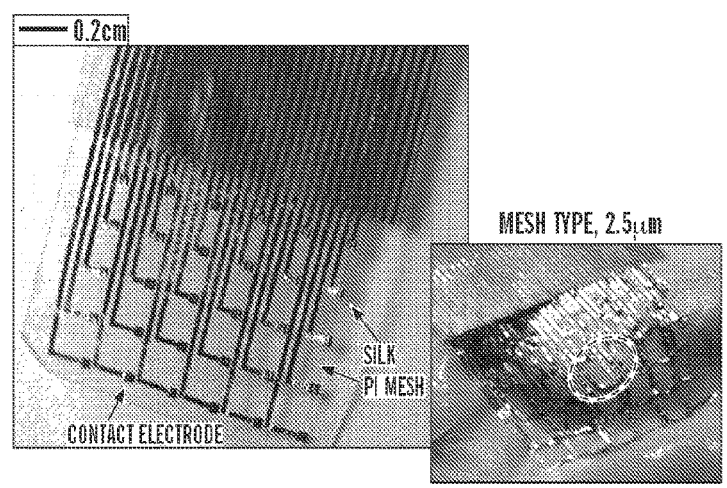
Figure 20:
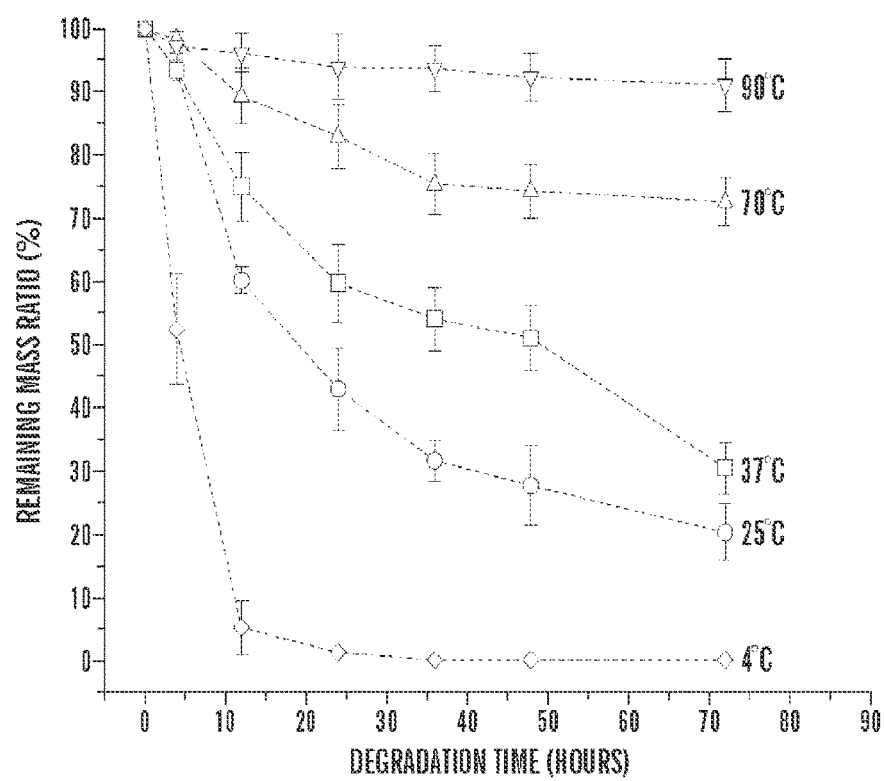
FIG. 20 is a plot of silk processing relationships to degradation rate showing programmable degradation lifetime. Further, silk is an FDA approved biomaterial for use in a biomedical polymer system due to capability of processing the silk protein to avoid inflammation while preserving biodegradability.

In some embodiments, the silk tube can be produced from a silk solution by gel spinning. Gel spinning involves winding a silk solution around a reciprocating and rotating mandrel. As shown in FIG. 16, final gel-spun silk tube porosity, winding patterns, structure and mechanical properties can be controlled via axial and/or rotational speeds of the mandrel and/or different post-spinning processes such as alcohol (e.g., methanol, ethanol, etc) treatment, air-drying or lyophilization. Gel spinning is described in Lovett et al. (*Biomaterials*, 29(35):4650-4657 (2008)) and in PCT application no. PCT/US2009/039870, entitled "System and Method for Making Biomaterial Structures" filed Apr. 8, 2009, the content of all of which is incorporated herein by reference. Without wishing to be bound by a theory, the inner and outer diameter of the silk tube can be controlled readily using gel-spinning.

In some embodiments, the silk tube can be produced from a silk solution by electrogelation. For example, the silk solution can become gel-like around a tubular support structure upon application of a voltage to the support structure. Electrogelation of a silk solution is described in US Patent Application Publication No. US 2011/0171239 filed Dec. 21, 2010 the content of which is incorporated herein by reference.

Any other art-recognized methods for making a tubular structure can also be used to the silk tubular body. For example, the method described in U.S. application Ser. No. 12/672,521, entitled "Tubular Silk Compositions and Methods of Use Thereof" filed Aug. 11, 2008 can also be used for making a silk tubular body.

In some embodiments, the tubular structure can be produced by molding/freezing method. For example, a silk solution of about 25% w/v fibroin can be injected into a tubing as a mold and both ends can be sealed, e.g., using the high heat of a soldering iron. The silk-containing tubing can then be stored for a pre-determined period of time at a sub-zero temperature, e.g., between about −3° C. and about −9° C. In some embodiments, the silk-containing tubing can be stored at −5° C.

The resulting morphology of the silk matrix can depend on, e.g., the cooling temperature and/or duration of cooling. In some embodiments, the silk-containing tubing can be stored at a sub-zero temperature for at least about 3 days, at least about 1 week, at least about 2 weeks, at least about 3 weeks, at least about 4 weeks or longer. In one embodiment, the silk-containing tubing is stored at about 5° C. for a period of at least about 1 week.

Upon removal from the freezer, the molded material can released from the tube by any methods known in the art, e.g., by flushing the inner diameter with a fluid, e.g., water, or cut the mold open.

Such molding/freezing processing method can allow fabrication of tubular structure with any diameters, e.g., by using an appropriate tubing selection. Further, the molding/freezing processing method can be used to produce a silk body of different shape other than a tubular structure, e.g., an irregular shape, depending on the shape and/or form of the mold. An exemplary molding/freezing processing of a silk solution to form different structures is described, e.g., in Prov. App. No. 61/477,486, filed Apr. 20, 2011, the content of which is incorporated herein by reference.

In some embodiments, the silk body can comprise a first silk layer and a second silk layer, wherein at least one of the first and the second silk layer can comprise at least one electrically-conducting component formed on at least a portion of a surface of the silk layer. In some embodiments, silk particles or powder can be included between the first and the second silk layers. In some embodiments, the silk body can have more than 2 layers, e.g., 3, layers, 4 layers, 5 layers, 6, layers, 7 layers, 8 layers, 9 layers, 10 layers, 15 layers, 20 layers or more. The number of silk layers can affect the thickness of the silk body and/or mechanical property of the silk body. In general, increasing the number of silk layers can increase the thickness of the silk body and thus strengthening the mechanical property of the silk body, when it is in a dry-state. Further, increasing the number of silk layers can increase the period of time required to make the silk body become flexible and/or softer.

The silk layers of the silk body can be formed by layer-by-layer deposition method. For example, a second silk layer is independently formed or deposited on the first silk layer. Alternatively, the silk layers of the silk body can be formed by folding, rolling or wrapping a silk sheet one or a plurality of times to reach a desired number of layers.

Figure 12B:
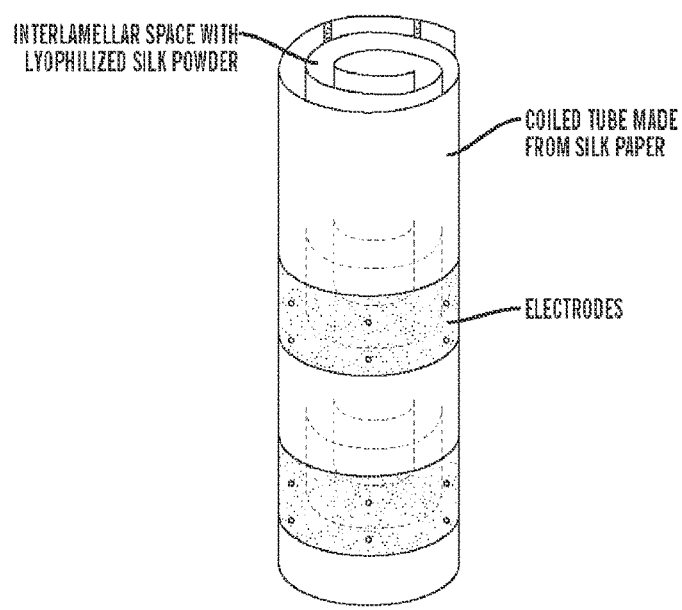

FIG. 12B shows an example of a silk-based self-cleaning or living-like electrode formed by wrapping or rolling a silk sheet. Electrodes can be formed on the silk paper before forming a tube by depositing a thin layer of noble metal (e.g., gold) at specific positions. Metal deposition can also be employed to make electrical connections to the electrodes on silk paper. While the electrode design does not involve the introduction of a silk solution from outside the body, silk solution can be produced in situ. To achieve this, lyophilized silk particles, powder, gel-like particles, silk film, or gel-like silk film can be wrapped between the layers of silk sheet. Upon introduction of the silk electrode into a tissue (e.g., brain tissue), the presence of an interstitial fluid or body fluid surrounding the target tissue (e.g., cerebrospinal fluid) can cause the outermost lyophilized silk to solubilize. Similar to the silk-based electrode shown in FIG. 12A, this solubilized silk can then be discharged through perforations in the electrodes and form a thin gel coating through the electrogelation process. In some embodiments, the silk-based electrode as shown in FIG. 12B is designed to be sacrificial. As the underlying silk sheet degrades over time, starting with the outer layer, fresh electrode surfaces become exposed. In this way, the silk electrode can have an extended useful lifetime.

In any embodiments, the discharge of a silk solution from a silk reservoir onto an electrically-conducing component of the silk body can be controlled by any methods known in the art, e.g., by passive diffusion, an implantable pump and/or an external pump. Passive diffusion of silk solution can be partly controlled by beta-sheet content, and/or concentration of the silk solution.

In various embodiments of the silk-based implantable devices described herein, to allow the silk solution to form a coating on a surface of the electrically-conducting component, in some embodiments, the electrically-conducting component can include one or more through holes such that the silk solution present in the silk reservoir (e.g., silk tube) between the silk layers can be discharged onto the surface of the electrically-conducting component to be coated. The solution can be discharged onto the surface of the electrically-conducting component to be coated by any methods known in the art, including, but not limited to, diffusion, an implantable pump, and/or an external pump. The silk solution discharged onto the surface of the electrically-conducting component can form a gel-like coating upon application of a first voltage through the electrically-conducting component. In some embodiments, the gel-like coating can be removed, e.g., by transforming the gel-like coating to a solution upon application of a second voltage with a polarity opposite to the first voltage.

The electrical conducting component can include any material that is commonly used as electronics for implantable devices, and/or an electrically-conductive material. In some embodiments, the electrical conducting component can include a metal such as a transition metal (e.g., silicon, copper), a noble metal (e.g., gold, titanium, platinum), or a combination thereof.

In some embodiments, the electrical conducting component can include a biodegradable component that can conduct electricity such as biodegradable organic semiconductors (e.g., melanins and/or carotenoids).

In some embodiments, the electrical conducting component can include silk modified to conduct electricity. For example, the silk can be functionalized by modifying a tyrosine of the silk protein to a sulfate group followed by polymerization of the modified tyrosine with a conducting polymer. Alternatively, the silk can be doped with a conductive material including, but not limited to, gold nanoparticles, carbon nanotubes, graphene, and a conducting polymer. Non-limiting examples of a conducting polymer can include polyethylenedioxythiophene (PEDOT), polypyrrole-based conductive polymer, copolymers of thiophenes and polypyrroles, copolymers of poly-lactide and polyaniline, or any combinations thereof. Exemplary methods for modifying silk to conduct electricity are further described later.

In some embodiments, the silk-based implantable device can be adapted for use as an implantable brain penetrating electrode. For example, the silk body can be in a form of a silk tube with a diameter of less than 2 mm. In some embodiments, the silk-based electrode can have a tensile strength of at least about 2 MPa when the silk body is in a dry state. In some embodiments, the silk-based electrode can have a shear modulus of less than about 200 kPa upon contact of the silk body with a fluid (e.g., interstitial fluid and/or body fluid such as cerebrospinal fluid).

In some embodiments, the silk body can comprise one or more active agents including a therapeutic agent. In some embodiments, the silk body can comprise two or more active agents including one or more, or two or more therapeutic agents.

Methods for regenerating a silk coating on a surface of a device are also provided herein. In some embodiments, the method comprises providing the silk-based device described herein, wherein the silk solution discharged onto the surface of the electrically-conducting component can form a gel coating upon application of a first voltage through the electrically-conducting component, and can optionally turn to a solution upon application of a second voltage with a polarity opposite to the first voltage.

The capability of renewing or regenerating the silk coating on a surface of a device can reduce biofouling, e.g., by at least about 10%, at least about 20%, at least about 30%, at least about 40%, at least about 50%, at least about 60%, at least about 70%, at least about 80%, at least about 90%, at least about 95%, or more, as compared to an implanted device without a silk coating. Accordingly, a method of reducing biofouling of a device is provided herein. The method comprises providing the silk-based device described herein, wherein the silk solution discharged onto the surface of the electrically-conducting component forms a gel coating upon application of a first voltage through the electrically-conducting component, and can optionally turn to a solution upon application of a second voltage with a polarity opposite to the first voltage.

In some embodiments of any methods described herein, the first voltage and/or the second voltage can be applied to the electrically-conducting component at any potential, provided that the voltage potential is high enough for silk gelation, but not detrimental to the tissue in contact with the electrically-conducting component. In some embodiments, the first voltage and the second voltage can be at least about 1.2V, at least about 1.5V, at least about 2V, at least about 3V, at least about 5V, at least about 10V, at least about 25 V, at least about 30V, at least about 50V, at least about 75 V or higher. In other embodiments, the first voltage and the second voltage can be about 1.2V to about 100V, about 2 V to about 75V, or about 5 V to about 50 V.

In some embodiments of any method described herein, the silk solution discharged onto the surface of the electrically-conducting component to form a gel coating can occur once a week, once a month, once every two months, or once every three months, or less frequently.

In some embodiments, the methods described herein can further comprising solubilizing the previous gel coating formed on the surface of the electrically-conducting component, e.g., prior to forming another fresh layer of the gel coating, by applying a second voltage with a polarity opposite to the first voltage. Accordingly, in some embodiments, the capability of the silk-based implantable devices to renew or regenerate a silk coating on a surface of the device can extend the life-time and/or operation time of the implantable device upon penetration in a tissue by at least about 1 week, about 2 weeks, about 3 weeks, about 1 month or longer.

In some embodiments, the silk-based implantable device can be placed in vivo or in situ. Thus, any embodiments of the methods described herein can be carried out in vivo or in situ. Without wishing to be bound, not only can different aspects of dynamic silk coating described herein be applicable for in vivo use (e.g., in a subject in situ such as a mammalian subject, e.g., human), but they can also be used in a non-living object in situ, e.g., in a machine.

Silk-Based Electrode

Some embodiments of the silk-based implantable device can be adapted for use as silk-based electrodes in any part of a body in a subject. In one embodiment, the silk-based implantable device described herein can be adapted for use as a silk-based brain penetrating electrode.

For example, the silk-based electrode can have a dimension large enough to yield a mechanical stiffness sufficient to penetrate into a target tissue, while small or thin enough to avoid any significant tissue damage. The target tissue can be anywhere in the body of a subject, e.g., where an electrical stimulation and/or signal recording is in need. Exemplary target tissue can include, but are not limited to, neural tissue (e.g., brain dura), heart tissue, cochlea, cochlear nucleus complex in the lower brain stem, inferior colliculus, cornea, aqueous humor, vitreous humor, or spinal cord. In some embodiments, the silk-based electrode can have a mechanical stiffness sufficient to penetrate into a brain tissue such as brain dura.

In some embodiments, the silk-based electrode can have a diameter of less than 2 mm, less than 1 mm, less than 0.5 mm, less than 0.25 mm, less than 0.1 mm or smaller. In some embodiments, the silk-based electrode can have a diameter of less than 500 µm, less than 250 µm, less than 100 µm, less than 50 µm, less than 25 µm, less than 10 µm, less than 5 µm, less than 2.5 µm, less than 1 µm, less than 0.5 µm, or lower.

Depending on the mechanical property of the target tissue, the silk-based electrode can have a diameter of more than 2 mm or smaller than 0.5 µm.

Human dura mater has been reported to have tensile strength ranging from 3-12 MPa, with a Young's modulus ranging from 20-190 MPa, depending on fiber orientation (Zerris et al., 2007). A previous report shows a peak insertion force of 140 mN for a silicon probe with thickness 100 µm and width 120 µm inserted through the dura of a monkey (Hoffmann et al., 2007). Accordingly, in some embodiments, in order to be sufficiently stiff to penetrate into the target tissue, the silk-based electrode can have a Young's modulus of more than 1 MPa, 2 MPa, 3, MPa, 4 MPa, 5 MPa, 6 MPa, 7 MPa, 8 MPa, 9 MPa, 10 MPa, 15 MPa, 20 MPa, 30 MPa, 40 MPa, 50 MPa, 60 MPa, 70 MPa, 80 MPa, 90 MPa, 100 MPa, or higher, when it is in a dry-state. In some embodiments, the silk-based electrode can have a Young's modulus of more than 100 MPa, 250 MPa, 250 MPa, 500 MPa, 1000 MPa, 2500 MPa, 5000 MPa, 7500 MPa, 10,000 MPa, or higher, when it is in a dry-state. As used herein, the term "dry-state" refers to a silk matrix being hydrated (e.g., water content) for no more than 30%, no more than 20%, no more than 10%, no more than 5%, no more than 2.5%, no more than 1%, no more than 0.5%, no more than 0.1%, no more than 0.01%. In one embodiment, the dry-state refers to 0% water content (i.e., completely dry).

In accordance with different aspects provided herein, the silk-based electrode becomes compliant upon the penetration into the target tissue. As used herein, the term "compliant" refers to a silk-based implantable system or device becoming mechanically compliant to a target tissue upon penetration into a target tissue. For example, the silk-based implantable system or device is able to reduce strain arisen from the mismatch between the elastic modulus of brain tissue and the silk-based implantable system or device in its dry-state, e.g., by becoming softer or flexible when in contact with a fluid upon the penetration. By way of example only, the shear modulus of brain tissue is ~10 kPa, with white matter stiffer (~12 kPa) than gray matter (~8 kPa) (McCracken et al., 2005). A 0.6% agar gel is commonly used as a phantom to approximate the mechanical stiffness of the brain.

Accordingly, in some embodiments, the silk-based electrode, upon the penetration in a target tissue (and/or contact with a fluid) for a certain period of time, can have an elastic modulus reduced by at least about 2-fold, at least about 3-fold, at least about 4-fold, at least about 5-fold, at least about 10-fold, at least about 25-fold, at least about 50-fold, at least about 100-fold, at least about 250-fold, at least about 500-fold, at least about 750-fold, at least about 1000-fold, as compared to when it is in the dry-state, e.g., before penetration into the target tissue. In some embodiments, the silk-based electrode, upon the penetration in a target tissue (and/or contact with a fluid) for a certain period of time, can have an elastic modulus or shear modulus of less than 500 kPa, less than 250 kPa, less than 200 kPa, less than 150 kPa, less than 100 kPa, less than 75 kPa, less than 50 kPa, less than 25 kPa, less than 20 kPa, less than 10 kPa, less than 5 kPa or lower. In one embodiment, the silk-based electrode can have a shear modulus of less than about 200 kPa upon contact of the silk body with a fluid (including interstitial fluid and/or body fluid such as cerebrospinal fluid).

Without wishing to be bound by theory, the silk-based implantable system or device (e.g., silk-based electrode) becomes softer or flexible when it is hydrated by being in contact with a fluid (e.g., interstitial fluid or body fluid such as cerebrospinal fluid) upon penetration into a target tissue for a certain period of time. Depending on the dimension, beta-sheet content of silk, silk concentration, structure/surface area (e.g., porous vs. non-porous), additives (e.g., glycerol) if any, and/or dry-state mechanical property of the silk-based implantable system or device, the silk-based implantable system or device can become softer or flexible upon penetration into a target tissue after a period of time ranging from few minutes to hours to days. In some embodiments, the silk-based implantable system or device can become softer or flexible upon penetration (e.g., become compliant with the target tissue to be penetrated) after at least about 1 minute, at least about 2 minutes, at least about 3 minutes, at least about 5 minutes, at least about 10 minutes, at least about 15 minutes, at least about 30 minutes or longer. In some embodiments, the silk-based implantable system or device can become softer or flexible upon penetration (e.g., become compliant with the target tissue to be penetrated) after at least about 1 hour, at least about 2 hours, at least about 3 hours, at least about 4 hours, at least about 5 hours, at least about 6 hours, at least about 12 hours, at least about 16 hours, at least about 24 hours, at least about 2 days, at least about 3 days, at least about 4 days, at least about 5 days, at least about 6 days, at least about 7 days or more. In some embodiments, the silk-based implantable system or device can become softer or flexible upon penetration into a target tissue after a period of about 16 hours to about 30 hours. In some embodiments, the hydration or re-hydration rate can be further controlled by addition of a more hydrophobic coating layer (e.g., higher beta sheet content), or polymer additions that can be used to further control the rehydration and the resulting mechanical properties.

Silk is 100% degradable via enzymatic processes, with programmable lifetimes from hours to years pending the mode of processing (See, e.g., Wang, X. et al. "Controlled release from multilayer silk biomaterial coatings to modulate vascular cell responses." Biomaterials (2008)29(7):894-903; Kim, D. H., et al. "Dissolvable films of silk fibroin for ultrathin conformal biointegrated electronics. Nature Materials" (2010) 9(6):511-517). The degradation rate of the silk matrix within the silk-based implantable system or device as described herein can be controlled by the beta-sheet crystalline content of silk, silk concentration and/or porosity of the silk matrix. Generally, increasing the beta-sheet crystalline content of silk and/or silk concentration, and/or decreasing porosity of the silk matrix can decrease the degradation rate of the silk matrix within the silk-based implantable system or device. Methods to increase the beta-sheet crystalline content of silk is known in the art, e.g., by alcohol immersion, water annealing, heat annealing, electrogelation, pH, shear stress, and any combinations thereof. For example, water vapor annealing at variable temperatures can be used to directly control crystalline content (beta sheet) which relates directly to degradation lifetime.

In the case of degradation and/or dissolution, Protease XIV can be utilized to assess degradation kinetics under physiological conditions at 37° C. Controls can be run under the same conditions but without enzyme. Gravimetric weight changes can be used to track changes with time. This process can be regulated so that degradation is almost immediate (e.g., dissolution) due to a low beta sheet content, or long (weeks, months or years), if beta sheet content is higher. If needed, inhibitors of proteases can be included in devices to further control the degradation process.

In some embodiments, the silk matrix within the silk-based implantable system or device (e.g., silk-based electrode) can partially or completely (e.g., at least about 10%, at least about 20%, at least about 30%, at least about 40%, at least about 50%, at least about 60%, at least about 70%, at least about 80%, at least about 90%, at least about 95%, up to and including 100% of the silk matrix) degrade within at least about 1 day, at least about 2 days, at least about 3 days, at least about 4 days, at least about 5 days, at least about 6 days, at least about 7 days or more. In some embodiments, the silk matrix within the silk-based implantable system or device can partially or completely (e.g., at least about 10%, at least about 20%, at least about 30%, at least about 40%, at least about 50%, at least about 60%, at least about 70%, at least about 80%, at least about 90%, at least about 95%, up to and including 100% of the silk matrix) degrade within at least about 1 week, at least about 2 weeks, at least about 3 weeks, at least about 4 weeks, at least about 5 weeks, at least about 6 weeks, at least about 7 weeks, at least about 8 weeks or more. In some embodiments, the silk matrix within the silk-based implantable system or device can partially or completely (e.g., at least about 10%, at least about 20%, at least about 30%, at least about 40%, at least about 50%, at least about 60%, at least about 70%, at least about 80%, at least about 90%, at least about 95%, up to and including 100% of the silk matrix) degrade within at least about 1 month, at least about 2 months, at least about 3 months, at least about 4 months, at least about 5 months, at least about 6 months, at least about 7 months, at least about 8 months or more The electrical component or electrically-conducting material in a silk-based implantable system or device can have a conductivity that allows recording or detection of extracellular field potentials of at least one cell or a cluster of cells. For example, the extracellular field potentials are generally on the order of 100 µV for single neurons, or ~1-~10 mV for neuronal clusters. In some embodiments, the electrical component or electrically-conducting material in a silk-based implantable system or device can have a conductivity that allows detection of extracellular field potentials ranging from about 1 µV to about 100 mV, from about 10 µV to about 50 mV, from about 50 µV to about 20 mV.

Stated another way, the electrical component or electrically-conducting material present in a silk-based implantable system or device can have a resistivity comparable to (e.g., at least about 60%, at least about 70%, at least about 80%, at least about 90%, at least about 95% or more of) that of a metal, such as gold and platinum, typically used in microelectrodes. In some embodiments, the electrical component or electrically-conducting material present in a silk-based implantable system or device can have a resistivity approaching on the order of 1-500 nΩ·m, or 20-100 nΩ·m. From a device perspective, in some embodiments, the impedance of a silk-based implantable system or device (e.g., a silk-based electrode) can be in the range of about 0.5 kΩ to about 50 MΩ, about 5 kΩ to about 10 MΩ, or about 50 kΩ to about 1 MΩ at a frequency of about 0.1 kHz to about 10 kHz, or about 0.5 kHz to about 5 kHz in a physiologic environment. In some embodiments, the impedance of a silk-based implantable system or device (e.g., a silk-based electrode) can be in the range of about 50 kΩ to about 1 MΩ at a frequency of about 1 kHz in a physiologic environment. In some embodiments, the electrical characteristics of the silk-based electrode can be comparable to (e.g., at least about 60%, at least about 70%, at least about 80%, at least about 90%, at least about 95% or more of) existing brain penetrating electrodes.

The electrically-conducting component can include any material that can conduct electricity and/or is commonly used as an electrode contact. Examples of an electrically-conducting component can include, but are not limited to a metal such as a transition metal and/or a noble metal. An exemplary transition metal for use in an electrically-conducting component can include, without limitations, silicon and/or copper. Exemplary noble metals for use in an electrically-conducting component can include, but are not limited to, gold, platinum, titanium, any noble metal commonly used as an electronic, and any combinations thereof.

Figure 21A:
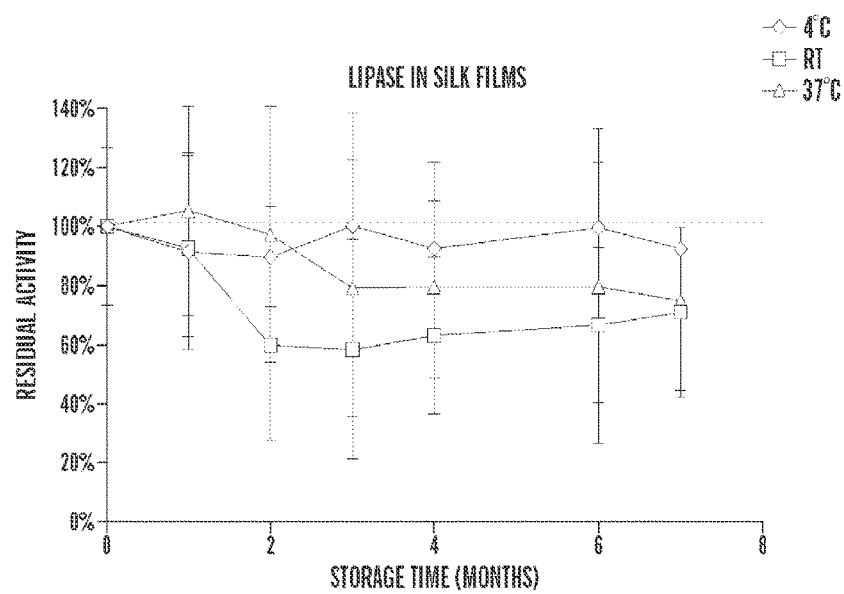
FIGS. 21A and 21B show exemplary stabilization of enzymes in silk films by entrainment over time (months) from 4 to 37° C., indicating that silk can stabilize a gliosis-modulating agent for glial scarring control.
Figure 21B:
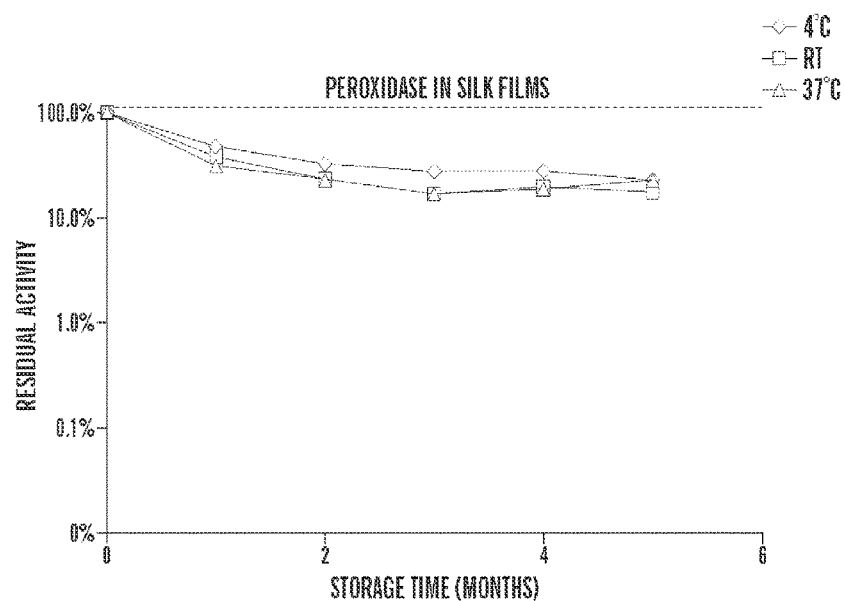

In such embodiments, the electrically-conducting component can be incorporated in the silk-based implantable system or device by any known methods in the art. In some embodiments, such electrically-conducting component can be deposited on a surface of the silk matrix or silk body at a desired position. In some embodiments, the electrically-conducting component can be patterned on a surface of the silk matrix or silk body at a desired position using the patterning method as shown in FIG. 21. See details of the patterning method on Kim, D. H., et al "Silicon electronics on silk as a path to resorbable implantable devices." (2009) Applied Physics Letters 95(13):133701; and Kim, D. H. et al. "Dissolvable films of silk fibroin for ultrathin conformal biointegrated electronics." (2010) Nature Materials 9(6): 511-517. These reports indicate that silicon transistors can be fabricated on resorbable silk films for brain recordings on cats, with no inflammatory response in vivo.

In some embodiments, biodegradable electronics, e.g., natural organic semiconductors such as melanin and carotenoid families of chemicals (with semiconductor properties) can be used in place of conventional electronic components, to form a completely biodegradable implantable system or device.

In some embodiments, the electrically-conducting component can include silk. While silk is inherently an insulator as a highly hydrophobic polymer with low water content, silk can be modified to become a conductive material. For example, various processing of silk can turn silk to become a piezoelectric material. Methods for producing a piezoelectric silk material are described in US Patent Application Publication No. US 2014/0145365 entitled "Silk-based piezoelectric materials" filed Nov. 22, 2013.

Additionally or alternatively, silk can be doped with a conductive material to generate a conductive composite material. Examples of a conductive material can include, but are not limited to, a metal particle (e.g., a gold nanoparticle), carbon nanotube, graphene, a conducting polymer, and any combinations thereof. In one embodiment, silk can be doped with conductive gold nanoparticles. See, e.g., Tao H. et al. "Gold nanoparticle-doped biocompatible silk films as a path to implantable thermo-electrically wireless powering devices" (2010) Appl. Phys. Lett. 97, 123702.

In another embodiment, silk can be doped with a conducting polymer. Exemplary conducting polymers for use as a dopant in silk can include, but are not limited to, polyethylenedioxythiophene (PEDOT), polypyrrole-based conductive polymer, copolymers of thiophenes and polypyrroles, copolymers of poly-lactide and polyaniline, or any combinations thereof. Conducting polymers have been reported for in vivo use, with low toxicity and good tissue compatibility. In some embodiments, a conducting polymer can be brittle, a property which can be improved by blending with silk. It has been previously reported that PEDOT can be used as a biocompatible coating for implantable electrodes, and that PEDOT can be polymerized around living cells. Alternatively, degradable/erodable conductive polymers can be blended with silk, including, but not limited to, erodible polypyrrole based conductive polymer, degradable conductive copolymers of thiophenes and polypyrroles linked by degradable ester linkages or degradable conducting copolymers consisting of poly-lactide and polyaniline. In such embodiments, using a degradable/erodible conductive polymer as a dopant in silk can allow for the synthesis of a fully resorbable conducting silk composite material.

The amount of a dopant present in a silk matrix body can vary with desired conductivity and/or types and conductivity of dopants. In some embodiments, the dopant can be present in a silk matrix or silk body in an amount of about 0.01% w/w to about 50% w/w, about 0.05% w/w to about 30% w/w, about 0.1% w/w to about 25% w/v.

In some embodiments, the electrically-conducting component can include silk modified to conduct electricity (e.g., having a conductivity defined herein, or having a resistivity defined herein). To make silk become conductive via growth or interfaces with conducting polymers, an exemplary approach of modifying the silk polymer itself to conduct electricity can involve surface functionalization of the silk to modify the high content of tyrosines to sulfate groups. In some embodiments, the surface functionalization can be performed using diazonium coupling reactions (See, e.g., Murphy, A R. et al. "Modification of silk using diazonium coupling chemistry and the effects on hMSC proliferation and differentiation." (2008) Biomaterials 29:2829-2838; and U.S. App. No. US 2009/0232963 entitled "Diazonium salt modification of silk polymer" filed Aug. 15, 2008, the content of which is incorporated herein by reference). The modified tyrosines can be used as anchoring sites to where the one or more conducting polymers can be polymerized for enhanced electronic interfaces.

Silk can stabilize labile substances including, but not limited to, enzymes, antibiotics, vaccines and small molecules, even at temperatures at 60° C. over extended time frames, e.g., a period of at least 24 hours or longer, such as for days, months or years. Without wishing to be bound by theory, the unique nano-domain structures in silk, along with the high hydrophobic content of the assembled material, can provide a suitable environment to maintain function of otherwise labile materials entrained in silk devices. Further, the entrapped biological components can retain function and the release profile can be controlled based on the crystalline state of the silk matrix. See, e.g., Guziewicz, N., et al. "Lyophilized silk fibroin hydrogels for the sustained local delivery of therapeutic monoclonal antibodies." Biomaterials (2011) April; 32(10):2642-50; Lu, Q., et al. "Stabilization and release of enzymes from silk films" Macromolecular Bioscience (2010) 10(4):359-368; Lu, S., et al. "Stabilization of enzymes in silk films." Biomacromolecules (2009) 10(5):1032-1042; Pritchard, E. M., "Incorpoatin of proteinase inhibitors into silk-based delivery devices for enhanced control of degradation and drug release." Biomaterials (2011) 32(3): 909-918; Pritchard, E. et al. "Silk fibroin encapsulated powder reservoirs for sustained release of adenosine." (2010) J. Controlled Release 144(2):159-167; Szybala, C. et al. "Antiepileptic effects of silk-polymer based adenosine release in kindled rats." Experimental Neurology. (2009) 219(1):126-135; Witz, A. et al. "Silk polymer-based adenosine release: therapeutic potential for epilepsy." Biomaterials (2008) 29:3609-3616; Wang, X. et al. "Controlled release from multilayer silk biomaterial coatings to modulate vascular cell responses." Biomaterials (2008) 29(7):894-903; Wang, X. et al. "Nanolayer biomaterial coatings of silk fibroin for controlled release." J. Controlled Release (2007) 121(3):190-199; and Wang, X. et al. "Silk microspheres for encapsulation and controlled release." (2007) J. Controlled Release. 117:360-370.

Accordingly, in some embodiments, the silk matrix and/or silk body of the silk-based electrode can comprise one or more active agents (including, but not limited to one or more therapeutic agents). The active agent can be included in the silk solution prior to forming the silk matrix and/or silk body, or can be coated on a surface of the formed silk matrix and/or silk body, or can be distributed or dispersed into the formed silk matrix and/or silk body by diffusion. Methods for incorporating an active agent into the silk matrix and/or silk body of the silk matrix are described later herein.

In such embodiments, the amount of any active agent loaded into the silk matrix or silk body is effective for producing a therapeutic effect in a subject for a certain period of time, e.g., for at least about 3 days, at least about 1 week, at least about 2 weeks, at least about 3 weeks, at least about 4 weeks, at least about 2 months, at least about 3 months, at least about 4 months, at least about 5 months, at least about 6 months, at least about 9 months, at least about 12 months or longer.

As used herein, the term "therapeutic effect" refers to reducing at least one adverse effect associated with implantation of a device into a tissue, and/or at least one symptom associated with a disease or disorder to be treated with the device. For example, for a silk-based neuroprosthetic device implanted in a brain tissue, the active agent loaded therein is effective for reducing gliosis or scar formation around the implanted neuroprosthetic device by at least about 30%, at least about 40%, at least about 50%, at least about 60%, at least about 70%, at least about 80%, at least about 90% or more, as compared to the absence of the active agent. Alternatively or additionally, the active agent loaded therein is effective for reducing at least one symptom associated with a disease or disorder to be treated (or improving neurological function) by at least about 30%, at least about 40%, at least about 50%, at least about 60%, at least about 70%, at least about 80%, at least about 90% or more, as compared to the absence of the active agent.

Accordingly, in some embodiments, the active agent can be present in an amount about 0.01% (w/w) to about 90% (w/w) of the total weight (i.e., the combined weight of the silk matrix and the therapeutic agent), for example, including, about 0.01% (w/w) to about 70% (w/w), about 0.1% (w/w) to about 50% (w/w), about 1% (w/w) to about 30% (w/w), about 5% (w/w) to about 25% (w/w), or about 7.5% (w/w) to about 20 (w/w) of the total weight. In some embodiments, the therapeutic agent can be present in a silk matrix in an amount of about 0.5% (w/w) to about 20% (w/w) of the total weight. In some embodiments, the therapeutic agent can be present in a silk matrix in an amount of about 2% (w/w) to about 20% (w/w) of the total weight. In one embodiment, the therapeutic agent can be present in a silk matrix in an amount of about 1% (w/w) to about 20% (w/w) of the total weight. In one embodiment, the therapeutic agent can be present in a silk matrix in an amount of about 0.1% (w/w) to 5% (w/w) of the total weight.

Silk can stabilize labile active agent including, but not limited to, enzymes, antibiotics, vaccines and small molecules, even at temperatures at 60° C. over extended time frames, e.g., a period of at least 24 hours or longer, such as for days, months or years. Without wishing to be bound by theory, the unique nano-domain structures in silk, along with the high hydrophobic content of the assembled material, can provide a suitable environment to maintain function of otherwise labile materials entrained in silk devices. Further, the entrapped biological components can retain function and the release profile can be controlled based on the crystalline state of the silk matrix.

In some embodiments, the silk-based electrode can have a sharpened tip or tapered tip at an end for facilitating insertion or penetration into a target tissue. The sharpened tip or tapered tip can have a cross-sectional dimension of about 1 nm to about 500 µm, about 10 nm to about 250 µm, about 50 nm to about 125 µm, about 100 nm to about 100 µm, about 150 nm to about 50 µm, about 200 nm to about 10 µm, or about 300 nm to about 5 µm. In one embodiment, one end of the silk-based electrode can have a needle-like shape.

In some embodiments, a plurality of (e.g., at least 2 including 2, 3, 4, 5, 6, 7, 8, 9, 10, 20, 30, 40, 50, 60, 70, 80, 90, 100 or more) silk-based electrodes described herein can be arranged into an array to form a microelectrode array, which can provide distributed and control of recordings and/or electrical stimulation over a larger tissue area (e.g., brain tissue area).

Without wishing to be bound, some embodiments of the silk-based electrode described herein can be flexible electrodes (e.g., an electrode that is not stiff enough to penetrate a target tissue, e.g., a brain tissue). For example, the silk tube of the silk-based electrode can be formed from a low-concentration silk solution (e.g., less than about 10% w/v). In those embodiments, the flexible silk-based electrode can be further treated to form a silk-based implantable system described herein. For example, at least a portion of the flexible silk-based electrode described herein can be in contact or coated with a silk matrix described herein. The silk matrix can then provide the flexible silk-based electrode with sufficient stiffness to penetrate a target tissue and become compliant upon the penetration.

Silk Fibroin and Silk Solution for Making the Systems and/or Devices Described Herein Silk fibroin protein have unique chemical and physical properties, e.g., tunable degradation rates, controllable crystallinity due to hydrophobic beta-sheet segments—desirable diffusion barriers for entrapped drug molecules, an amino acidic nature that provides an inert microenvironment for drug encapsulation, as well as an aqueous-based material processing that is favorable for sensitive drug molecules. Silk-based biomaterials have been previously reported for their biocompatibility and biosafety for various in vivo applications, which is comparable with or superior to other biodegradable materials, such as collagen, hyaluronic acids, poly-lactic-co-glycolic acid (PLGA).

Silk is both biocompatible and biodegradable (31, 32), with tunable mechanical properties and resorption rates based on controlled crystallization of the protein (33). Silk can be processed into diverse material formats including, without limitations, fibers, films, gels and sponges using only water as a solvent and under ambient conditions (34), which is conducive to the encapsulation of sensitive therapeutics.

The utility of silk as a biomaterial for applications in the nervous system has been previously reported. For example, silk-based nerve guides can be used as scaffolds for regeneration in the peripheral nervous system (35-40). However, these silk-based nerve guides are placed into the peripheral nervous system surgically, and thus they do not rely on the silk mechanics to penetrate tissues. Silk has also been reported to support and direct the growth of various cell types from the central nervous system (41, 42). In the brain, specifically, silk has been utilized to deliver adenosine to reduce seizures in epileptic rats (43) and as a vehicle for enhancing conformal contact between a planar electrode array and the brain's surface (44). In addition, silk can be utilized to delivery a drug to modulate an immune response to silk matrix (e.g., silk films) at the brain surface.

As used herein, the term "silk fibroin" includes silkworm fibroin and insect or spider silk protein. See e.g., Lucas et al., 13 Adv. Protein Chem. 107 (1958). Any type of silk fibroin can be used according to aspects provided herein. Silk fibroin produced by silkworms, such as *Bombyx mori*, is the most common and represents an earth-friendly, renewable resource. For instance, silk fibroin used in a silk fibroin fiber can be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used. In some embodiments, silk fibroin can be derived from other sources such as spiders, other silkworms, bees, and bioengineered variants thereof. In some embodiments, silk fibroin can be extracted from a gland of silkworm or transgenic silkworms (see, e.g., WO 2007/098951).

Silk fiber generated from *Bombyx mori* silkworms generally have a tensile strength of 500 MPa and some recombinant spider silks can have achieved tenacity (maximum fiber stress) of 508 MPa, close to properties for native *N. clavipes* dragline silk (740-1200 MPa). Different processing of silk solution can improve the mechanical property of the silk fiber. By way of example only, silk solution stored at various temperatures can allow mechanical drawing to produce outstanding mechanical properties. Some of these materials exhibited strong and tough fibers such as temperature-processed fibers (e.g., produced by a molding/freezing method, e.g., as described in the Prov. Appl. No. 61/477,486 filed Apr. 20, 2012) with a diameter of approximately 0.42 mm and a modulus up to 5,900 MPa. In some embodiments, the temperature-processed fibers can be stiff enough for insertion through the dura. For example, the temperature-processed fibers remain undeformed (e.g., substantially straight) during insertion through the dura.

The silk fibroin solution can be prepared by any conventional method known to one skilled in the art. For example, *B. mori* cocoons are boiled for about 30 minutes in an aqueous solution. In one embodiment, the aqueous solution is about 0.02M $Na_2CO_3$. The cocoons are rinsed, for example, with water to extract the sericin proteins and the extracted silk is dissolved in an aqueous salt solution. Salts useful for this purpose include lithium bromide, lithium thiocyanate, calcium nitrate or other chemicals capable of solubilizing silk. In some embodiments, the extracted silk is dissolved in about 8M-12 M LiBr solution. The salt is consequently removed using, for example, dialysis.

If necessary, the solution can then be concentrated using, for example, dialysis against a hygroscopic polymer, for example, PEG, a polyethylene oxide, amylose or sericin. In some embodiments, the PEG is of a molecular weight of 8,000-10,000 g/mol and has a concentration of 25%-50%. A slide-a-lyzer dialysis cassette (Pierce, MW CO 3500) can be used. However, any dialysis system may be used. The dialysis can be performed for a time period sufficient to result in a final stock concentration of aqueous silk solution between about 6% (w/v)-about 30% (w/v). In one embodiment, the dialysis can be performed for a time period sufficient to result in a final stock concentration of aqueous silk solution of about 15% (w/v). In most cases dialysis for 2-12 hours is sufficient. See, for example, International Application No. WO 2005/012606, the content of which is incorporated herein by reference.

Alternatively, the silk fibroin solution can be produced using organic solvents. Such methods have been described, for example, in Li, M., et al., J. Appl. Poly Sci. 2001, 79, 2192-2199; Min, S., et al. Sen'I Gakkaishi 1997, 54, 85-92; Nazarov, R. et al., Biomacromolecules 2004 May-June; 5(3):718-26. For example, an exemplary organic solvent that can be used to produce a silk solution includes, but is not limited to, hexafluoroisopropanol.

A silk solution for use in making the silk matrix or silk body of the implantable system and/or device described herein can comprise fibroin at any concentration, depending on desired characteristics of the silk matrix or silk body, e.g., drug release profile and/or its solubility, e.g., in water. In some embodiments, the silk solution can comprise silk fibroin at a concentration of about 0.1% (w/v) to about 50% (w/v), about 1% (w/v) to about 40% (w/v), about 6% (w/v) to about 30% (w/v), or about 7% (w/v) to about 20% (w/v). In some embodiments, the silk solution can comprise silk fibroin at a concentration of about 10% (w/v) to about 30% (w/v). In some embodiments, the silk solution can comprise silk fibroin at a concentration greater than 5% (w/v), greater than 10% (w/v), or greater than 15% (w/v). Generally, higher silk concentration can result in a silk matrix or silk body with a higher tensile modulus.

In various embodiments, the silk fibroin can be modified for different applications and/or desired mechanical or chemical properties (e.g., to facilitate formation of a gradient of a therapeutic agent in silk fibroin matrices). One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. In some embodiments, the silk fibroin can be genetically modified to be fused with a protein, e.g., a therapeutic protein. Additionally, the silk fibroin matrix can be combined with a chemical, such as glycerol, that, e.g., affects flexibility and/or solubility of the matrix. See, e.g., WO 2010/042798, Modified Silk films Containing Glycerol.

In some embodiments, the silk solution for use in making the silk matrix or silk body of the implantable system and/or device described herein can further comprise one or more (e.g., one, two, three, four, five or more) additives, e.g., for various desired properties and/or applications. Exemplary additives can include, but are not limited to, a biopolymer, a porogen (e.g., a salt or polymeric particle), a magnetic particle, a plasmonic particle, a metamaterial, an excipient, a plasticizer (e.g., glycerol, polyvinyl alcohol, collagen, gelatin, alginate, chitosan, hyaluronic acid, polyethylene glycol, polyethylene oxide, and any combinations thereof), a detection label, and any combinations thereof. The additive(s) can be present in the silk solution at any ratio. For example, the weight ratio of the additive to silk in the silk solution can range from about 1:1000 to about 1000:1, or from about 1:100 to about 100:1, or from about 1:10 to about 10:1. In some embodiments, total amount of additives in the solution can be from about 0.1 wt % to about 70 wt %, from about 5 wt % to about 60 wt %, from about 10 wt % to about 50 wt %, from about 15 wt % to about 45 wt %, or from about 20 wt % to about 40 wt %, of the total silk fibroin in the solution.

In some embodiments, at least one additive added into the silk solution for preparing a silk matrix or silk body of the implantable system can include one or more (e.g., one, two, three, four, five or more) biopolymers and/or biocompatible polymers. Exemplary biopolymers and/or biocompatible polymers include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, chitosan, chitin, hyaluronic acid, pectin, polyhydroxyalkanoates, dextrans, and polyanhydrides, polyethylene oxide (PEO), poly (ethylene glycol) (PEG), triblock copolymers, polylysine, alginate, polyaspartic acid, sugar, tyrosine-based polymers, polyvinyl acetate, cellulose, any derivatives thereof and any combinations thereof. Other exemplary biocompatible polymers amenable to use according to the present disclosure include those described for example in U.S. Pat. Nos. 6,302,848; 6,395,734; 6,127,143; 5,263,992; 6,379,690; 5,015,476; 4,806,355; 6,372,244; 6,310,188; 5,093,489; 6,387,413; 6,325,810; 6,337,198; 6,267,776; 5,576,881; 6,245,537; 5,902,800; and 5,270,419, content of all of which is incorporated herein by reference.

In some embodiments, the silk solution can comprise particles for mechanical reinforcement when making a silk matrix or silk body. In some embodiments, the particles can include silk particles. For example, ultrafine silk particles can be added into the silk solution for forming a silk matrix or silk body, thus controlling mechanical features. Without wishing to be bound by theory, the silk particles can retain their crystallinity and are useful for matrix/body reinforcement due to interfacial compatibility, resulting in significant improvements in mechanical properties. The presence of the particles can increase the wet compression modulus and the yield strength of the silk matrix or silk body about two orders of magnitude or higher in comparison to the scaffolds without the particles. Without wishing to be bound by theory, this significant increase can be due to the high interfacial cohesion between the matrix and the particle reinforcements due to partial solubility of crystalline silk particles in a solvent (e.g., aqueous-based solvent or organic solvent such as HFIP). See, e.g., Rajkhowa, R., et al. "Reinforcing silk scaffolds with silk particles." Macromolecular Bioscience. (2010) 10(6): 599-611.

Any embodiment of the silk solution described herein for preparing the silk matrix and/or silk body of the implantable system and/or device described herein can also be used to fill the silk reservoir of the silk-based implantable device described herein. For example, the silk solution present in the silk reservoir of the silk-based implantable device described herein can also include at least one active agent, and/or at least one additive described herein. However, in some embodiments, the concentration of the silk solution stored in the silk reservoir can be lower than the concentration of the silk solution used to make the silk body. In some embodiments, the silk solution stored in the silk reservoir need not any particles for mechanical reinforcement. In some embodiments, the silk solution stored in the silk reservoir can have a concentration that would allow the silk solution remaining in a solution or fluid state after implantation such that it can be discharged through the through holes on an electrode surface to form a silk coating thereon. However, the concentration of the silk solution stored in the silk reservoir should not be so low that it can compromise the durability of the silk coating.

Exemplary Therapeutic Agents and Amounts Thereof in a Silk Matrix or Silk Body

Depending on various applications of the implantable systems and/or devices described herein, different types of the active agent can be present in the silk matrix or silk body, e.g., by encapsulation and/or coating. Without wishing to be bound, for example, the silk matrix or silk body can comprise one or more active agents, including, but not limited to, therapeutic agents, imaging agents or any combinations thereof.

In some embodiments, one or more imaging agents can be included in a silk matrix or silk body. Examples of imaging agents can include, but are not limited to, dyes, fluorescent agents, radiological imaging agents, any art-recognized contrast agents for imaging tissues and/or organs, and any combinations thereof. Fluorescent agents are well known in the art. Examples of fluorescent agents can include, but are not limited to, fluoresceinisothiocyanato-dextran (FITC-dextran), ruthenium based dye, or platinum porphyrin, or a mixture thereof.

As used herein, the term "therapeutic agent" means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a therapeutic effect, for example deoxyribonucleic acid (DNA), ribonucleic acid (RNA), or mixtures or combinations thereof.

The term "therapeutic agent" also includes an agent that is capable of providing a local or systemic biological, physiological, or therapeutic effect in the biological system to which it is applied. For example, the therapeutic agent can act to control infection or inflammation, enhance cell growth and tissue regeneration, suppress cell proliferation, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk matrix can contain combinations of two or more therapeutic agents.

A therapeutic agent can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary therapeutic agents include, but are not limited to, those found in *Harrison's Principles of Internal Medicine*, $13^{th}$ Edition, Eds. T. R. Harrison et al. McGraw-Hill N.Y., NY; Physicians Desk Reference, $50^{th}$ Edition, 1997, Oradell N.J., Medical Economics Co.; Pharmacological Basis of Therapeutics, $8^{th}$ Edition, Goodman and Gilman, 1990; United States Pharmacopeia, The National Formulary, USP XII NF XVII, 1990, the complete contents of all of which are incorporated herein by reference.

Therapeutic agents include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopres sin analogue, an antiarrhythmic agent, an anti-parkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopres sin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

In some embodiments, the active agent to be included in a silk matrix or silk body can include an agent (including a therapeutic agent) that can promote tissue growth, reduce scar formation, control inflammation at a penetration site (e.g., reducing inflammation at a penetration site), or any combinations thereof. Examples of anti-inflammatory agents and/or scar-reducing agents can include, but are not limited to, dexamethasone (23-26), alpha-MSH (27), cell cycle inhibitor flavopiridol (28), neural adhesion molecule L1 (29), and any combinations thereof.

In some embodiments, the active agent to be included in a silk matrix or silk body can include at least one, at least two, at least three, at least four, at least five or more gliosis-modulating agents (e.g., an agent that can reduce or inhibit proliferation of astrocytes in damaged areas of the central nervous system). An exemplary gliosis-modulating agent can include cytarabine (or Arabinofuranosyl Cytidine). Additionally or alternatively, the active agent to be included in a silk matrix or silk body can include at least one, at least two, at least three, at least four, at least five or more antibiotics. In some embodiments, the antibiotics can include, but are not limited to, penicillin.

As noted above, any therapeutic agent can be included in a silk matrix or silk body, e.g., by encapsulation and/or coating. In some embodiments, it is desirable to include in a silk matrix material to promote the growth of the agent (for biological agents), promote the functionality of the agent after it is released from the encapsulation, or increase the agent's ability to survive or retain its efficacy during the encapsulation period. Materials known to promote cell growth include cell growth media, such as Dulbecco's Modified Eagle Medium (DMEM), fetal bovine serum (FBS), non-essential amino acids and antibiotics, and growth and morphogen factors such as basic fibroblast growth factor (bFGF), transforming growth factors (TGFs), Vascular endothelial growth factor (VEGF), insulin-like growth factor (IGF-I), bone morphogenetic growth factors (BMPs), nerve growth factors and related proteins.

Additional options for delivery via the silk matrix or silk body described herein can include DNA, siRNA, antisense, plasmids, liposomes and related systems for delivery of genetic materials; antibodies and antigen binding fragment thereof; peptides and proteins to active cellular signaling cascades; peptides and proteins to promote mineralization or related events from cells; adhesion peptides and proteins to improve gel-tissue interfaces; antimicrobial peptides; and proteins and related compounds.

In some embodiments, the therapeutic agent(s) for use in the present disclosure include, but are not limited to, those requiring relatively frequent dosing. For example, those used in the treatment of chronic disorders or conditions.

In some embodiments, the therapeutic agent is a cell, e.g. a biological cell. In such embodiments, the cells can be distributed within a silk matrix by incubating the silk matrix in a cell suspension, where the cells can migrate from the suspension into the pores of the silk matrix. Cells amenable to be incorporated into the silk matrix include, but are not limited to, stem cells (embryonic stem cells, mesenchymal stem cells, bone-marrow derived stem cells and hematopoietic stem cells), chrondrocytes progenitor cells, pancreatic progenitor cells, myoblasts, fibroblasts, keratinocytes, neuronal cells, glial cells, astrocytes, pre-adipocytes, adipocytes, vascular endothelial cells, hair follicular stem cells, endothelial progenitor cells, mesenchymal cells, neural stem cells and smooth muscle progenitor cells.

In some embodiments, the cell is a genetically modified cell. A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., *Science*, 2007, 318, 1917-1920 and Takahashi K. et. al., *Cell*, 2007, 131, 1-12).

Cells useful for incorporation into the silk matrix can come from any source, for example human, rat or mouse. Human cells include, but are not limited to, human cardiac myocytes-adult (HCMa), human dermal fibroblasts-fetal (HDF-f), human epidermal keratinocytes (HEK), human mesenchymal stem cells-bone marrow, human umbilical mesenchymal stem cells, human hair follicular inner root sheath cells, human umbilical vein endothelial cells (HU- VEC), and human umbilical vein smooth muscle cells (HUVSMC), human endothelial progenitor cells, human myoblasts, human capillary endothelial cells, and human neural stem cells.

Exemplary rat and mouse cells include, but not limited to, RN-h (rat neurons-hippocampal), RN-c (rat neurons-cortical), RA (rat astrocytes), rat dorsal root ganglion cells, rat neuroprogenitor cells, mouse embryonic stem cells (mESC) mouse neural precursor cells, mouse pancreatic progenitor cells mouse mesenchymal cells and mouse endodermal cells.

In some embodiments, tissue culture cell lines can be used in the silk matrix described herein. Examples of cell lines include, but are not limited to, C166 cells (embryonic day 12 mouse yolk), C6 glioma Cell line, HL1 (cardiac muscle cell line), AML12 (nontransforming hepatocytes), HeLa cells (cervical cancer cell line) and Chinese Hamster Ovary cells (CHO cells).

An ordinary skill artisan in the art can locate, isolate and expand such cells. In addition, the basic principles of cell culture and methods of locating, isolation and expansion and preparing cells for tissue engineering are described in "Culture of Cells for Tissue Engineering" Editor(s): Gordana Vunjak-Novakovic, R. Ian Freshney, 2006 John Wiley & Sons, Inc., and Heath C. A., *Trends in Biotechnology*, 2000, 18, 17-19, content of both of which is herein incorporated by reference in its entirety.

Generally, any amount of the therapeutic agent can be dispersed or encapsulated in the silk matrix or silk body, depending on a number of factors, including, but not limited to, desirable release profile (e.g., release rates and/or duration), properties (e.g., half-life and/or molecular size) and/or potency of the therapeutic agent, severity of a subject's disease or disorder to be treated, desirable administration schedule, loading capacity of the silk matrix, and any combinations thereof. For example, in some embodiments, a therapeutic agent can be present in a silk matrix or silk body in an amount of about 1 ng to about 100 mg, about 500 ng to about 90 mg, about 1 μg to about 75 mg, about 0.01 mg to about 50 mg, about 0.1 mg to about 50 mg, about 1 mg to about 40 mg, about 5 mg to about 25 mg. In some embodiments, a therapeutic agent can be present in a silk matrix or silk body in an amount of about 0.01% (w/w) to about 90% (w/w) of the total weight (i.e., the combined weight of the silk matrix or silk body and the therapeutic agent), for example, including, about 0.01% (w/w) to about 70% (w/w), about 0.1% (w/w) to about 50% (w/w), about 1% (w/w) to about 30% (w/w), about 5% (w/w) to about 25% (w/w), or about 7.5% (w/w) to about 20 (w/w) of the total weight. In some embodiments, the therapeutic agent can be present in a silk matrix or silk body in an amount of about 0.5% (w/w) to about 20% (w/w) of the total weight. In some embodiments, the therapeutic agent can be present in a silk matrix or silk body in an amount of about 2% (w/w) to about 20% (w/w) of the total weight. In one embodiment, the therapeutic agent can be present in a silk matrix or silk body in an amount of about 0.1% (w/w) to 5% (w/w) of the total weight.

Without wishing to be bound by theory, the duration of a therapeutic effect on a target site to be treated is generally correlated with how long an amount of the therapeutic agent delivered to the target site can be maintained at a therapeutically effective amount. Thus, in some embodiments, the implantable system and/or device described herein can comprise a therapeutic agent dispersed or encapsulated in a silk matrix, wherein the therapeutic agent is present in an amount sufficient to maintain a therapeutically effective amount thereof delivered to treat a target site, upon implantation, over a specified period of time, e.g., over more than 1 week, or more than 1 month.

The term "therapeutically effective amount" as used herein refers to an amount of a therapeutic agent which is effective for producing a beneficial or desired clinical result in at least a sub-population of cells in a subject at a reasonable benefit/risk ratio applicable to any medical treatment. For example, a therapeutically effective amount delivered to a target site is sufficient to, directly or indirectly, produce a statistically significant, measurable therapeutic effect as defined herein. By way of example only, the therapeutically effective amount delivered to a target site for treatment is sufficient to reduce at least one symptom or marker associated with the disease or disorder to be treated (e.g., but not limited to, cancer such as brain cancer, cardiovascular diseases such as cardiac arrhythmia, neurodegenerative diseases such as Alzheimer's disease) by at least about 10%, at least about 20%, at least about 30%, at least about 40%, at least about 50%, at least about 60% or higher, as compared to absence of the therapeutic agent. In some embodiments, the therapeutically effective amount delivered to a target site for treatment is sufficient to reduce at least one symptom or marker associated with the disease or disorder to be treated (e.g., but not limited to, cancer such as brain cancer, cardiovascular diseases such as cardiac arrhythmia, neurodegenerative diseases such as Alzheimer's disease) by at least about 60%, at least about 70%, at least about 80% or higher, as compared to absence of the therapeutic agent. In some embodiments, the therapeutically effective amount delivered to a target site is sufficient to reduce at least one symptom or marker associated with the disease or disorder to be treated (e.g., but not limited to, cancer such as brain cancer, cardiovascular diseases such as cardiac arrhythmia, neurodegenerative diseases such as Alzheimer's disease) by at least about 80%, at least about 90%, at least about 95%, at least about 98%, at least about 99%, up to and including 100%, as compared to absence of the therapeutic agent.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. Furthermore, therapeutically effective amounts will vary, as recognized by those skilled in the art, depending on the specific disease treated, the route of administration, the excipient selected, and the possibility of combination therapy. In some embodiments, the therapeutically effective amount can be in a range between the ED50 and LD50 (a dose of a therapeutic agent at which about 50% of subjects taking it are killed). In some embodiments, the therapeutically effective amount can be in a range between the ED50 (a dose of a therapeutic agent at which a therapeutic effect is detected in at least about 50% of subjects taking it) and the TD50 (a dose at which toxicity occurs at about 50% of the cases). In alternative embodiments, the therapeutically effective amount can be an amount determined based on the current dosage regimen of the same therapeutic agent administered in a non-silk matrix. For example, an upper limit of the therapeutically effective amount can be based on a concentration or an amount of the therapeutic agent delivered to a target site, on the day of administration with the current dosage of the therapeutic agent in a non-silk matrix; while the lower limit of the therapeutically effective amount can be based on a concentration or an amount of the therapeutic agent delivered to a target site, on the day at which a fresh dosage of the therapeutic agent in a non-silk matrix is required.

As used herein, the term "maintain" is used in reference to sustaining a concentration or an amount of a therapeutic agent delivered to a target site at least about or above the therapeutically effective amount over a specified period of time. In some embodiments, the term "maintain" as used herein can refer to keeping the concentration or amount of a therapeutic agent at an essentially constant value over a specified period of time. In some embodiments, the term "maintain" as used herein can refer to keeping the concentration or amount of a therapeutic agent within a range over a specified period of time. For example, the concentration or amount of a therapeutic agent delivered to a target site can be maintained within a range between about the ED50 and about the LD50 or between about the ED50 and about the TD50 over a specified period of time. In such embodiments, the concentration or amount of a therapeutic agent delivered to a target site can vary with time, but is kept within the therapeutically effective amount range for at least 90% of the specified period of time (e.g., at least about 95%, about 98%, about 99%, up to and including 100%, of the specified period of time).

In some embodiments, the therapeutic agent can be present in an amount sufficient to maintain a therapeutically effective amount thereof delivered to a target site, upon implantation, over a period of more than 1 week, including, e.g., at least about 2 weeks, at least about 3 weeks, at least about 1 month, at least about 2 months, at least about 3 months, at least about 6 months, at least about 12 months or longer. Such amounts of the therapeutic agent present in a silk matrix or silk body can be generally smaller, e.g., at least about 10% smaller, than the amount of the therapeutic agent present in the current dosage of the treatment regimen (i.e., without silk matrix) required for producing essentially the same therapeutic effect. Accordingly, a silk matrix or silk body can comprise the therapeutic agent in an amount which is less than the amount recommended for one dosage of the therapeutic agent. For example, if the recommended dosage of the therapeutic agent is X amount then the silk matrix or silk body can comprise a therapeutic agent in an amount of about 0.9×, about 0.8×, about 0.7×, about 0.6×, about 0.5×, about 0.4×, about 0.3×, about 0.2×, about 0.1× or less. Without wishing to be bound by a theory, this can allow administering a lower dosage of the therapeutic agent in a silk matrix or silk body to obtain a therapeutic effect which is similar to when a higher dosage is administered without the silk matrix.

In some embodiments, an amount of the therapeutic agent dispersed or encapsulated in a silk matrix or silk body can be more than the amount generally recommended for one dosage of the same therapeutic agent administered for a particular indication. Administration of a therapeutic agent in solution does not generally allow controlled and sustained release. Thus, release rate of a therapeutic agent in solution can generally create a higher initial burst and/or overall faster release kinetics than that of the same amount of the therapeutic agent loaded in silk matrix or silk body. However, the silk matrix can act as a depot such that an amount of the therapeutic agent loaded in a silk matrix or silk body can be higher than the amount generally recommended for one dosage of the same therapeutic agent and release the therapeutic agent over a period of time, thus providing a longer therapeutic effect with lower frequency of administration. Accordingly, if the recommended dosage of the therapeutic agent is X amount then the silk matrix can encapsulate a therapeutic agent in an amount of about 1.25×, about 1.5×, about 1.75×, about 2×, about 2.5×, about 3×, about 4×, about 5×, about 6×, about 7×, about 8×, about 9×, about 10× or more. Without wishing to be bound by a theory, this can allow administering the therapeutic agent in a silk matrix or silk body to obtain a therapeutic effect which is similar to one obtained with multiple administration of the therapeutic agent administered without the silk matrix or silk body described herein.

In some embodiments, an amount of the therapeutic agent encapsulated or dispersed in a dosage of the silk matrix or silk body can be essentially the same amount recommended for one dosage of the therapeutic agent. For example, if the recommended dosage of the therapeutic agent is X amount, then the silk-based composition can comprise about X amount of the therapeutic agent. Without wishing to be bound by a theory, this can allow less frequent administration of the therapeutic agent to obtain a therapeutic effect over a longer period of time.

As used herein, the term "sustained delivery" refers to continual delivery of a therapeutic agent in vivo or in vitro over a period of time following administration. For example, sustained release can occur over a period of at least about 3 days, at least about a week, at least about two weeks, at least about three weeks, at least about four weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months or longer. In some embodiments, the sustained release can occur over a period of more than one month or longer. In some embodiments, the sustained release can occur over a period of at least about three months or longer. In some embodiments, the sustained release can occur over a period of at least about six months or longer. In some embodiments, the sustained release can occur over a period of at least about nine months or longer. In some embodiments, the sustained release can occur over a period of at least about twelve months or longer.

Sustained delivery of the therapeutic agent in vivo can be demonstrated by, for example, the continued therapeutic effect of the agent over time. Alternatively, sustained delivery of the therapeutic agent can be demonstrated by detecting the presence or level of the therapeutic agent in vivo over time. The release rate of a therapeutic agent can be adjusted by a number of factors such as silk matrix composition and/or concentration, porous property of the silk matrix or silk body, molecular size of the therapeutic agent, and/or interaction of the therapeutic agent with the silk matrix or silk body. For example, if the therapeutic agent has a higher affinity with the silk matrix or silk body, the release rate is usually slower than the one with a lower affinity with the silk matrix or silk body. Additionally, when a silk matrix or silk body has larger pores, the encapsulated therapeutic agent is generally released from the silk matrix or silk body faster than from a silk matrix or silk body with smaller pores.

In some embodiments, the therapeutic agent can be present in an amount to provide a release profile of the therapeutic agent from the silk matrix or silk body such that the amount of the therapeutic agent delivered to a target site is maintained within a therapeutically effective amount range over a period of time. In some embodiments, the therapeutic agent can be present in an amount to provide a release profile of the therapeutic agent with release rates ranging from about 0.01 ng/day to about 1000 mg/day, from about 0.1 ng/day to about 500 mg/day, or from about 1 ng/day to about 250 mg/day over a period of time. Without wishing to be bound by theory, upon implantation of the implantable system and/or device described herein, there can be an initial spike in the amount of the therapeutic agent released from the silk matrix or silk body to a target site, and then the release rate of the therapeutic agent from the silk matrix or silk body can decrease over a period of time. Thus, the therapeutic agent can be released initially at a rate as high as mg/day, and later released in a slower rate, e.g., in µg/day or ng/day. Accordingly, in some embodiments, the therapeutic agent can be present in an amount to provide a release profile such that daily release of the therapeutic agent can range from about 1 ng/day to about 1000 mg/day. For example, amount released can be in a range with a lower limit of from 1 to 1000 (e.g., every integer from 1 to 1000) and upper limit of from 1 to 1000 (e.g. every integer from 1 to 1000), wherein the lower and upper limit units can be selected independently from ng/day, µg/day, mg/day, or any combinations thereof.

In some embodiments, daily release can vary from about 1 µg/day to about 10 mg/day, from about 0.25 µg/day to about 2.5 mg/day, or from about 0.5 µg/day to about 5 mg/day. In some embodiments, daily release of the therapeutic agent can range from about 100 ng/day to 1 mg/day, for example, or about 500 ng/day to 5 mg/day, or about 100 µg/day.

Stated another way, the therapeutic agent can be released from the silk matrix or silk body at a rate such that at least about 5%, including, e.g., at least about 10%, at least about 20%, at least about 30%, at least about 40%, at least about 50%, at least about 60%, at least about 70%, at least about 80%, at least about 90% or more, of the therapeutic agent initially present in the silk matrix or silk body can be released over a period of about 3 days, about 1 week, about 10 days, about 20 days, about 1 month, about 2 months, about 3 months, about 4 months, about 5 months, about 6 months, about 7 months, about 8 months, about 9 months, about 10 months, about 11 months, about 12 months or longer. In some embodiments, the therapeutic agent can be released from the silk matrix or silk body at a rate such that about 5-30% of the therapeutic agent initially present in the silk matrix can be released over a period of about 3-20 days. In some embodiments, the therapeutic agent can be released from the silk matrix or silk body at a rate such that about 40-90% of the therapeutic agent initially present in the silk matrix or silk body can be released over a period of about 3-30 days.

The release profiles of the therapeutic agent from the silk matrix or silk body of the implantable system and/or device described herein can be modulated by a number of factors such as amounts and/or molecular size of the therapeutic agents loaded in a silk matrix or silk body, porosity of the silk matrix or silk body, amounts of silk fibroin in a silk matrix or silk body and/or contents of beta-sheet conformation structures in a silk matrix or silk body, binding affinity of the therapeutic agent to a silk matrix or silk body, and any combinations thereof.

In addition, silk matrix or silk body can stabilize the bioactivity of a therapeutic agent under a certain condition, e.g., under an in vivo physiological condition. See, e.g., U.S. Provisional Application No. 61/477,737, the content of which is incorporated herein by reference, for additional details on compositions and methods of stabilization of active agents. Accordingly, in some embodiments, encapsulating a therapeutic agent in a silk matrix or silk body can increase the in vivo half-life of the therapeutic agent. For example, in vivo half-life of a therapeutic agent dispersed or encapsulated in a silk matrix or silk body can be increased by at least about 5%, at least about 10%, at least about 15%, at least about 20%, at least about 30%, at least about 40%, at least about 50%, at least about 60%, at least about 90%, at least about 1-fold, at least about 1.5-folds relative to the therapeutic agent without the silk matrix or silk body. Without wishing to be bound by theory, an increase in in vivo half-life of a therapeutic agent dispersed or encapsulated in a silk matrix or silk body can provide a longer therapeutic effect. Stated another way, an increase in in vivo half-life of a therapeutic agent dispersed or encapsulated in a silk matrix or silk body can allow loading of a smaller amount of the therapeutic agent for the same duration of therapeutic effect.

In some embodiments, at least one therapeutic agent can be dispersed or encapsulated in the silk matrix or silk body. In some embodiments, at least two or more therapeutic agents can be dispersed or encapsulated in the silk matrix or silk body. The therapeutic agent can be in any form suitable for a particular method to be used for encapsulation and/or dispersion. For example, the therapeutic agent can be in the form of a solid, liquid, or gel. In some embodiments, the therapeutic agent can be in the form of a powder or a pellet. In some embodiments, the therapeutic agent can be dispersed or encapsulated in a silk solution before forming the silk matrix or silk body. In some embodiments, the therapeutic agent can be dispersed or encapsulated in a silk solution after forming the silk matrix or silk body. For example, the therapeutic agent can be dispersed homogeneously or heterogeneously within the silk matrix or silk body, or dispersed in a gradient, e.g., using the carbodiimide-mediated modification method described in the U.S. Patent Application No. US 2007/0212730. In some embodiments, the therapeutic agent can be coated on a surface of the silk matrix or silk body, e.g., via diazonium coupling reaction (see, e.g., U.S. Patent Application No. US 2009/0232963), and/or avidin-biotin interaction (see, e.g., International Application No.: WO 2011/011347). In some embodiments, the therapeutic agent can be encapsulated in the silk matrix or silk body, e.g., by blending the therapeutic agent into a silk solution before processing into a desired material state, e.g., a silk tube. In some embodiments, the therapeutic agent can be present in a form of a fusion protein with silk protein, e.g., by genetically engineering silk to generate a fusion protein comprising the therapeutic agent.

In some embodiments, the therapeutic agent can be dispersed or encapsulated in a silk matrix or silk body after the silk matrix or silk body is formed, e.g., by placing the formed silk matrix or silk body in a therapeutic agent solution and allowing the therapeutic agent diffuse into the silk matrix or silk body over a period of time. In some embodiments, the silk matrix or silk body can be optionally hydrated before loading with the therapeutic agent. For example, the silk matrix or silk body can be incubated in deionized water until completely hydrated.

Embodiments of the various aspects described herein can be illustrated by the following numbered paragraphs.

1. A silk-based implantable system comprising an electrical component, wherein at least a portion of the electrical component is in contact with a silk matrix, the silk matrix providing the electrical component with sufficient stiffness to penetrate a target tissue and becoming compliant upon the penetration.
2. The silk-based implantable system of paragraph 1, wherein the electrical component is at least part of a pre-formed implantable device, wherein the pre-formed implantable device without the silk matrix deforms during the penetration.

3. The silk-based implantable system of paragraph 2, wherein the pre-formed implantable device is a neuroprosthetic device.

4. The silk-based implantable system of paragraph 3, wherein the neuroprosthetic device includes a brain penetrating electrode, a shunt, or a nerve guide.

5. The silk-based implantable system of paragraph 1, wherein the electrical component is patterned on the silk matrix.

6. The silk-based implantable system of any of paragraphs 1-5, wherein the electrical component includes a silk-based electrode.

7. The silk-based implantable system of any of paragraphs 1-6, wherein the silk matrix becomes compliant upon the penetration by hydration of the silk matrix.

8. The silk-based implantable system of paragraph 7, wherein the silk matrix becomes compliant upon the penetration to provide conformal contact between the electrical component and a surface of the target tissue.

9. The silk-based implantable system of any of paragraphs 1-8, wherein at least one side of the electrical component is coated with the silk matrix.

10. The silk-based implantable system of any of paragraphs 1-9, wherein the silk matrix comprises an active agent.

11. The silk-based implantable system of paragraph 10, wherein the active agent promotes tissue growth, controls inflammation at a site of the penetration, or both.

12. The silk-based implantable system of any of paragraphs 10-11, wherein the active agent includes a gliosis-modulating agent.

13. The silk-based implantable system of any of paragraphs 1-12, wherein the silk matrix has a thickness of about 1 µm to about 1000 µm.

14. The silk-based implantable system of any of paragraphs 1-13, wherein the silk matrix increases a buckling force of the electrical component or the implantable device by at least about 2-fold, as compared to the absence of the silk matrix.

15. The silk-based implantable system of any of paragraphs 1-14, wherein the silk matrix reduces gliosis around the electrical component or the implantable device by at least about 10%, as compared to the absence of the silk matrix.

16. A method of inserting a flexible or soft implantable device into a target tissue comprising providing a silk-based implantable system of any of paragraph 1-15.

17. A method of reducing gliosis around a neuroprosthetic device implanted in a brain tissue comprising providing a silk-based implantable system of any of paragraphs 1-15.

18. A method of improving long-term functionality of a neuroprosthetic device implanted in a brain tissue comprising providing a silk-based implantable system of any of paragraphs 1-15.

19. The method of any of paragraphs 16-18, wherein the silk matrix is in a dry state before implantation.

20. A silk-based implantable device comprising a silk body with at least one electrically-conducting component.

21. The device of paragraph 20, wherein the silk body is a silk tube with said at least one electrically-conducting component formed on at least a portion of a lateral surface of the silk tube.

22. The device of paragraph 21, wherein the silk tube is filled with silk solution.

23. The device of paragraph 20, wherein the silk body comprises a first silk layer and a second silk layer, at least one of the first and the second silk layer comprising at least one electrically-conducting component formed on at least a portion of a surface of the silk layer.

24. The device of paragraph 23, wherein between the first and the second silk layer includes silk particles or powders.

25. The device of paragraph 24, wherein the silk particles or powders are lyophilized.

26. The device of paragraph 25, wherein the silk particles or powders become a silk solution upon contact with a fluid.

27. The device of any of paragraphs 20-26, wherein the electrically-conducting component includes one or more through holes such that the silk solution present in the silk tube or between the silk layers is able to be discharged onto a surface of the electrically-conducting component.

28. The device of paragraph 27, wherein the silk solution on the surface of the electrically-conducting component forms a gel upon application of a first voltage through the electrically-conducting component, and turns to a solution upon application of a second voltage with a polarity opposite to the first voltage.

29. The device of any of paragraphs 20-28, wherein the electrical conducting component includes a metal.

30. The device of paragraph 29, wherein the metal is a transition metal or a noble metal.

31. The device of paragraph 30, wherein the transition metal includes silicon.

32. The device of paragraph 30, wherein the noble metal is selected from a group consisting of gold, platinum, titanium, and any combinations thereof.

33. The device of any of paragraphs 20-32, wherein the electrical conducting component includes silk modified to conduct electricity.

34. The device of paragraph 33, wherein the silk is functionalized by modifying a tyrosine of the silk protein to a sulfate group followed by polymerization of the modified tyrosine with a conducting polymer.

35. The device of paragraph 33 or 34, wherein the silk is doped with a conductive material.

36. The device of paragraph 35, wherein the conductive material is selected from the group consisting of gold nanoparticles, carbon nanotubes, graphene, and a conducting polymer.

37. The device of paragraph 36, wherein the conducting polymer includes polyethylenedioxythiophene (PEDOT), polypyrrole-based conductive polymer, copolymers of thiophenes and polypyrroles, copolymers of poly-lactide and polyaniline, or any combinations thereof.

38. The device of any of paragraphs 20-37, wherein the silk-based implantable device is adapted for use as an implantable brain penetrating electrode.

39. The device of paragraph 38, wherein the electrode has a diameter of less than 2 mm.

40. The device of paragraph 38 or 39, wherein the electrode has a tensile strength of at least about 2 MPa when the silk body is in a dry state.

41. The device of any of paragraphs 38-40, wherein the electrode has a shear modulus of less than about 200 kPa upon contact of the silk body with a fluid.

42. The device of any of paragraphs 20-41, wherein the silk body comprises an active agent.

43. A method of regenerating a silk coating on a surface of a device comprising providing the silk-based device of any of paragraphs 20-42, wherein the silk solution discharged onto the surface of the electrically-conducting component forms a gel upon application of a first voltage through the electrically-conducting component, and turns to a solution upon application of a second voltage with a polarity opposite to the first voltage.

44. A method of reducing biofouling of a device comprising providing the silk-based device of any of paragraphs 20-42, wherein the silk solution discharged onto the surface of the electrically-conducting component forms a gel upon application of a first voltage through the electrically-conducting component, and turns to a solution upon application of a second voltage with a polarity opposite to the first voltage.
45. The method of paragraph 43 or 44, wherein the device is placed in vivo or in situ.
46. The method of any of paragraphs 43-45, wherein the first voltage and the second voltage is at least about 1.2V.
47. The method of paragraph 46, wherein the first voltage and the second voltage is about 5 V to about 50 V.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "flexible" or "soft" is generally used herein in reference to a mechanical property of an implantable device. For example, in some embodiments, a flexible or soft implantable device can refer to an implantable device being not stiff enough to penetrate into a target tissue. In some embodiments, the term "flexible" or "soft" is used to refer to a mechanical state of an implantable device. For example, an implantable device becoming flexible or softer can refer to the implantable device being compliant with a target tissue to be penetrated.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

The term "nucleic acids" used herein refers to polynucleotides such as deoxyribonucleic acid (DNA), and, where appropriate, ribonucleic acid (RNA), polymers thereof in either single- or double-stranded form. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985), and Rossolini, et al., Mol. Cell. Probes 8:91-98 (1994)). The term "nucleic acid" should also be understood to include, as equivalents, derivatives, variants and analogs of either RNA or DNA made from nucleotide analogs, and, single (sense or antisense) and double-stranded polynucleotides.

The term "short interfering RNA" (siRNA), also referred to herein as "small interfering RNA" is defined as an agent which functions to inhibit expression of a target gene, e.g., by RNAi. An siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense 60 strand and/or the antisense strand. The term "siRNA" includes duplexes of two separate strands, as well as single strands that can form hairpin structures comprising a duplex region.

The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

The term "enzymes" as used here refers to a protein molecule that catalyzes chemical reactions of other substances without it being destroyed or substantially altered upon completion of the reactions. The term can include naturally occurring enzymes and bioengineered enzymes or mixtures thereof. Examples of enzyme families include kinases, dehydrogenases, oxidoreductases, GTPases, carboxyl transferases, acyl transferases, decarboxylases, transaminases, racemases, methyl transferases, formyl transferases, and α-ketodecarboxylases.

The term "vaccines" as used herein refers to any preparation of killed microorganisms, live attenuated organisms, subunit antigens, toxoid antigens, conjugate antigens or other type of antigenic molecule that when introduced into a subjects body produces immunity to a specific disease by causing the activation of the immune system, antibody formation, and/or creating of a T-cell and/or B-cell response. Generally vaccines against microorganisms are directed toward at least part of a virus, bacteria, parasite, mycoplasma, or other infectious agent.

As used herein, the term "aptamers" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. Methods for selecting aptamers for binding to a molecule are widely known in the art and easily accessible to one of ordinary skill in the art.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as portions of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

The expression "linear antibodies" refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. (The Pharmacology of Monoclonal Antibodies, vol. 113, Rosenburg and Moore eds., Springer-Verlag, New York, pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. (EP 404,097; WO 93/11161; Hollinger et ah, Proc. Natl. Acad. Sd. USA, P0:6444-6448 (1993)).

The term "antibiotics" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to, penicillins, cephalosporins, penems, carbapenems, monobactams, aminoglycosides, sulfonamides, macrolides, tetracyclines, lincosides, quinolones, chloramphenicol, vancomycin, metronidazole, rifampin, isoniazid, spectinomycin, trimethoprim, sulfamethoxazole, and the like.

As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

The term "immunogen" refers to any substance, e.g., vaccines, capable of eliciting an immune response in an organism. An "immunogen" is capable of inducing an immunological response against itself on administration to a subject. The term "immunological" as used herein with respect to an immunological response, refers to the development of a humoral (antibody mediated) and/or a cellular (mediated by antigen-specific T cells or their secretion products) response directed against an immunogen in a recipient subject. Such a response can be an active response induced by administration of an immunogen or immunogenic peptide to a subject or a passive response induced by administration of antibody or primed T-cells that are directed towards the immunogen. A cellular immune response is elicited by the presentation of polypeptide epitopes in association with Class I or Class II MHC molecules to activate antigen-specific CD4+ T helper cells and/or CD8+ cytotoxic T cells. Such a response can also involve activation of monocytes, macrophages, NK cells, basophils, dendritic cells, astrocytes, microglia cells, eosinophils or other components of innate immunity.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used interchangeably herein, the terms "essentially" and "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "essentially" means a proportion of at least about 90%, at least about 95%, at least about 98%, at least about 99% or more, or any integer between 90% and 100%. In some embodiments, the term "essentially" can include 100%.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1: Exemplary Materials and Methods

Preparation of Silk Solution.

Silk solution was prepared from *Bombyx mori* silkworm cocoons according to the procedures described in previously-reported studies (35-37). Cocoons of *B. mori* silkworm silk were supplied by Tajima Shoji Co. (Yokohama, Japan). Briefly, the cocoons were degummed in a boiling 0.02 □M Na2CO3 (Sigma-Aldrich, St. Louis, Mo.) solution for 15 min. The fibroin extract was then rinsed three times in Milli-Q water, dissolved in a 9.3M LiBr solution yielding a 20% w/v solution, and subsequently dialyzed (MWCO 3,500 kDa) against distilled water for 2 days to obtain regenerated aqueous silk fibroin solution (ca. 8% w/v). The silk solution was concentrated to 15% w/v by dialysis overnight.

Fabrication of Electrodes.

Flexible electrodes (e.g., flexible cortical electrodes) could be fabricated by any standard MEMS fabrication techniques known in the art. In some embodiments, any art-recognized flexible electrodes can be used in the systems, devices and/or methods described herein. In some embodiments, any commercially-available flexible electrodes can be used.

Coating of Electrodes.

Flat polydimethylsiloxane (PDMS) molds were prepared using two different techniques. For a rapid prototyping approach, 3-5 mm of Sylgard 184 (Dow Corning Corp., Midland, Mich.) was cast on petri dishes. Upon curing overnight at 60° C., the PDMS was cut into molds of varying design using a commercial laser cutter. PDMS molds were also prepared using conventional soft lithography microfabrication techniques (45), which allowed for finer control of edge morphology and features. A dissecting microscope was used to manually align the electrodes on the PDMS molds. The electrodes were coated by dipping the head of a pin into 15% w/v aqueous silk solution and drawing the bead of silk down the mold and electrode shank from the base to the tip, as a modification of our layer-by-layer technique (Wang et al., 2005). Coatings were allowed to dry for 15 minutes before applying another layer.

Microscopy.

Coated probes were imaged using the 10× objective on a Zeiss Axiovert 40 CFL (Carl Zeiss AG, Germany) microscope. Dimensions for both 3 and 6 layer coatings of silk fibroin were measured with QCapture Pro software. Coated probes could be also imaged using scanning electron microscopy.

Buckling Force Test.

Coated and uncoated probes were tested in ambient conditions to determine their buckling force (the maximum force exerted by the probes when pinned and loaded in a vertical orientation). This characterization was chosen to mimic the type of loading experienced by the electrodes during insertion into the brain. A custom clamping mechanism was fabricated to fix the probes to the crosshead of an Instron 3366 mechanical testing frame. Samples were lowered at a rate of 0.5 mm/min onto the weigh plate of a Mettler-Toledo MS2045/03 analytical balance. The balance was capable of reading mass to the 10th of a milligram, allowing milli-Newton forces to be recorded with custom software that interfaced with the scale.

Euler's fixed-pin beam buckling equation (10, 12):

$$F_b = \frac{\Pi^2 E_{silk} \frac{1}{12}(bh^3)}{(0.7L)^2}$$

was utilized to fit a curve to the measured buckling force and probe thicknesses using nonlinear regression with the elastic modulus as the independent variable, where $F_b$ is the buckling force, $E_{silk}$ is the elastic modulus, h is the thickness of the probe, b is the width (400 μm) and L is the length (5.5 mm).

Brain Phantom Insertion Test.

Insertion tests were performed using the Instron crosshead and custom clamp to lower coated and uncoated probes at a speed of 4 mm/min into 0.6% agar, a close match to the mechanical properties of the brain (46). The outcome following insertion was photographed.

In Vitro Glial Scar Model Cell Culture.

Glial scarring around silk-coated microwires was assessed using a 2D model based on the protocol developed by Polikov et al. (47, 48, 54). Briefly, the cortices of embryonic day 18 rat pups were dissociated in 0.5% trypsin and plated in 24 well, poly-L-lysine coated plates at a density of 0.5 million cells/well. The cells were incubated at 37° C. in Neurobasal medium containing B27 supplement, 1% pen-strep, 1% GlutaMax (Invitrogen, Inc., Carlsbad, Calif.), and 10 ng/mL beta fibroblast growth factor (bFGF, R&D Systems, Minneapolis, Minn.). 10 days after seeding, the media was changed to include 10% FBS (Invitrogen) and 2-3 segments of steel microwire, prepared as detailed below, were allowed to sink to the bottom of each well and rest on the dissociated brain cell cultures.

Cultures with wires were fixed 17 days after seeding by incubating in 4% paraformaldehyde for 30 minutes. After washing with PBS, cells were permeablized and blocked with PBS containing 4% goat serum (Invitrogen) and 0.1% Triton-X. Primary antibodies for glial fibrillary acid protein (GFAP) (rabbit anti-GFAP, Sigma) and chondroitin sulfate (CS) (mouse anti-CS, Sigma) were diluted 1:1000 in permeablization buffer and incubated with the cells overnight at 4° C. After three PBS washes, cells were incubated with horseradish peroxidase conjugated secondary IgG antibodies specific for rabbit and mouse, respectively (Santa Cruz Biotechnology, Santa Cruz, Calif.), diluted 1:500 in permeablization buffer for 2 hours. Color was developed using a DAB substrate kit (Sigma), according to the manufacturer's instructions and incubated with cells for 1 hour.

Steel Microwire Coating.

Stainless steel microwire with a diameter of 50 μm (A-M Systems, Sequim, Wash.) was used for the scarring assay. The four treatment groups for the wire consisted of uncoated wire, silk coated wire, uncoated wire dipped in cytarabine (Ara-C) (Sigma), and silk coated wire with Ara-C. Silk coatings were achieved by dipping the microwire into ~7% w/v silk solution, allowing the silk to air dry on the wire for 15 minutes, and water annealing for 20 minutes to crystallize the silk. In one embodiment, the dipping procedure was repeated 5 times in order to build up a 5-10 micrometer thick coating of silk around the circumference of the wire. Uncoated wires were treated in the same manner, but dipped in milli-Q water instead of silk solution. For the drug-loaded wires, Ara-C was dissolved into the silk solution or milli-Q water at a concentration of 25 mg/mL prior to dipping. The microwire was cut into 3-4 mm segments prior to adding to cultures as specified above.

Glial Scar Model Analysis and Quantification.

After fixing and staining cells, images were taken along the entire length of each microwire using a 10× objective on a Zeiss Axiovert 40 CFL (Carl Zeiss AG) microscope. The images were analyzed in an automated fashion using custom ImageJ (NIH, Bethesda, Md.) and Matlab (Mathworks, Natick, Mass.) scripts based on the methods of Polikov et al. (48). Briefly, pixel intensity was averaged across the entire width of each image with the microwire registered on the horizontal. The position of the microwire was determined to be the darkest 50 μm portion of the image. The background pixel intensity was quantified by averaging the 100 μm of pixels farthest from the wire at each edge of the image, and then averaging the values for each side of the wire. The scar index for each wire was defined as the area enclosed between the edge of the microwire and the averaged pixel intensity curve at the point where the intensity reached 90% of the previously determined background value. In this way, the scar index provides a quantitative means to assess the intensity of staining proximal to the microwires.

In Vitro Screening for Cell Response to an Implantable System/Device:

Astrocytes and PC12 cells can be used to screen the implantable devices/systems described herein in vitro under a controlled environment to study responses of the cells to the implantable devices/systems described herein (e.g., electrodes). In addition, the implantable devices/systems described herein can be evaluated for their ability to record signals in vitro.

Temperature Modulated Differential Scanning Calorimetry (TMDSC):

An advanced thermal analysis method can be used to determine the glass transition, crystallization, and thermal degradation properties of silk samples.

Fourier Transform Infrared Spectroscopy (FTIR):

FTIR can be selected to analyze the silk structures prepared under different conditions. An art-recognized protein structural prediction technique, based on Fourier Self-Deconvolution (FSD) of the infrared spectra covering the Amide I region (1595~1705 cm$^{-1}$), can be used to calculate the fraction of the secondary structure.

Characterization of Mechanical Properties:

Samples can be tested for mechanical properties, including tensile testing, stress strain characterization, thermo-mechanical properties, cross-linking density, and/or the swelling ratio. Routine macro-mechanical assessments of the materials can include traditional Instron compression tests and an Instron Video Extensometer can be used and initial elastic modulus, yield stress, tensile strength, and elongation ratio can be determined.

Scanning Electron Microscopy (SEM):

SEM can be used to examine the silk-based device in variable stages of preparation and degradation to assess morphologies. The samples can be fixed for 24 h in 0.4% glutaraldehyde after fractured in liquid nitrogen using a razor blade and then dehydrated in a series of graded ethanol extractions prior to coating with gold/palladium for 3 min before SEM observation.

Statistical Analysis.

Data is presented in graphs as average±standard deviation. Average values were obtained from 3 separate replicates, unless noted otherwise. Data was analyzed for sig-

Example 2: Exemplary Coating of Flexible Neural Probes with Silk Fibroin

A layer-by-layer casting technique was used to coat a flexible electrode, e.g., a polyimide-based thin film neural probe) with silk fibroin. The probes were first centered, with electrode recording sites facing down, on PDMS molds that were fabricated using a laser cutter or soft lithography techniques. The shape of the PDMS mold can vary with the shape and/size of the electrode. The PDMS mold can partly determine the silk-coated electrode shank dimensions. Concentrated silk solution (15% w/v) was applied to the molds, e.g., by drawing a bead of solution from the tip of a pin head along the length of the probe shank. The draw speed and viscosity of the silk solution, as well as the mold shape, determined the amount of solution that adhered to the mold and probe. After drying, successive layers of silk were applied in the same manner in order to increase the thickness of the coating. Despite the manual nature of this coating technique, results were relatively consistent. For blunt tipped, 400 μm wide molds, 3 layers of silk produced a final thickness of ~70 μm on average and 6 layers resulted in twice the thickness, ~140 μm on average. In some embodiments, one single side of the electrode can be coated with this method, thus allowing recording sites to remain exposed. The silk electrode shank thickness can be controlled partly by the number of coatings. Without wishing to be bound, the layer-by-layer coating method can be performed manually or automated by a machine.

In some embodiments, silk coatings were applied to pre-fabricated thin-film electrodes via layer by layer casting. The coating is conformal and the thickness is controllable based on the concentration of the silk solution and the number of layers applied. Because the casting steps are carried out using PDMS molds, the width and shape of the coating can be adjusted using various well-defined rapid prototyping and microfabrication techniques to pattern the underlying PDMS. The coating technique described herein can be amenable to a variety of geometries. It is reported that the tip shape and surface and cross-sectional area of penetrating probes can affect the glial response (49, 50). Additionally, in contrast to dipping based coating methods, the layer-by-layer casting technique can produce a unilateral coating, allowing the recording sites on the underside of the probe (e.g., only one side of the probe shank) to remain partially or completely exposed. This can increase the recording capabilities of the probe after implantation, and reducing or eliminating concerns for the silk electrically or physically insulating the electrodes from neurons when implanted in vivo.

In some embodiments, aside from the modes of coating utilized in this Example, there can include options for post-coating treatments, wherein the mechanical features of the silk can be further modulated to impact the initial properties as well as the rate of hydration upon insertion. Exemplary post-coating treatments can include additional pre-drying steps (e.g., dry nitrogen), exposure to methanol (e.g., to maximize crystallinity) and other treatment such as electric fields and mechanical shear to induce different outcomes.

Example 3: Mechanical Properties of Silk-Coated Probes

Uncoated, 3-layer, and 6-layer silk-coated probes can be mechanically characterized by driving the probes perpendicularly onto a precision analytical balance at a rate of about 0.5 mm/min. Without wishing to be bound by theory, there can be an initial linear increase in force while the probes remain straight before buckling. As the probes continue to be driven onto the balance, the shanks can begin to buckle and bend. This can be characterized by the peak and gradual decrease in force. Eventually, the silk coating on the 3 and 6 layer probes can fracture midway down the shank, which can be characterized by a sharp decrease in force exerted on the balance.

For practical in vivo applications, neural probes are desired to remain straight during insertion in order to reach a precisely targeted region of the brain. Therefore, the buckling force should not be exceeded during insertion through the pia mater and into the cortex. The average buckling force was approximately 42 μN for the uncoated probe, ~12 mN for the 3 layer silk-coated probe, and 1~05 mN for the 6 layer coated probe. The difference in buckling forces can be at least partly resulted from the different mechanical properties of the silk coating, as well as the different dimensions of the probes imparted by the mold and layering of silk.

When approximated as rectangular beams, the buckling mechanics of the silk-coated electrodes can be modeled using Euler's fixed pin buckling equation (see Example 1). Using non-linear regression with the electrode elastic modulus as the independent variable, Euler's equation can be fit to a plot of the thickness and buckling force of the 3 and 6 coated electrodes, and determine the elastic modulus of silk ($E_{silk}$), e.g., approximately 1.5 GPa under ambient conditions, when the silk contributes the majority of the mechanical properties to the silk-coated electrodes.

In the dry state, the layered silk coatings allow the probes to sustain much greater forces before buckling, relative to the uncoated state. Without wishing to be bound by theory, the buckling force is proportional to the cube of the device thickness, thus a small change in thickness can produce a large change in the buckling force. For example, the 6-layer coated probes buckle at a force a full order of magnitude higher than the 3-layer coated probes, despite being only twice as thick. The $E_{silk}$ of ~1.5 GPa predicted by the fit of Euler's beam buckling equation to the experimental data is on the same order of magnitude as previous reports of the modulus of dry silk films (51), providing validation for the use of this model to predict the buckling force for various silk coated probe dimensions. While features such as tapered tip geometries can affect the buckling mechanics, the Euler's beam buckling model can provide a good point of reference for designing probe coatings with the necessary dimensions to penetrate the pia or dura mater.

Example 4: In Vitro Brain Phantom Insertions

Uncoated, 3 layer, and 6 layer silk coated probes were inserted into an agar gel mechanical brain phantom in order to test the efficacy of the silk coating for facilitating electrode insertion. The electrodes were clamped to the Instron crosshead in the same manner as for the buckling force test and lowered onto the gel surface at a rate of 4 mm/min. The uncoated probe was unable to penetrate the surface of the gel. The 3 layer silk-coated probe penetrated the gel surface, but bent and curled within the gel as the insertion continued. Finally, the 6 layer silk-coated probe penetrated the gel and remained straight during the entire insertion.

Previous reports have shown the elastic modulus of hydrated silk films to be on the order of 20 MPa (52), a decrease of nearly two orders of magnitude compared to the dry state, and similar to the mechanical properties demonstrated for other proposed electrode materials (12). Without wishing to be bound by theory, such hydration-mediated transition in mechanics can reduce the strain concentration at the silk-coated electrode-tissue interface, improving long-term reliability. This example also shows the mechanically dynamic nature of the probes. While the 3-layer coated probe was stiff enough to penetrate the gel initially, during the course of insertion the tip of the probe hydrated before the shaft was fully inserted, causing bending within the gel. The thicker, 6 layer coated probe took longer to hydrate and transition to a more flexible state, thus allowing it to fully penetrate into the gel while remaining straight. Based on these findings, relatively rapid insertion speeds can be desirable to allow the electrode shank to fully penetrate the brain before becoming too flexible due to hydration. Further, previous reports have shown that faster insertion speeds may cause less acute damage to the brain (53).

Example 5: Assessing Silk-Mediated Gliosis with an In Vitro Model

Figure 1B:
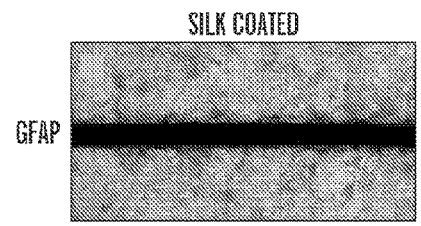
Figure 1C:
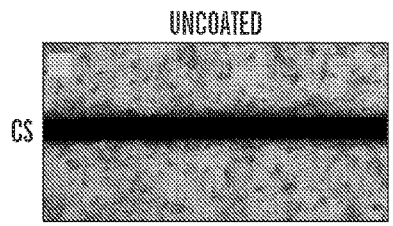
Figure 1D:
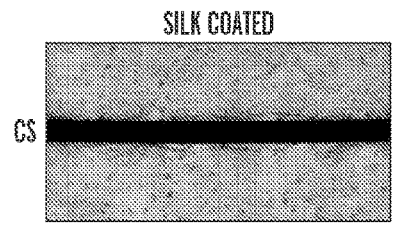

The effect of silk fibroin coatings on reactive gliosis was tested in an in vitro model of glial scarring around an electrode mimic. Uncoated and silk-coated segments of 50 µm stainless steel microwire electrodes were dropped into mixed cultures of dissociated embryonic rat cortical cells. Serum and bFGF were added to the culture to initiate the scarring response around the microwires and after one week the cultures were fixed and stained for glial fibrillary acid protein (GFAP) (FIGS. 1A and 1B) and chondroitin sulfate (CS) (FIGS. 1C and 1D).

Figures 2A, 2B:
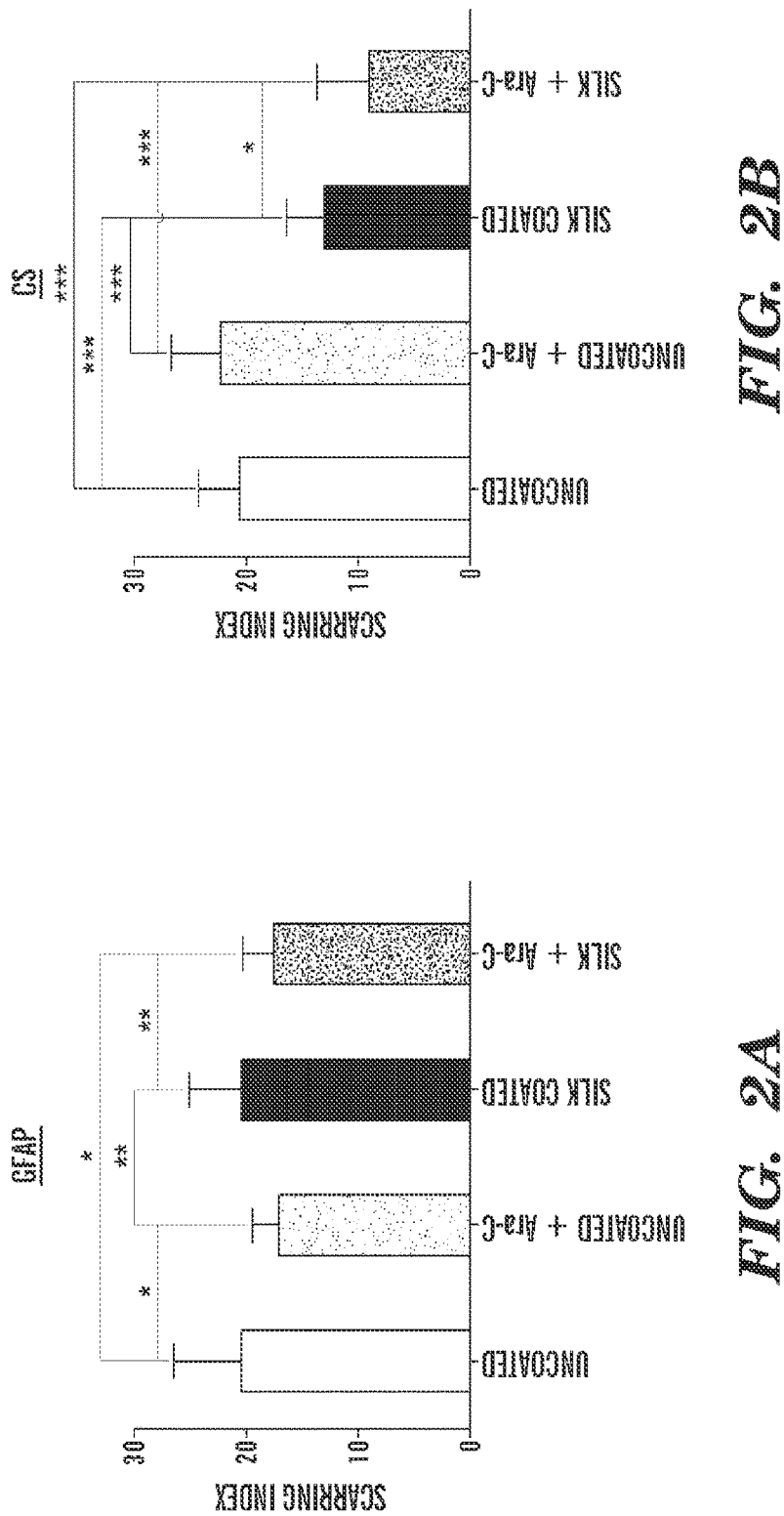
FIGS. 2A and 2B show average scar index values for in vitro glial scar cultures stained for GFAP and CS, respectively. * $p<0.05$,  $p<0.005$, * $p<0.0005$.
Figure 3:
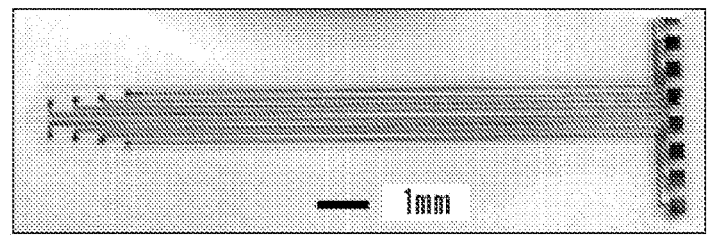
FIG. 3 is an image showing an exemplary flexible electrode fabricated by encapsulating gold traces in parylene C. Additional details of the flexible electrode can be found in Metallo C. et al., "Flexible parylene-based microelectrode arrays for high resolution EMG recordings in freely-moving small animals." J Neurosci Methods. (2011) 15; 195(2):176-84.

The scarring around the uncoated and coated wires was quantified based on staining intensity proximal to the wires (FIGS. 2A and 2B). For GFAP, no difference in scar formation was observed between the uncoated and silk-coated wires (FIG. 2A). However, the silk-coated wires stimulated significantly less CS accumulation during scar formation relative to the uncoated wires (FIG. 2B).

In addition to the dynamic mechanical properties, the cellular response to silk coatings in the in vitro model of glial scarring further supports its use in penetrating electrodes. Silk coatings resulted in the same average amount of GFAP expression, a common marker for gliosis and astrocyte reactivity, relative to the uncoated inert stainless steel microwires. This indicates that astrocyte proliferation and activation was similar for both materials. However, silk coatings stimulated significantly less CS accumulation around the microwire. This surprising finding indicates that secretion of ECM molecules (e.g., inhibitory ECM molecules such as CS) can be independent of astrocyte reactivity and can be mediated by the material chemistry of the electrode implant. CS can inhibit axon growth and regeneration; therefore, lower levels of this molecule can be beneficial for promoting neuronal proximity to electrode implants, improving long-term performance.

In addition, in some embodiments, nerve impulses can be measured by using a silk-coated cortical electrode (e.g., for nerve recording) in a brain slice, and the scarring response can be determined as described above. A comparison of the silk-coated cortical electrode with existing cortical electrodes (e.g., without silk coating) can be conducted to determine the performance and efficacy.

Example 6: Capacity for Silk to Release Gliosis Modulating Drugs In Vitro

Figure 1E:
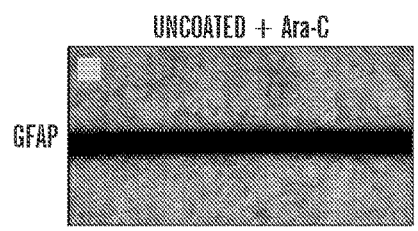
Figure 1F:
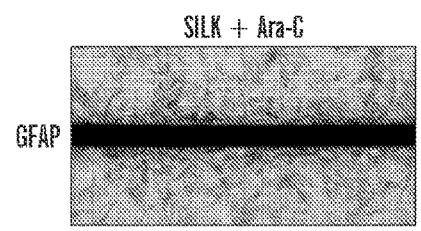
Figure 1G:
Figure 1H:
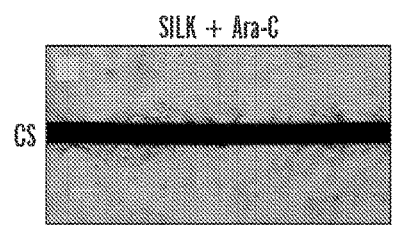

While silk coatings alone can reduce some gliosis responses compared to stainless steel, the ability to encapsulate and release scar-inhibiting compounds can provide an additional avenue for improving the chronic reliability of silk-based penetrating electrodes. Accordingly, the scarring assay as shown in Example 5 was also carried out with the addition of the anti-mitotic drug cytarabine (Ara-C) in the silk coating. The drug was incorporated into the silk-coated microwires by dissolving it in the aqueous silk solution before dipping. Uncoated control wires were dipped in water loaded with the drug at the same concentration as in the silk solution. The silk-coated, Ara-C loaded wires produced a significantly different scarring response both in GFAP (FIG. 1F) and CS (FIG. 1H) expression relative to both silk alone and the uncoated wire (FIGS. 1E and 1G).

CS quantification shows that Ara-C loaded silk coatings resulted in a significantly lower scarring response relative to any other treatment group, including silk alone and the Ara-C water dipped steel wires (FIG. 2B).

The biocompatibility of chronic brain penetrating electrodes is integral to the long-term reliability and functionality of the device. The mechanical properties, innate immunogenicity, and/or chemical functionalization, of the materials used to fabricate the probe shanks can affect the tissue response in vivo.

As presented herein, silk possesses a unique combination of material properties which make it suitable for use in a penetrating electrode system. The mechanical and low inflammatory properties of silk, as well as its capacity to encapsulate and release gliosis-modifying compounds, make it an attractive biomaterial for the next generation of chronic, indwelling neural probes. Such probes can have improved biocompatibility, for reduced glial scar encapsulation and ultimately better long-term reliability. The silk coating can have applications beyond penetrating electrodes, e.g., the use of silk fibroin for many other CNS applications, such as in shunts and spinal cord nerve guides, where gliosis is desirable to be controlled at the tissue-implant interface to achieve optimal outcomes.

Further, provided herein is a novel dynamic biomaterial system for neural implant devices as a route to overcome loss of function at the biological abiotic interface. Electrogelation of a silk solution can be used to generate conformal contact with nerves, to remodel the interface on demand, and to maintain electrical contact between the biomaterial and the biological tissue to optimize function over time.

Example 7: In Vivo Evaluation of an Implantable Device Described Herein

In some embodiments, nerve impulses can be measured in a brain tissue of an animal model, e.g., a rat, by inserting a silk-coated cortical electrode (e.g., for nerve recording) in its brain, and the scarring response can be determined as described above, e.g., by histology after sacrifice. A comparison of the silk-coated cortical electrode with existing cortical electrodes (e.g., without silk coating) can be conducted to determine the performance and efficacy.

Figure 4:
FIG. 4 is an image showing exemplary electrical components such as wires partially coated with silk fibroin.
Figure 5A:
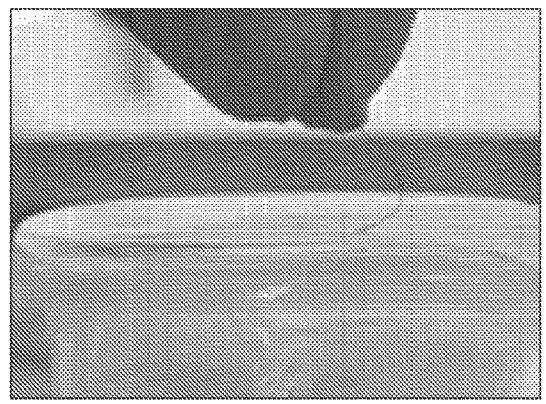
FIGS. 5A-5C shows penetration capability of uncoated and silk-coated wires through a Parafilm membrane.
Figure 5B:
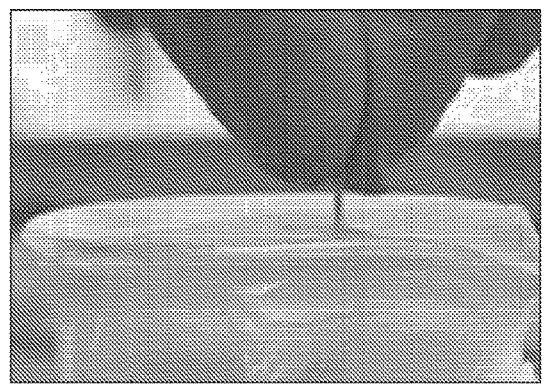
Figure 5C:

Example 8: Use of Silk Coating to Strengthen a Flexible Wire with a Transition from Stiff to Compliant Upon Hydration Flexible enameled copper wires (~100 µm diameter) were dip-coated in hexafluoroisopropanol (HFIP) containing ~15% w/v silk fibroin. Upon evaporation of the HFIP solvent, the wires were encapsulated in a stiff silk coating (see FIG. 4). In order to demonstrate the dynamic mechanical properties of the coating, a beaker was filled with water and covered with Parafilm to simulate a tissue membrane (such as the dura in the brain). FIG. 5A shows an uncoated wire incapable of penetrating the Parafilm. FIG. 5B shows that the silk-coated wire could easily penetrate the Parafilm membrane. The silk-coated wire after penetration was then left to hydrate in the aqueous environment for approximately 30 seconds. As shown in FIG. 5C, when the coated wire was removed from the water, the coated wire had transitioned to a flexible state and thus could not penetrate the Parafilm membrane, as it was in a dry state before.

Example 9: Assessment of Various Coating Techniques to Generate Silk Coatings on Flexible Planar Substrates Numerous techniques were assessed to determine suitable or optimum approach for coating flexible implants. Strips of parylene C (approximately 2 mm×8 mm×60 µm), an inert material commonly used in medical devices and in the fabrication of thin, flexible electrodes, was used as a model test substrate. Coating methods generally is divided into two categories: (i) dip coating, and (ii) casting. The dip coating approaches involved briefly immersing the parylene strips in various forms of silk solution, followed by air-drying (see FIG. 6A). The solutions utilized for dip coating included (i) aqueous silk solution, (ii) high silk concentration HFIP solution, and (iii) heat-liquefied silk electro-gel (e-gel) solution.

Alternatively, casting methods involved submerging the parylene strips in a volume of aqueous or gel based silk solution spread on a polystyrene plate and allowing the silk to air dry to form films (see FIGS. 6B-6C). The coated parylene was then manually cut out of the encapsulating film using a razor blade or scissors. For more precise release of the coated parylene from the silk film, a computer controlled laser cutter could be employed.

In particular embodiments, the casting method can involve a two-step layering process. First, a volume of heat-liquefied silk e-gel was poured into a plate and allowed to re-gel by cooling (3-5 minutes). The parylene strips to be encapsulated were then placed on top of the first e-gel layer and covered by another volume of heat-liquefied e-gel. The layered gel was then left to air dry. This process ensured even layers of silk on both sides of the parylene strips, preventing delamination of the silk from the substrate upon drying. The coating formed uniform layers on the parylene, the thickness of which could be individually controlled by adjusting the volume or concentration of the silk solution applied in each layer (see FIGS. 7A-7B and 8). Furthermore, the viscosity of the liquefied e-gel solution allowed for selective and localized application of the top layer. This enabled portions of the implantable device to be left uncoated as desired. For instance, as shown in FIG. 9, only one side of the contact pads on an electrode was coated with silk. In the future, cytokines could be incorporated into the aqueous silk, which would become entrapped upon drying and released after implantation.

Example 10: Buckling Force Characterization of Dynamic Silk Coatings

The mechanical properties of the uncoated and silk-coated implant models (e.g., parylene implants) were quantified by measuring the buckling force (the maximum force exerted by an implant, e.g., parylene strips, when pinned and loaded in a vertical orientation). This characterization was chosen to mimic the type of loading experienced by column-like implants, such as electrodes, when used to penetrate tissues. A custom clamping mechanism was fabricated to fix a 5 mm length of the parylene strips to the crosshead of an Instron 3366 mechanical testing frame. Samples were lowered at a rate of 0.5 mm/min onto a steel plate. All measurements were performed in air at room temperature. Force measurements were collected with an Instron 10 N load-cell and the accompanying Bluehill Software package. When measured with low loads, e.g., for uncoated samples, force measurements of the uncoated samples were alternatively collected using a Mettler-Toledo MS2045/03 analytical balance and custom software. The values collected with this custom test configuration were shown in FIG. 10A after validating that they matched closely with the averaged values of the load-cell data.

Figure 10A:
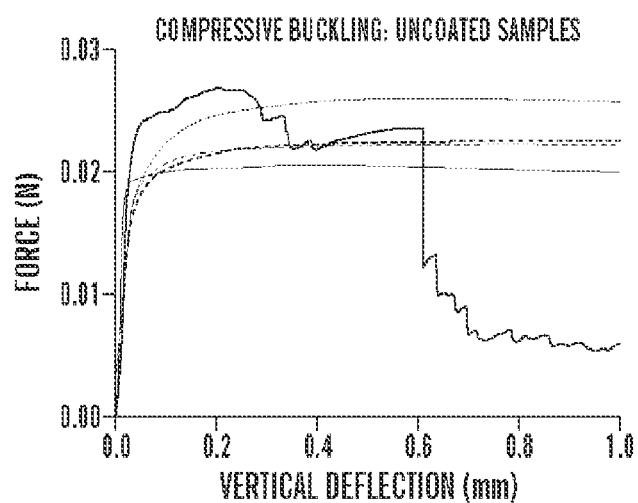
FIGS. 10A-10C show force curves for five replicates of uncoated parylene (FIG. 10A), silk-coated parylene (FIG. 10B) and silk-coated parylene allowed to hydrate for 30 minutes in 37° C. PBS (FIG. 10C).
Figure 10B:
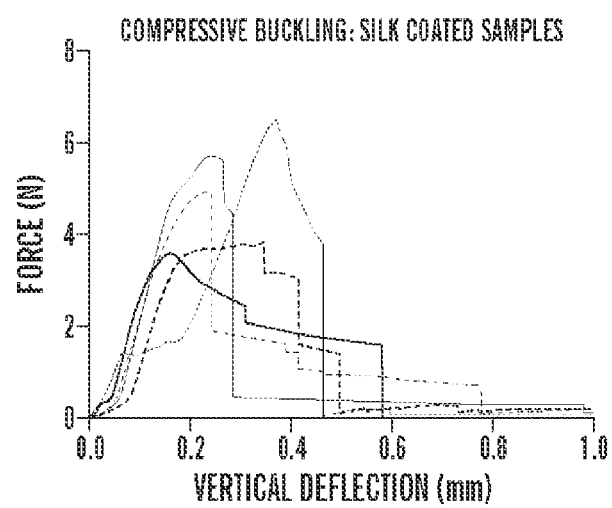
Figure 10C:
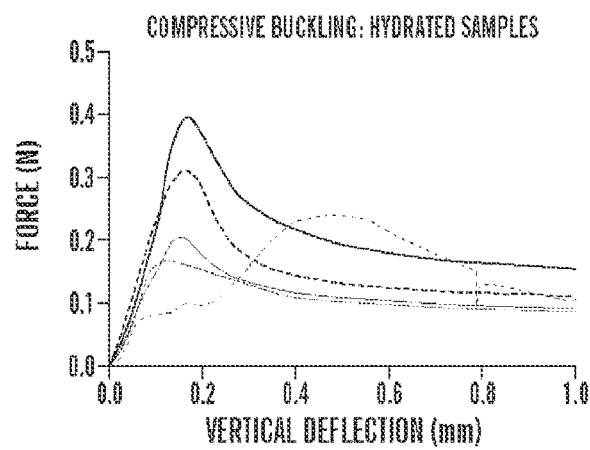

Five samples from each of the three different treated implant groups were evaluated (see FIGS. 10A-10C). The first group consisted of uncoated parylene strips (approximately 2 mm×5 mm×60 µm) (FIG. 10A). The highly elastic strips quickly buckled at loads on the order of two-hundredths of a Newton. Parylene strips coated in silk (approximately 2.7 mm×5 mm×200 µm) were then evaluated in the dry state, and observed to buckle under loads on the order of 5 Newtons (FIG. 10B). Silk-coated samples were also evaluated after being allowed to hydrate for 30 minutes in 0.1M PBS at 37° C. (FIG. 10C). The samples were immediately mounted and tested after removal from the PBS, and buckled at forces on the order of 2-tenths of a Newton.

Figure 11:
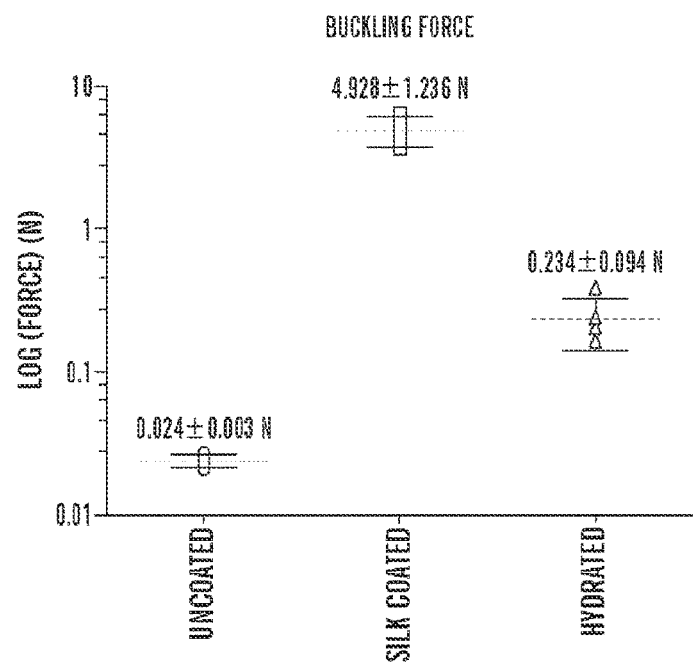
FIG. 11 show average buckling forces (in log scale) for different treated parylene (uncoated parylene, silk-coated parylene, and silk-coated parylene after hydration).

Average buckling forces for the three groups are shown on a logarithmic plot (FIG. 11). The dry silk-coated model implants withstood forces over two orders of magnitude larger than the uncoated samples before they buckled. In an aqueous environment, the silk coating hydrated in a matter of minutes. This resulted in more than an order of magnitude smaller buckling force compared to the dry silk-coated samples. After hydration for 30 minutes, the silk-coated samples have mechanical properties more similar to the uncoated samples, than to the coated samples in the dry state. Without wishing to be bound by theory, in some embodiments, because silk is fully biodegradable, longer periods in an aqueous environment can result in the properties of the coated samples becoming similar to those of the uncoated samples as the silk continues to hydrate, and eventually degrades.

Example 11: Design of Implantable Silk Shanks and Silk-Coated Electrodes

Figure 13A:
FIGS. 13A-13D are images of implantable silk shanks and silk-coated electrodes.
Figure 13B:
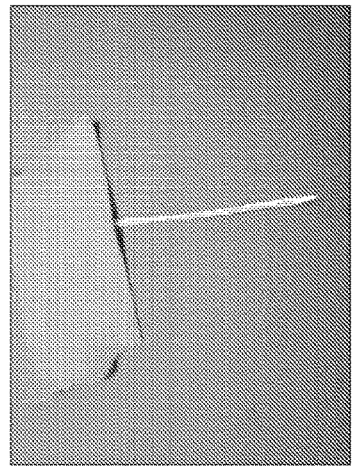

Silk shanks can be produced by any methods known in the art. For example, a molding/freezing processing approach can be used to make robust silk constructs. The molding/freezing approach involved the utilization of an aqueous silk solution made from cocoons from a Taiwanese supplier. The silk solution was concentrated to about 25% w/v fibroin (balance is water). Small-diameter, flexible Tygon tubing was used as a mold; silk solution was injected using a plastic syringe and both ends sealed using the high heat of a soldering iron. The silk-containing tubing was stored in an EdgeStar Model FP430 thermoelectric cooler for a period of at least 1 week at −5° C. Upon removal from the freezer, the molded material was released from the tube, e.g., by flushing the inner diameter with milli-Q water ejected from a syringe. At the cooler temperature (−5° C.), the final sample morphology can be determined by the length of time in the cooler. For example, after about 1.5 weeks in the cooler, the silk immediately after removal can be white, stretchable, e.g., with the general consistency of boiled spaghetti. After storing at room temperature, trapped water evaporates and the resulting material can become non-porous and fairly stiff. Varying diameters were achieved based on appropriate tubing selection (FIG. 13A). A sharp tip could be produced, e.g. by any known methods in the art, such as sharpening with a razor blade (FIG. 13B).

Figure 13C:
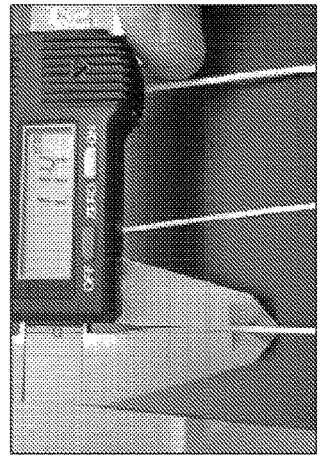
Figure 13D:
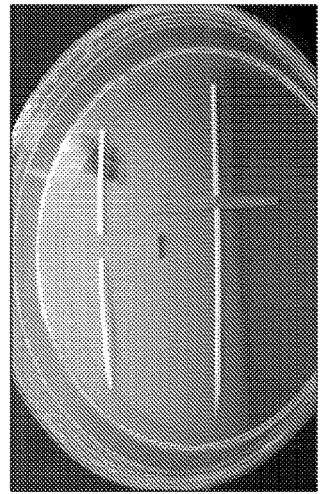
Figures 15A, 15B:
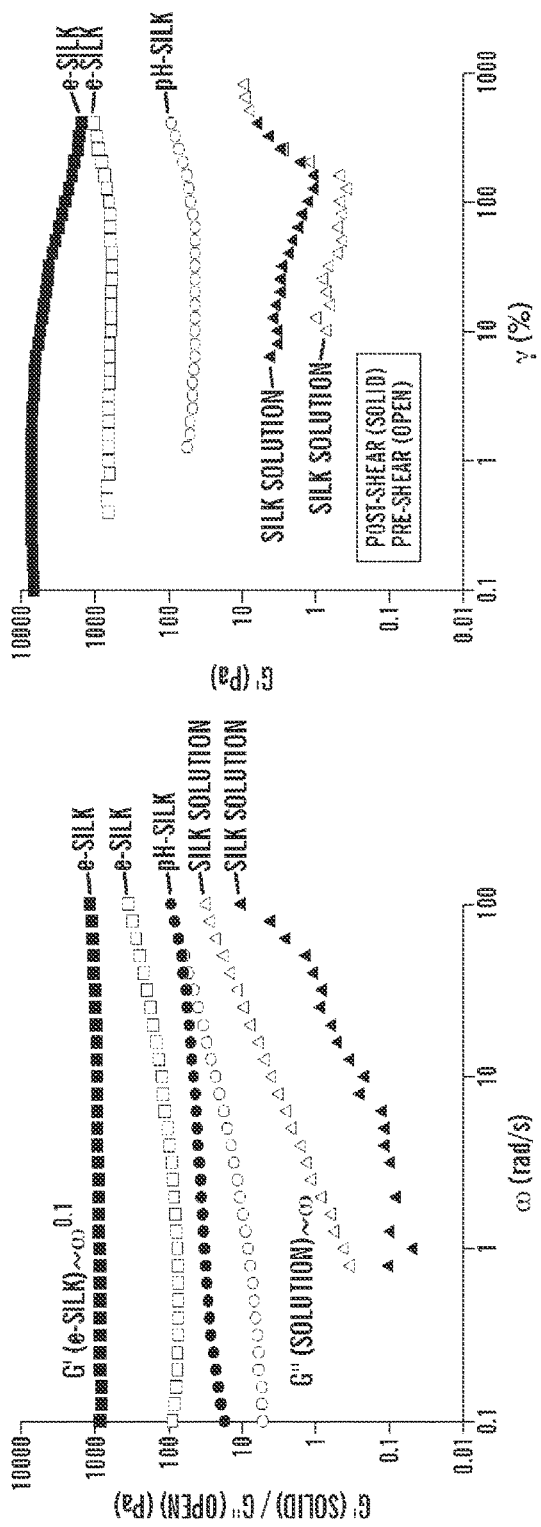
FIGS. 15A-15D show mechanical characteristics data for electrogelation of silk solutions as determined by dynamic oscillatory shear rheology.
Figure 15D:
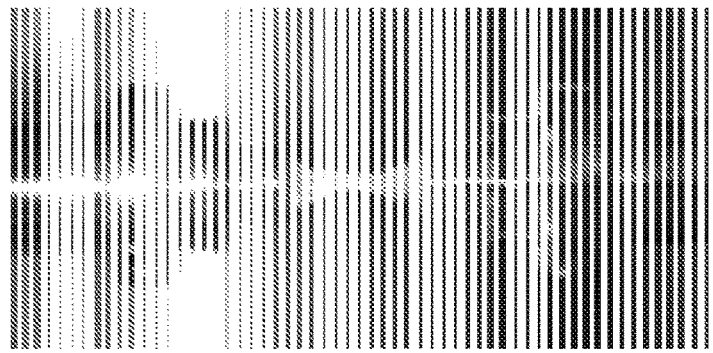
Figure 15C:
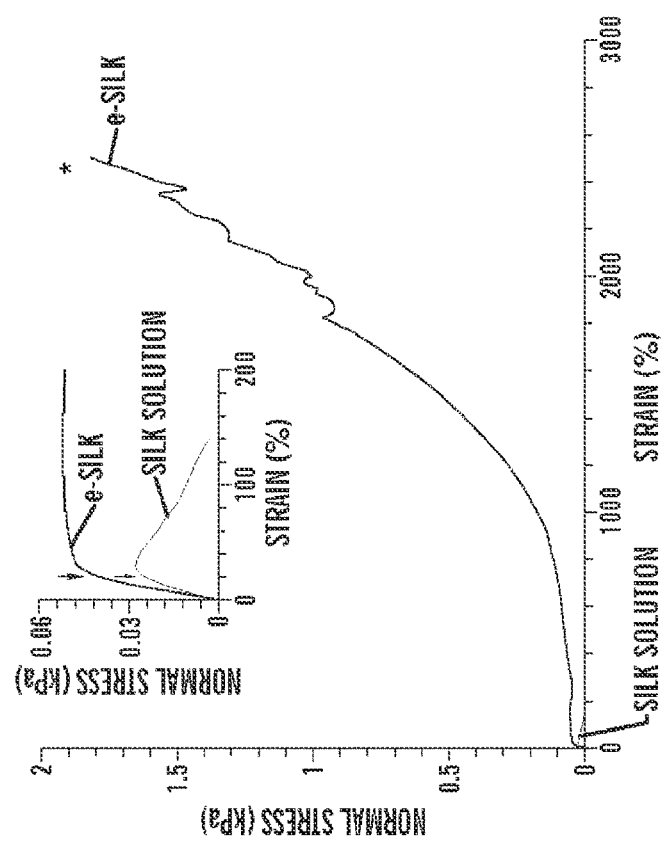

A different silk morphology could be achieved by leaving the silk-containing tubing in the cooler at −5° C. for over 2 weeks (FIGS. 13C-13D). Immediately after removal from the cooler, the silk was flushed from the tubing and appeared to have a foam-like morphology. It is known that the freezer temperature of water in silk solution is close to −8.5° C. Without wishing to be bound by theory, the −5° C. temperature allows the water to start freezing, but allows the silk fibroin to maintain some mobility. Freeze-concentration occurs, in which the low surface-tension silk fibroin coagulates into specific regions of high concentration and is stretched as freezing water begins to expand. The stretching and alignment of silk fibroin molecular chains leads to bonding and the formation of a porous silk network, from which the water is ultimately removed. As FIG. 13C shows, the silk foam construct can be molded with a conducting wire inside the tubing (top construct shows small-diameter motor wire protruding from the left end of the sample). Thus, a tubular structure can be formed after removal of the conducting wire. Given this foam is fairly stiff when dry, a razor blade could be used to form a sharp tip (bottom construct in FIG. 13C). As with the silk constructs described earlier, the diameter can be adjusted through appropriate tubing selection (FIG. 13D).

To evaluate the ability of the sharpened silk constructs to penetrate material, in one embodiment, Parafilm (a polymeric material used in laboratories to cover and seal bottles and Petri dishes) was stretched across the open top of a plastic Petri dish. The sharpened nonporous silk construct (without a wire embedded) or foam-like silk construct penetrated the Parafilm membrane. No visible damage to the silk was evident. However, all of the nonporous and foam-like silk constructs become softer when hydrated. Given its porous nature, the foam-like constructs became much softer than the nonporous constructs when hydrated. When dried again, all constructs regained the stiffness as originally in a dry state.

Example 12: Electrogelation of a Silk Solution

When aqueous solutions of silkworm silk were exposed to DC currents, under certain electric fields, the solution begins to gel on the positive electrode (FIGS. 14A-14B). While electrospinning of polymers, including silks, is generally performed at voltage potentials as high as >30 kV, the utilization of low DC voltages to generate a controlled volume of silk gel was unexpected and novel. For an illustrative purpose only, electrodes are immersed in an aqueous solution of silk protein and 25 VDC is applied over a 3 minute period to a pair of leads. Electrolysis occurs during electrogelation. Within seconds of the application of the voltage, a visible gel forms at the positive electrode and emanates outward.

When silk electrogelation (e-gel) is executed in a voltage-controlled manner, the current draw in the process follows a repeated trend; initially high current draw drops exponentially to a minimal level. The actual current values depend on many factors, including applied voltage level, electrode area and spacing, and conductivity of the silk solution. Silk gel formed through electrogelation has a highly viscous (soft) consistency and is very tacky, bearing a resemblance to thick mucus. Remarkably, after the electric field was turned off, the adhesive gel state was retained. Thus, the structural state of the protein formed under e-gel conditions was sufficiently stable to retain material functions in the absence of the applied electric field. Yet, the gel formed can be returned to the solution state through a reverse electrical process. If the electrode polarity is reversed and 25 VDC is re-applied, the gel disappears, while fresh gel is formed on the newly created positive electrode. Electrogelation and reversal back to silk solution can be cycled many times.

The changes in mechanical characteristics due to electrogelation of silk solutions were evaluated by dynamic oscillatory shear rheology (FIGS. 15A-15D). For silk solutions, liquid-like, viscous behavior measured by the loss modulus (G") dominated the mechanical response within the probed frequency range ω with G"~ω. On the other hand, the mechanical response of e-gels resembled that of a soft-solid-like, physical gel. There was a significant increase in the elastic response, measured by the storage modulus (G'). The frequency dependence of G' was weak but finite (G'~ω$^{0.1}$) while the apparent minimum in G" indicated a possible G', G" cross-over at even lower frequencies due to eventual relaxation of temporary, physical crosslinks.

To investigate the significance of increased proton concentration in the mechanism of e-gel formation at the positive electrode, the solution was titrated to control the pH, termed "pH-gels". After titration of the silk solution, pH-gels displayed viscoelastic behavior where G'>G" for the measured frequencies, albeit a clear frequency dependence of G', indicating relatively long inter-chain crosslink relaxation times approaching those in the e-gel.

Silk solutions displayed non-linear shear thinning at lower strain amplitudes followed by shear thickening with increasing shear. The pH-gels and e-gels showed a large linear viscoelastic regime and a subsequent non-linear regime similar to that observed for silk solutions, including a slight but reproducible strain-stiffening at high shear. Within the measurable strain amplitudes there were no apparent yielding for either pH-gels or e-gels.

The strain hardening was reversible over several cycles. However, when a high amplitude shear was applied over several minutes, an irreversible transition into a stiffer but more brittle gel was observed with apparent yielding. High amplitude shear also led to a slight increase in the G' values measured from silk solutions in the linear regime.

The adhesion of silk solution and e-gel on different surfaces was characterized using a Dynamic Mechanical Analyzer (DMA) via strain-controlled, transient tensile testing. Both silk solution and e-gel displayed linear stress-strain behavior for strains up to 20% on stainless steel surfaces. At higher strains, the sample/DMA plate interface area progressively decreased, which led to significantly different non-linear stress-strain behavior for the silk solution and the e-gel. For the silk solution, the normal stress peaked at ca. 30 Pa at 20% strain and gradually dropped to zero (ca. 150% strain) due to complete de-adhesion from the plate. On the other hand, e-gel displayed unique adhesion characteristics when compared to other bioadhesive systems. After the initial linear regime, the stress progressively increased, while the stress-strain curve showed sporadic fluctuations presumably due to an interplay between decreasing e-gel/plate interface area due to partial de-adhesion and apparent stiffening of e-gel due to dehydration and elongational forces. Strains up to 2,500% were recorded until failure upon complete de-adhesion. The work of adhesion on stainless steel calculated from the area under the force-displacement curve for fully hydrated e-gels was 1.09±0.26 mJ (mean±std. dev., n=3). Similar work of adhesion values (1-1.5 mJ) were measured on other surfaces such as acrylic and wood surfaces, highlighting the versatility of e-gel adhesion.

Example 13: Use of Silk Films for Electrophysiological Studies and Ion Channel Targeted Drug Delivery to Brain Astroglial Cells Astroglial cell survival and ion channel function are exemplary molecular targets in terms of neural cell interactions with biomaterials and/or electronic interfaces. Reactive astrogliosis is the most typical in vivo response that occurs after brain implants and needs to be controlled in biomaterial engineering. This cellular phenomena is generally characterized by activation of the proliferative state and alteration of expression patterns of astroglial potassium (K+) channels.

Silk interactions with cultured neocortical astroglial cells were assessed. Cell viability revealed that cell survival was comparable for astrocytes plated on silk-coated glass coverslips compared to those plated on poly-D-lysine (PDL), a well-known polyionic substrate, used to promote astroglial cell adhesion to glass surfaces. Comparative analyses of whole-cell single-cell patch-clamp experiments indicated that silk and PDL-coated cells displayed depolarized resting membrane potentials (~−40 mV), very high input resistance and low specific conductance, with values similar to those of undifferentiated glial cells as previously reported. Analyses of K+ conductance indicated that silk-astrocytes expressed large outwardly delayed rectifying K+ current (KDR).

It was next sought to determine whether silk embedded with guanosine (GUO) enabled the direct modulation of astroglial K+ conductance in vitro. The results indicated that astrocytes plated on GUO-embedded silk were more hyperpolarized and expressed inward rectifying K+ conductance (Kir). Collectively the results indicate that silk is a suitable biomaterial as a platform for studies of astroglial ion channel responses and related physiology.

REFERENCES

1. Andersen R A, Hwang E J, Mulliken G H. Cognitive Neural Prosthetics. Annu Rev Psychol. 2010; 61:169-C3.
2. Venkatraman S, Elkabany K, Long J D, Yimin Yao, Carmena J M. A System for Neural Recording and Closed-Loop Intracortical Microstimulation in Awake Rodents. IEEE Transactions on Biomedical Engineering. 2009 January; 56(1):15-22.
3. Fayad G, Elmiyeh B. Cochlear Implant [Internet]. In: Hakim N S, editor. Artificial Organs. London: Springer London; 2009 [cited 2011 Dec. 11]. p. 133-6. Available from: http://www.springerlink.com.ezproxy.library.tufts-.edu/content/n318236921756523/
4. Subbaroyan J, Martin D C, Kipke D R. A finite-element model of the mechanical effects of implantable microelectrodes in the cerebral cortex. Journal of Neural Engineering. 2005 Dec. 1; 2(4):103-13.
5. Lee H, Bellamkonda R V, Sun W, Levenston M E. Biomechanical analysis of silicon microelectrode-induced strain in the brain. Journal of Neural Engineering. 2005 Dec. 1; 2(4):81-9.
6. Cullen D K, Simon C M, LaPlaca M C. Strain rate-dependent induction of reactive astrogliosis and cell death in three-dimensional neuronalastrocytic co-cultures. Brain Research. 2007 Jul. 16; 1158(0):103-15.
7. Thelin J, Jorntell H, Psouni E, Garwicz M, Schouenborg J, Danielsen N, et al. Implant Size and Fixation Mode Strongly Influence Tissue Reactions in the CNS. PLoS ONE. 2011 Jan. 26; 6(1):e16267.
8. Biran R, Martin D C, Tresco P A. The brain tissue response to implanted silicon microelectrode arrays is increased when the device is tethered to the skull. J Biomed Mater Res A. 2007 July; 82(1):169-78.
9. Harris J P, Capadona J R, Miller R H, Healy B C, Shanmuganathan K, Rowan S J, et al. Mechanically adaptive intracortical implants improve the proximity of neuronal cell bodies. Journal of Neural Engineering. 2011 Oct. 1; 8:066011.
10. Rousche P J, Pellinen D S, Pivin D P, Williams J C, Vetter R J, Kipke D R. Flexible polyimide-based intracortical electrode arrays with bioactive capability. Biomedical Engineering, IEEE Transactions on. 2001; 48(3): 361-71.
11. Mercanzini A, Cheung K, Buhl D L, Boers M, Maillard A, Colin P, et al. Demonstration of cortical recording using novel flexible polymer neural probes. Sensors and Actuators A: Physical. 2008 May 2; 143(1):90-6.
12. Hess A E, Capadona J R, Shanmuganathan K, Hsu L, Rowan S J, Weder C, et al. Development of a stimuli-responsive polymer nanocomposite toward biologically optimized, MEMS-based neural probes. J. Micromech. Microeng. 2011 May; 21(5):054009.
13. Kato Y, Saito I, Hoshino T, Suzuki T, Mabuchi K. Preliminary Study of Multichannel Flexible Neural Probes Coated with Hybrid Biodegradable Polymer. In: Engineering in Medicine and Biology Society, 2006. EMBS '06. 28th Annual International Conference of the IEEE. 2006. p. 660-3.
14. Takeuchi S, Ziegler D, Yoshida Y, Mabuchi K, Suzuki T. Parylene flexible neural probes integrated with microfluidic channels. Lab Chip. 2005 May; 5(5):519-23.
15. Suzuki T, Mabuchi K, Takeuchi S. A 3D flexible parylene probe array for multichannel neural recording. In: Neural Engineering, 2003. Conference Proceedings. First International IEEE EMBS Conference on. 2003. p. 154-6.
16. Wester B A, Lee R H, LaPlaca M C. Development and characterization of in vivo flexible electrodes compatible with large tissue displacements. J. Neural Eng. 2009 April; 6(2):024002.
17. Seymour J P, Kipke D R. Neural probe design for reduced tissue encapsulation in CNS. Biomaterials. 2007 September; 28(25):3594-607.
18. Chorover S L, Deluca A-M. A sweet new multiple electrode for chronic single unit recording in moving animals. Physiology & Behavior. 1972 October; 9(4):671-4.
19. Lind G, Linsmeier C E, Thelin J, Schouenborg J. Gelatine-embedded electrodes—a novel biocompatible vehicle allowing implantation of highly flexible microelectrodes. J Neural Eng. 2010 August; 7(4):046005.
20. Stice P, Gilletti A, Panitch A, Muthuswamy J. Thin microelectrodes reduce GFAP expression in the implant site in rodent somatosensory cortex. Journal of Neural Engineering. 2007 Jun. 1; 4(2):42-53.
21. Lewitus D, Smith K L, Shain W, Kohn J. Ultrafast resorbing polymers for use as carriers for cortical neural probes. Acta Biomaterialia. 2011 June; 7(6):2483-91.
22. Harris J P, Hess A E, Rowan S J, Weder C, Zorman C A, Tyler D J, et al. In vivo deployment of mechanically adaptive nanocomposites for intracortical microelectrodes. J. Neural Eng. 2011 August; 8(4):046010.
23. Zhong Y, McConnell G C, Ross J D, DeWeerth S P, Bellamkonda R V. A Novel Dexamethasone-releasing, Anti-inflammatory Coating for Neural Implants. In: 2nd International IEEE EMBS Conference on Neural Engineering, 2005. Conference Proceedings. IEEE; 2005. p. 522-5.
24. Zhong Y, Bellamkonda R V. Dexamethasone-coated neural probes elicit attenuated inflammatory response and neuronal loss compared to uncoated neural probes. Brain Research. 2007 May 7; 1148(0):15-27.
25. Kim D-H, Martin D C. Sustained release of dexamethasone from hydrophilic matrices using PLGA nanoparticles for neural drug delivery. Biomaterials. 2006 May; 27(15):3031-7.
26. Mercanzini A, Reddy S, Velluto D, Colin P, Maillard A, Bensadoun J-C, et al. Controlled Release Drug Coatings on Flexible Neural Probes. In: 29th Annual International Conference of the IEEE Engineering in Medicine and Biology Society, 2007. EMBS 2007. IEEE; 2007. p. 6612-5.
27. Zhong Y, Bellamkonda R V. Controlled release of anti-inflammatory agent α-MSH from neural implants. Journal of Controlled Release. 2005 Sep. 2; 106(3):309-18.
28. Purcell E K, Thompson D E, Ludwig K A, Kipke D R. Flavopiridol reduces the impedance of neural prostheses in vivo without affecting recording quality. Journal of Neuroscience Methods. 2009 Oct. 15; 183(2):149-57.
29. Azemi E, Lagenaur C F, Cui X T. The surface immobilization of the neural adhesion molecule L1 on neural probes and its effect on neuronal density and gliosis at the probe/tissue interface. Biomaterials. 2011 January; 32(3): 681-92.
30. David S, Lacroix S. Molecular Approaches to Spinal Cord Repair. Annual Review of Neuroscience. 2003 March; 26(1):411-40.
31. Altman G H, Diaz F, Jakuba C, Calabro T, Horan R L, Chen J, et al. Silk-based biomaterials. Biomaterials. 2003 February; 24(3):401-16.
32. Meinel L, Hofmann S, Karageorgiou V, Kirker-Head C, McCool J, Gronowicz G, et al. The inflammatory responses to silk films in vitro and in vivo. Biomaterials. 2005 January; 26(2):147-55.
33. Hu X, Shmelev K, Sun L, Gil E-S, Park S-H, Cebe P, et al. Regulation of Silk Material Structure by Temperature-Controlled Water Vapor Annealing. Biomacromolecules. 2011; 12(5):1686-96.
34. Rockwood D N, Preda R C, Yucel T, Wang X, Lovett M L, Kaplan D L. Materials fabrication from *Bombyx mori* silk fibroin. Nat. Protocols. 2011; 6(10):1612-31.
35. Lin Y-C, Ramadan M, Hronik-Tupaj M, Kaplan D L, Philips B J, Sivak W, et al. Spatially Controlled Delivery of Neurotrophic Factors in Silk Fibroin-Based Nerve Conduits for Peripheral Nerve Repair. Annals of Plastic Surgery. 2011 August; 67(2):147-55.
36. Huang W, Begum R, Barber T, Ibba V, Tee N C H, Hussain M, et al. Regenerative potential of silk conduits in repair of peripheral nerve injury in adult rats. Biomaterials. 2012 January; 33(1):59-71.
37. Feng Zhang, Rong Liu, Zuo B Q, Qin J Z. Electrospun Silk Fibroin Nanofiber Tubes for Peripheral Nerve Regeneration. In: 2010 4th International Conference on Bioinformatics and Biomedical Engineering (iCBBE). IEEE; 2010. p. 1-4.
38. Yang Y, Yuan X, Ding F, Yao D, Gu Y, Liu J, et al. Repair of Rat Sciatic Nerve Gap by a Silk Fibroin-Based Scaffold Added with Bone Marrow Mesenchymal Stem Cells. Tissue Engineering Part A. 2011 September; 17(17-18): 2231-44.
39. Madduri S, Papaloïzos M, Gander B. Trophically and topographically functionalized silk fibroin nerve conduits for guided peripheral nerve regeneration. Biomaterials. 2010 March; 31(8):2323-34.
40. Ghaznavi A M, Kokai L E, Lovett M L, Kaplan D L, Marra K G. Silk Fibroin Conduits. Annals of Plastic Surgery. 2011 March; 66(3):273-9.
41. Benfenati V, Toffanin S, Capelli R, Camassa L M A, Ferroni S, Kaplan D L, et al. A silk platform that enables electrophysiology and targeted drug delivery in brain astroglial cells. Biomaterials. 2010 November; 31(31): 7883-91.
42. Wittmer C R, Claudepierre T, Reber M, Wiedemann P, Garlick J A, Kaplan D, et al. Multifunctionalized Electrospun Silk Fibers Promote Axon Regeneration in the Central Nervous System. Advanced Functional Materials. 2011 Nov. 22; 21(22):4232-42.
43. Szybala C, Pritchard E M, Lusardi T A, Li T, Wilz A, Kaplan D L, et al. Antiepileptic effects of silk-polymer based adenosine release in kindled rats. Experimental Neurology. 2009 September; 219(1):126-35.
44. Kim D-H, Viventi J, Amsden J J, Xiao J, Vigeland L, Kim Y-S, et al. Dissolvable films of silk fibroin for ultrathin conformal bio-integrated electronics. Nat Mater. 2010 June; 9(6):511-7.
45. Xia Y, Whitesides G M. Soft Lithography. Angewandte Chemie International Edition. 1998 Mar. 16; 37(5):550-75.
46. Hoffmann R, Stieglitz T, Hosseini N H, Kisban S, Paul O, Ruther P. Comparative Study on the Insertion Behavior of Cerebral Microprobes. In: Engineering in Medicine and Biology Society, 2007. EMBS 2007. 29th Annual International Conference of the IEEE. 2007. p. 4711-4.
47. Polikov V S, Block M L, Fellous J-M, Hong J-S, Reichert W M. In vitro model of glial scarring around neuroelectrodes chronically implanted in the CNS. Biomaterials. 2006 November; 27(31):5368-76.
48. Polikov V S, Su E C, Ball M A, Hong J-S, Reichert W M. Control protocol for robust in vitro glial scar formation around microwires: Essential roles of bFGF and serum in gliosis. Journal of Neuroscience Methods. 2009 Jul. 30; 181(2):170-7.
49. Szarowski D H, Andersen M D, Retterer S, Spence A J, Isaacson M, Craighead H G, et al. Brain responses to micro-machined silicon devices. Brain Research. 2003 Sep. 5; 983(1-2):23-35.
50. Skousen J L, Merriam S M E, Srivannavit O, Perlin G, Wise K D, Tresco P A. Reducing surface area while maintaining implant penetrating profile lowers the brain foreign body response to chronically implanted planar silicon microelectrode arrays. Prog. Brain Res. 2011; 194:167-80.
51. Jiang C, Wang X, Gunawidjaja R, Lin Y-H, Gupta M K, Kaplan D L, et al. Mechanical Properties of Robust Ultrathin Silk Fibroin Films. Advanced Functional Materials. 2007 Sep. 3; 17(13):2229-37.
52. Lawrence B D, Wharram S, Kluge J A, Leisk G G, Omenetto F G, Rosenblatt M I, et al. Effect of Hydration on Silk Film Material Properties. Macromolecular Bioscience. 2010 Apr. 8; 10(4):393-403.
53. Bjornsson C S, Oh S J, Al-Kofahi Y A, Lim Y J, Smith K L, Turner J N, et al. Effects of insertion conditions on tissue strain and vascular damage during neuroprosthetic device insertion. J. Neural Eng. 2006 September; 3(3): 196-207.
54. A. K. H. Achyuta, V. S. Polikov, A. J. White, H. G. P. Lewis, and S. K. Murthy, "Biocompatibility assessment of insulating silicone polymer coatings using an in vitro glial scar assay," Macromolecular Bioscience, vol. 10, no. 8, pp. 872-880, August 2010.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An implantable device comprising a silk body and a reservoir,
    the silk body comprising an outer surface, wherein at least a portion of the outer surface comprises a silk coating;
    the silk body further comprising conduits formed between the outer surface and the reservoir; and
    the reservoir configured to hold a silk matrix therein, wherein the silk matrix forms the silk coating upon discharge from the reservoir onto the at least a portion of the outer surface through the conduits.

2. The implantable device of claim 1, wherein the silk body comprises a lumen extending through the silk body or at least one compartment distributed within the silk body, wherein the lumen or the at least one compartment forms the reservoir.

3. The implantable device of claim 2, wherein the silk matrix in the reservoir is a silk solution.

4. The implantable device of claim 1, wherein the silk body comprises a first silk layer and a second silk layer, wherein an interlamellar space between the first silk layer and the second silk layer forms the reservoir.

5. The implantable device of claim 4, wherein the interlamellar space between the first silk layer and the second silk layer comprises silk particles or powders.

6. The implantable device of claim 1, wherein the at least a portion of the outer surface further comprises an electrically-conducting component, wherein the silk coating is formed on a surface of at least a portion of the electrically-conducting component.

7. The implantable device of claim 6, wherein when the silk matrix is discharged onto the surface of at least the portion of the electrically-conducting component and forms a silk solution thereon, the silk solution forms a gel coating upon application of a first voltage to the silk solution through the electrically-conducting component, and wherein the gel coating turns to a solution upon application of a second voltage with a polarity opposite to the first voltage.

8. The implantable device of claim 6, wherein the electrically-conducting component includes silk modified to be capable of conducting electricity.

9. The implantable device of claim 8, wherein a tyrosine of a silk protein is modified to a sulfate group followed by polymerization of the modified tyrosine with a conducting polymer.

10. The implantable device of claim 8, wherein the silk is doped with a conductive material.

11. The implantable device of claim 1, wherein the implantable device is adapted to be an implantable brain penetrating electrode.

12. The implantable device of claim 11, wherein the electrode has a tensile strength of at least about 2 MPa when the silk body is in a dry state.

13. The implantable device of claim 11, wherein the electrode has a shear modulus of less than about 200 kPa upon contact of the silk body with a fluid.

14. A method of reducing biofouling around an implantable device upon implantation in a tissue comprising implanting the implantable device of claim 1 in a tissue, wherein the silk matrix is discharged from the reservoir onto a surface of an electrically-conducting component and forms a silk coating thereon, thereby reducing biofouling around the implantable device.

15. The method of claim 14, wherein the silk matrix discharged onto the surface of the electrically-conducting component forms a silk solution thereon.

16. The method of claim 15, wherein when a first voltage is applied to the silk solution through the electrically-conducting component, the silk solutions forms a gel coating onto the surface of the electrically-conducting component; and when a second voltage with a polarity opposite to the first voltage is applied to the gel coating, the gel coating turns to a solution, thereby renewing the silk coating around.

* * * * *